United States Patent
Lamble et al.

(10) Patent No.: US 11,591,644 B2
(45) Date of Patent: Feb. 28, 2023

(54) NUCLEIC ACID DETECTION METHOD

(71) Applicant: Sense Biodetection Limited, Abingdon (GB)

(72) Inventors: Henry John Lamble, Abingdon (GB); David Lloyd, Abingdon (GB); Christopher Egan, Abingdon (GB)

(73) Assignee: Sense Biodetection Limited, Abingdon (GB)

(*) Notice: Subject to any disclaimer, the term of this patent is extended or adjusted under 35 U.S.C. 154(b) by 631 days.

(21) Appl. No.: 16/480,521

(22) PCT Filed: Jan. 25, 2018

(86) PCT No.: PCT/GB2018/050207
§ 371 (c)(1),
(2) Date: Jul. 24, 2019

(87) PCT Pub. No.: WO2018/138499
PCT Pub. Date: Aug. 2, 2018

(65) Prior Publication Data
US 2020/0002756 A1    Jan. 2, 2020

(30) Foreign Application Priority Data
Jan. 25, 2017 (GB) .................................. 1701262

(51) Int. Cl.
*C12Q 1/6844* (2018.01)
*C12Q 1/682* (2018.01)

(52) U.S. Cl.
CPC .......... *C12Q 1/6844* (2013.01); *C12Q 1/682* (2013.01); *C12Q 2521/301* (2013.01); *C12Q 2527/101* (2013.01); *C12Q 2531/119* (2013.01); *C12Q 2533/101* (2013.01); *C12Q 2537/143* (2013.01); *C12Q 2565/549* (2013.01)

(58) Field of Classification Search
CPC ............................ C12Q 1/6844; C12Q 1/682; C12Q 2521/301; C12Q 2527/101; C12Q 2531/119; C12Q 2533/101; C12Q 2537/143; C12Q 2565/549
See application file for complete search history.

(56) References Cited

U.S. PATENT DOCUMENTS

| | | |
|---|---|---|
| 5,011,769 A | 4/1991 | Duck |
| 5,403,711 A | 4/1995 | Walder |
| 2003/0082590 A1 | 1/2003 | Van Ness |
| 2009/0081670 A1 | 3/2009 | Maples |

FOREIGN PATENT DOCUMENTS

| | | |
|---|---|---|
| WO | 97/12062 A1 | 4/1997 |
| WO | 99/01569 A2 | 1/1999 |
| WO | 2003/008622 A2 | 1/2003 |
| WO | 2003054214 A2 | 7/2003 |
| WO | 2005052127 A2 | 6/2005 |
| WO | 2006088910 A2 | 8/2006 |
| WO | 2008/028086 A2 | 3/2008 |
| WO | 2010096202 A2 | 8/2010 |
| WO | 2016/103234 A1 | 6/2016 |
| WO | 2017/017424 A1 | 2/2017 |

OTHER PUBLICATIONS

Craw, P. Balachandran, W. Isothermal nucleic acid amplification technologies for point-of-care diagnostics: a critical review. Lab Chip. Jul. 21, 2012; 2469-86; 12(14), The Royal Society of Chemistry.

Xuemei Li et al. Ultrasensitive DNA detection by cycle isothermal amplification based on nicking endonuclease and its application to logic gates. Biosensors and Bioelectronics, Elsevier BV, vol. 30, No. 1. Sep. 16, 2011, pp. 241-248.

Qing Zhang et al. Target-triggered three-way junction structure and polymerase/nicking enzyme synergetic isothermal quadratic DNA machine for highly specific, one-step and rapid microRNA detection at attomolar level. Analytical Chemistry, vol. 86, No. 16, Jul. 29, 2014, pp. 8098-8105.

Van Ness et al. Isothermal reactions for the amplification of oligonucleotides. PNAS, 100(8), Apr. 15, 2003, pp. 4504-4509.

*Primary Examiner* — David C Thomas
(74) *Attorney, Agent, or Firm* — Morgan, Lewis & Bockius LLP

(57) ABSTRACT

The present invention relates to methods for the detection of nucleic acids of defined sequence and kits for use in said methods. The methods employ nicking agent(s), polymerase and oligonucleotide probes to produce probe fragments in the presence of a target nucleic acid.

29 Claims, 20 Drawing Sheets
Specification includes a Sequence Listing.

a)

b)

Probe Fragment:

100pmol

10pmol 0.1pmol 0.01pmol

—

Target Nucleic Acid:

25fmol 2.5fmol

—

Viral Nucleic Acid Target:     - + - +
Bacterial Nucleic Acid Target: - - + +

← Bacterial Positive Test Result
← Viral Positive Test Result

SEQUENCE LISTING

```
<160> NUMBER OF SEQ ID NOS: 27

<210> SEQ ID NO 1
<211> LENGTH: 40
<212> TYPE: DNA
<213> ORGANISM: Artificial Sequence
<220> FEATURE:
<223> OTHER INFORMATION: Oligonucleotide

<400> SEQUENCE: 1
atatatatat aggagtctcg gcatctatat atatatatat                 40

<210> SEQ ID NO 2
<211> LENGTH: 43
<212> TYPE: DNA
<213> ORGANISM: Artificial Sequence
<220> FEATURE:
<223> OTHER INFORMATION: Oligonucleotide

<400> SEQUENCE: 2
atatatatat atatatttga gtcatagaga tgccgagact cct             43

<210> SEQ ID NO 3
<211> LENGTH: 37
<212> TYPE: DNA
<213> ORGANISM: Artificial Sequence
<220> FEATURE:
<223> OTHER INFORMATION: Oligonucleotide

<400> SEQUENCE: 3 ttttttttttt tttttgagag ccaggaccag gaacaca                   37

<210> SEQ ID NO 4
<211> LENGTH: 37
<212> TYPE: DNA
<213> ORGANISM: Artificial Sequence
<220> FEATURE:
<223> OTHER INFORMATION: Oligonucleotide

<400> SEQUENCE: 4 ttttttttttt tttttgtgt tcctggtcct ggctctc                    37

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide

<400> SEQUENCE: 5
attaatacca tcaaaatgta tatat                                 25

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
atatatacat tttgatggta t                                     21
```

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
atatatacat tttgaaggta t                                              21

<210> SEQ ID NO 8
<211> LENGTH: 13
<212> TYPE: DNA
<213> ORGANISM: Artificial Sequence
<220> FEATURE:
<223> OTHER INFORMATION: Oligonucleotide

<400> SEQUENCE: 8
attttgatgg tat                                                       13

<210> SEQ ID NO 9
<211> LENGTH: 102
<212> TYPE: DNA
<213> ORGANISM: Artificial Sequence
<220> FEATURE:
<223> OTHER INFORMATION: Oligonucleotide

<400> SEQUENCE: 9
ttactgagga tattgcttga agctggcagt gcctctcgat ccgaatgctc agagacagaa    60
gagcgcaatg gggactctta ctgaggatat tgcttgaagc tg                      102

<210> SEQ ID NO 10
<211> LENGTH: 42
<212> TYPE: DNA
<213> ORGANISM: Artificial Sequence
<220> FEATURE:
<223> OTHER INFORMATION: Oligonucleotide

<400> SEQUENCE: 10
aaaaaaaaaa gtaaagagt ctgtccatca ctaaaaaaa aa                         42

<210> SEQ ID NO 11
<211> LENGTH: 40
<212> TYPE: DNA
<213> ORGANISM: Artificial Sequence
<220> FEATURE:
<223> OTHER INFORMATION: Oligonucleotide

<400> SEQUENCE: 11 atatatat attaaaccaa gtaccgcact atatatat                              40

<210> SEQ ID NO 12
<211> LENGTH: 34
<212> TYPE: DNA
<213> ORGANISM: Artificial Sequence
<220> FEATURE:
<223> OTHER INFORMATION: Oligonucleotide

<400> SEQUENCE: 12
atatatatat cgcagtctct gaatatatat atat                                34

<210> SEQ ID NO 13
<211> LENGTH: 38
<212> TYPE: DNA

<213> ORGANISM: Artificial Sequence
<220> FEATURE:
<223> OTHER INFORMATION: Oligonucleotide

<400> SEQUENCE: 13
aaaaaaaaaa gagaggcact gccagcttaa aaaaaaaa                                    38

<210> SEQ ID NO 14
<211> LENGTH: 39
<212> TYPE: DNA
<213> ORGANISM: Artificial Sequence
<220> FEATURE:
<223> OTHER INFORMATION: Oligonucleotide

<400> SEQUENCE: 14
atatatatac gccagccatt gcaacaggaa tatatatat                                   39

<210> SEQ ID NO 15
<211> LENGTH: 44
<212> TYPE: DNA
<213> ORGANISM: Artificial Sequence
<220> FEATURE:
<223> OTHER INFORMATION: Oligonucleotide

<400> SEQUENCE: 15
atatatatat atattttcgt ctcgattcga tatcttgact cctt                             44

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide

<400> SEQUENCE: 16
ttcttcttct tggtctcact catgaggacg cc                                          32

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide

<400> SEQUENCE: 17
ttcttcttct tggtctccag gagaccggtc tt                                          32

<210> SEQ ID NO 18
<211> LENGTH: 36
<212> TYPE: DNA
<213> ORGANISM: Artificial Sequence
<220> FEATURE:
<223> OTHER INFORMATION: Oligonucleotide

<400> SEQUENCE: 18
caggagaccg gtcttcccga gggcgtcctc aggagt                                      36

<210> SEQ ID NO 19
<211> LENGTH: 46
<212> TYPE: DNA
<213> ORGANISM: Artificial Sequence
<220> FEATURE:
<223> OTHER INFORMATION: Oligonucleotide

<400> SEQUENCE: 19
ccttgtgttc accggtcttc ccgagggttt tcttcttct tttttt                            46

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide

<400> SEQUENCE: 20
ttcttcttct tggtctcact catgaggacg cc                                    32

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide

<400> SEQUENCE: 21
ttgttgttgt tggtctcgga gaccggatcg tt                                    32

<210> SEQ ID NO 22
<211> LENGTH: 60
<212> TYPE: DNA
<213> ORGANISM: Artificial Sequence
<220> FEATURE:
<223> OTHER INFORMATION: Oligonucleotide

<400> SEQUENCE: 22
tgtccatgtt tttttggaga ccggatcgtt acggcgtcct catgagtaaa aatgtccatg      60

<210> SEQ ID NO 23
<211> LENGTH: 43
<212> TYPE: DNA
<213> ORGANISM: Artificial Sequence
<220> FEATURE:
<223> OTHER INFORMATION: Oligonucleotide

<400> SEQUENCE: 23
ccttgtgttc ccggatcgtt acggcttttc ttcttctttt ttt                        43

<210> SEQ ID NO 24
<211> LENGTH: 33
<212> TYPE: DNA
<213> ORGANISM: Artificial Sequence
<220> FEATURE:
<223> OTHER INFORMATION: Oligonucleotide

<400> SEQUENCE: 24
gttgttgtgc ttcccgagga cgccaataga gga                                   33

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide

<400> SEQUENCE: 25
gttgttgtgc ttcccgagta gaggcaggtg acc                                   33

<210> SEQ ID NO 26
<211> LENGTH: 64
<212> TYPE: DNA
<213> ORGANISM: Artificial Sequence
<220> FEATURE:

```
<223> OTHER INFORMATION: Oligonucleotide

<400> SEQUENCE: 26
tgtccatgtt tttttagag gcaggtgacc ggtctcctct attggcgtcc aaaaaatgtc      60
catg                                                                  64

<210> SEQ ID NO 27
<211> LENGTH: 43
<212> TYPE: DNA
<213> ORGANISM: Artificial Sequence
<220> FEATURE:
<223> OTHER INFORMATION: Oligonucleotide

<400> SEQUENCE: 27
ccttgtgttc ccggtctcct ctattgtttt tcttcttctt ttt                       43
```

NUCLEIC ACID DETECTION METHOD

CROSS-REFERENCE TO RELATED APPLICATIONS

This application is a National Stage application of International Application No. PCT/GB2018/050207, filed Jan. 25, 2018, which claims priority to GB Patent Application 1701262.6 filed Jan. 25, 2017, the contents of which are incorporated herein by reference in their entireties.

BACKGROUND

Technical Field

The present invention is directed to methods for the detection of nucleic acids of defined sequence and compositions for use in said methods.

Related Art

Methods of nucleic acid sequence amplification based on polymerases are widely used in a number of fields such as molecular biology research and the molecular diagnosis of disease. The most established method, polymerase chain reaction (PCR), typically involves two primers and uses temperature to achieve primer annealing, extension by DNA polymerase and denaturation of newly synthesised DNA in a cyclical exponential amplification process. The requirement for temperature cycling necessitates complex equipment which limits the use of PCR-based methods in certain applications.

As such, a number of isothermal nucleic acid detection methods have been developed that do not require temperature cycling (Reviewed by Craw and Balachandran (2012) *Lab Chip* 12, 2469), such as Loop-mediated isothermal amplification (LAMP), Rolling Circle Amplification (RCA), Isothermal and Chimeric primer-initiated Amplification of Nucleic acids (ICAN), Strand Displacement Amplification (SDA), Helicase Dependent Amplification (HDA), Recombinase Polymerase Amplification (RPA), Nicking and Extension Amplification Reaction (NEAR), Nucleic Acid Sequence-Based Amplification (NASBA), EXPonential Amplification Reaction (EXPAR), SMart Amplification Process (SMAP2), Single Primer Isothermal Amplification (SPIA) and Beacon Assisted Detection AMPlification (BAD AMP). These methods typically exploit DNA polymerase(s), to achieve exponential amplification which is essential for their utility in nucleic acid detection. Instead of using temperature to achieve the annealing and denaturation of double-stranded DNA during polymerase amplification, they use additional enzymes and probes which increases complexity, and they typically yield a double stranded nucleic acid product containing the target sequence which can present a challenge for efficient signal detection.

NEAR (US20090081670) uses oligonucleotide(s), nicking enzyme(s) and polymerase to achieve signal amplification. It introduces nicking sites at the 5' end of each of two oligonucleotide primers and thus produces a double-stranded nucleic acid product that comprises the original target sequence. The double-stranded nature of the amplified product presents a challenge for coupling of the method to signal detection since it is not possible to perform hybridisation-based detection without first separating the two strands. Further, the requirement to amplify the target sequence means that the sequence of the amplified product is defined by the target and thus any sequence based specific detection method to be coupled to the amplification method needs to be adapted for each new target.

EXPAR (Van Ness et al. (2003) *PNAS* 100, 4504-4509) is a method that also exploits oligonucleotide(s), nicking enzyme(s) and polymerase to achieve amplification. Linear EXPAR produces multiple copies of a displaced single-stranded nucleic acid, however, the amplification exhibits very low sensitivity. Exponential EXPAR, which exploits cross-priming of the displaced single-stranded nucleic acids produced, shows some improved sensitivity, but is hampered by non-specific background and does not benefit from an intrinsic signal detection method. As a result it is frequently not possible to distinguish target-dependent EXPAR amplification from non-specific background and thus the method has not been widely adopted in the field.

There is an important requirement for new methods for rapid, sensitive and specific nucleic acid sequence detection to overcome the requirement for temperature cycling of PCR and the complexity and challenges of existing isothermal methods. The present invention relates to a method of nucleic acid sequence detection which achieves exponential signal amplification using nicking agent(s), polymerase and oligonucleotide probe(s), without requirement for temperature cycling and which produces a single-stranded amplified product of any desired sequence that is particularly amenable to efficient signal detection.

SUMMARY

The invention provides a method for detecting the presence of a target nucleic acid of defined sequence in a sample which method comprises the steps of:
a) contacting said sample with:
   i. a first oligonucleotide probe (P1);
   ii. a polymerase; and
   iii. a first nicking agent;
   to produce in the presence of the target nucleic acid a double-stranded nucleic acid amplifier comprising a target derived strand and a probe (P1) derived strand and containing at least one cleavage site for a first nicking agent in the target derived strand; wherein the first oligonucleotide probe (P1) comprises a complementarity region capable of sequence specific hybridisation to the target nucleic acid; and whereby in the presence of the target nucleic acid: (A) the first nicking agent specifically recognises the double-stranded nucleic acid amplifier and cleaves the target derived strand of the double-stranded nucleic acid amplifier at said cleavage site to produce a primer that remains hybridised to the probe (P1) derived strand; and (B) the polymerase extends said primer to reproduce said double-stranded nucleic acid amplifier and displaces the target derived strand fragment (F1) that is 3' of said cleavage site;
b) contacting the fragment (F1) produced in step a) with:
   i. a second oligonucleotide probe (P2); and
   ii. a second nicking agent;
   wherein the second oligonucleotide probe (P2) comprises a complementarity region capable of sequence specific hybridisation to fragment (F1) which following hybridisation to fragment (F1) produces a cleavage site for the second nicking agent; whereby the second nicking agent specifically recognises the double-stranded nucleic acid formed when the second oligonucleotide probe (P2) hybridises to fragment F1 and cleaves said second oligonucleotide probe (P2) to produce a probe fragment (F2); and c) detecting the presence of the probe fragment (F2) produced in step b) wherein the presence of said detected probe fragment (F2) indicates the presence of the target nucleic acid in said sample.

An embodiment of the method is illustrated in FIG. 1.

In various embodiments, in the presence of target nucleic acid the method produces an exponentially increasing number of the single stranded probe fragment (F2) which forms the basis of its sensitive detection.

The present invention in various aspects is advantageous over known methods because it encompasses improved amplification and thus it has greatly improved potential for application in the sensitive detection of target nucleic acids of defined sequence. The method is not focussed on amplifying a particular target per se, i.e. generating many copies of the original target sequence, which is the exclusive focus of most other polymerase-based methods, such as PCR and NEAR. Instead an intrinsic aspect of the method of the invention is that in the presence of the target nucleic acid it produces many copies of a single-stranded probe fragment of any desired sequence, which is particularly amenable to efficient signal detection. In various embodiments the present invention derives enhanced specificity over known methods by using restriction enzymes and targeting a restriction enzyme binding site present within the target nucleic acid, thus providing a further sequence verification in addition to that derived from the hybridisation of nucleic acids alone. Known methods frequently require two independent primer hybridisation events to derive specificity. Due to the enhanced specificity derived from restriction enzyme binding, the present invention can even perform specific and sensitive detection with only a single probe interacting with the target, thus greatly simplifying assay design. Alternative embodiments that exploit two probe or primer interactions with the target derive enhanced specificity over known methods by additionally exploiting the restriction enzyme binding site present within the target nucleic acid. Furthermore, improved rigour of sequence verification enables low temperature reactions to be performed without loss of specificity and/or enables increased multiplexing, where multiple reactions are performed for simultaneous detection of multiple targets. A further aspect of the present invention is the ability to use double-strand cleaving agents as nicking agents, which overcomes the sequence space limitations of known methods that are only performed with nicking endonucleases, and therefore enables restriction enzymes for a wider range of target sites to be identified.

The invention provides increased flexibility in probe design and nicking agent selection as there is no requirement for the probe fragment(s) to be a functional equivalent of the target sequence, i.e. having full or partial sequence homology. This allows optimisation of sequences and nicking agents for efficient detection. Removing the requirement for generation of functional equivalents of the target also provides the opportunity to develop a universal detection system whereby at least the probe (P2) in step b) and the detection system can be used from application to application and target to target without needing to be altered. This "universal" detection system can be coupled to an alternative probe (P1) in step a), without the reaction components and detection system having to be altered each time.

The invention also provides a greater degree of versatility in multiplexing with multiple assays being more readily combined for the detection of multiple targets than known detection methods. Multiple targets (e.g. different strains of a pathogen) can either be differentially detected or detected together through the same signal. For example, probe fragments generated from cleavage of multiple different variants of the first oligonucleotide probe (P1), if desired, could be linked to the same second oligonucleotide probe (P2). In a system which uses "functional target equivalents" as the end-point of the amplification there is an increased risk of cross-talk which reduces the multiplexing potential. Furthermore, multiplexing requires significant optimisation of probe sequences to ensure they function well together. As described above, in a universal amplification and detection system a number of oligonucleotide probes can be developed and optimised to be compatible together in advance and then repurposed for any given target solely by replacing the first oligonucleotide probe or any other target binding probes or primers used in the method.

The invention utilises "end-point detection" which provides further advantages over amplification methods which produce a double-stranded DNA product or where every nucleic acid present has the potential to hybridise to another nucleic acid present in the reaction. The latter causes a significant problem because such products are hybridised and require separation before they can be efficiently and quantitatively detected. In other words, there is no "end-point" probe fragment which accumulates without the ability to hybridise. Such an "end-point" probe is attractive to form the basis of the probe fragment which is detected. Detection of that probe fragment can be done efficiently by hybridisation to a complementary probe because it is single-stranded DNA. Detection by hybridisation is particularly amenable to multiplex detection, e.g. by nucleic acid lateral flow, because the complementary sequence of the probe fragment(s) from different series of the probes can be printed on a lateral flow strip. Various embodiments of the above mentioned aspects of the invention, and further aspects, are described in more detail below.

DETAILED DESCRIPTION

Figure 1:
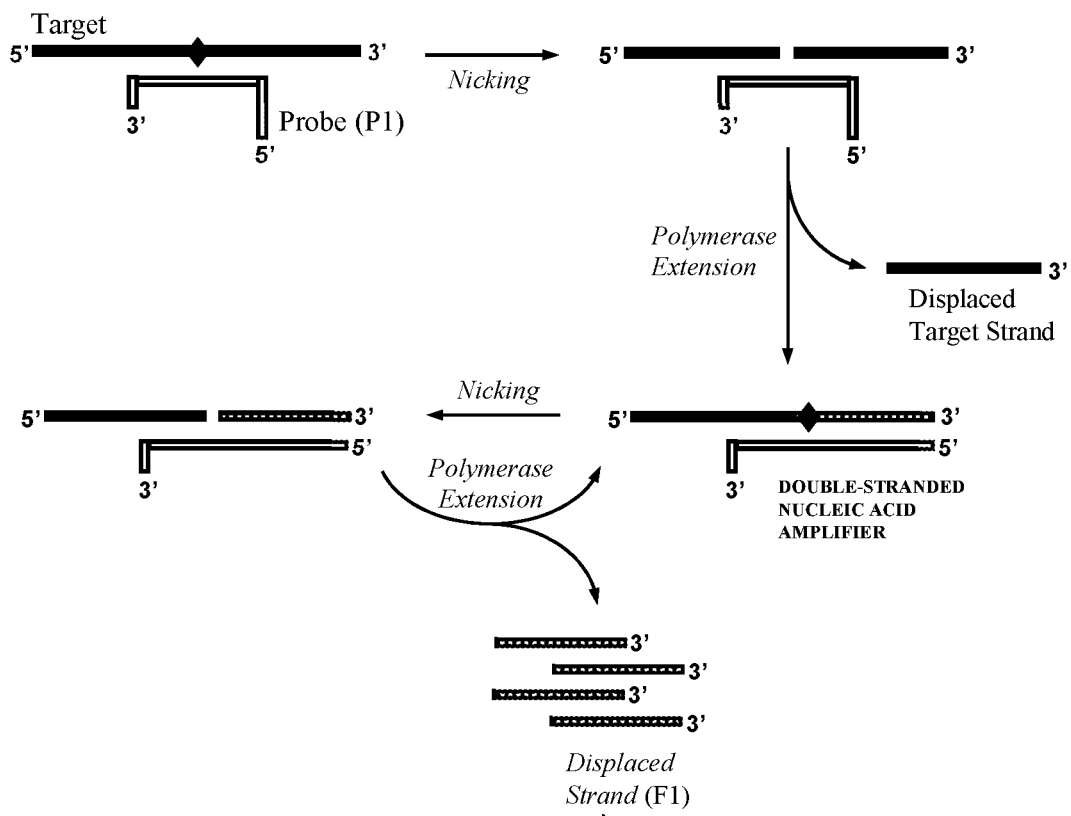
FIG. 1. Schematic representation of the method according to one aspect of the invention.
Figure 1:
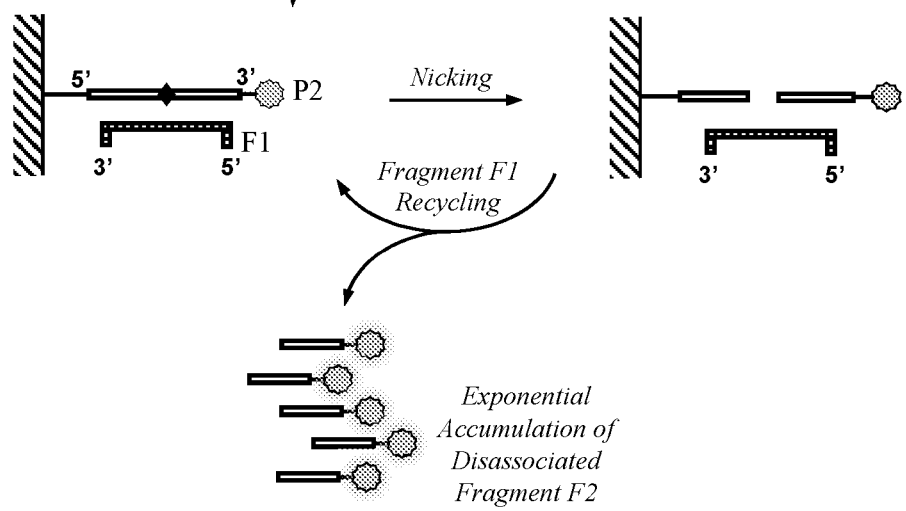

We have developed a method for detecting the presence of a target nucleic acid of defined sequence in a sample. The target nucleic acid may be single-stranded DNA, including single-stranded DNA derived from double-stranded DNA following disassociation of the two strands such as by heat denaturation or through strand displacement activity of a polymerase, or derived from RNA by the action of reverse transcriptase, or derived from double-stranded DNA by use of a nuclease, such as a restriction endonuclease or exonuclease III, or derived from a RNA/DNA hybrid through an enzyme such as Ribonuclease H. The target nucleic acid may be single-stranded RNA, including single-stranded RNA derived from double-stranded RNA following disassociation of the two strands such as by heat denaturation or derived from DNA by transcription. The target nucleic acid may be DNA derived from DNA by a DNA polymerase.

The method involves, in step a), contacting the sample with (i) a first oligonucleotide probe (P1) comprising a complementarity region capable of sequence specific hybridisation to the target nucleic acid; (ii) a polymerase; and (iii) a first nicking agent. In the presence of target nucleic acid, probe (P1) hybridises in a sequence specific manner to the target nucleic acid. The resulting double-stranded nucleic acid may be a double-stranded DNA, a double stranded RNA or a hybrid duplex comprising strands of both RNA and DNA. Typically, the oligonucleotide probes, and all probes and primers used in the method, are DNA probes which form with the DNA or RNA target a double stranded DNA or a hybrid duplex comprising strands of both RNA and DNA. However, RNA probes or probes comprising other nucleic acids, such as non-natural bases and/or alternative backbone structures, may also be used. Following hybridisation of probe (P1) to the target nucleic acid a double-stranded nucleic acid amplifier is produced through the action of the polymerase and/or the first nicking agent, wherein said double-stranded nucleic acid amplifier contains a target derived strand and a probe (P1) derived strand and contains at least one cleavage site for the first nicking agent in the target derived strand. Oligonucleotide probe (P1) is typically designed to target a recognition sequence for the first nicking agent within the target nucleic acid, leading to the introduction of the cleavage site for the first nicking agent into the double-stranded nucleic acid amplifier. Probe (P1) typically either comprises the reverse complement of said recognition sequence (see FIG. 1) or is designed to hybridise such that its 3' end hybridises 3' of the recognition sequence in the target nucleic acid, typically within 0-50 bases, such that the extension of probe (P1) by the polymerase leads to the introduction of the recognition sequence and cleavage site within the target derived strand (see FIG. 2A-D). Various embodiments of the method comprise one or more additional probe or primer and one or more additional nicking agent in order to produce the double-stranded nucleic acid amplifier and derive additional amplification.

Following production of the double-stranded nucleic acid amplifier: (A) the first nicking agent specifically recognises the double-stranded nucleic acid amplifier and cleaves the target derived strand of the double-stranded nucleic acid amplifier at said cleavage site to produce a primer that remains hybridised to the probe (P1) derived strand; and (B) the polymerase extends said primer to reproduce said double-stranded nucleic acid amplifier and displaces the target derived strand fragment (F1) that is 3' of said cleavage site. The foregoing process is repeated through the sequential action of the first nicking agent and the polymerase to displace multiple copies of fragment (F1) from each double-stranded nucleic acid amplifier. This embodiment of step a) of the method represents a linear (first order) reaction wherein each target nucleic acid molecule produces one double-stranded nucleic acid amplifier, each of which produces a given number of displaced fragments in a given period of time.

The method involves, in step b), contacting the fragment (F1) produced in step a) with:
  i. a second oligonucleotide probe (P2); and
  ii. a second nicking agent;
wherein the second oligonucleotide probe (P2) comprises a complementarity region capable of sequence specific hybridisation to fragment (F1) which following hybridisation to fragment (F1) produces a cleavage site for the second nicking agent; whereby the second nicking agent specifically recognises the double-stranded nucleic acid formed when the second oligonucleotide probe (P2) hybridises to fragment (F1) and cleaves said second oligonucleotide probe (P2) to produce a probe fragment (F2). Fragment (F1) undergoes target recycling; in that it is able to hybridise to another probe (P2) for the process to repeat. Therefore step b) leads to the production of multiple copies of (F2) from each copy of (F1) in a linear (first order) reaction. By combining two first order reactions (step a) and step b) of the method) the present invention becomes an inherently exponential (second order) reaction, illustrating its enhanced sensitivity potential over known methods such as EXPAR.

"Target recycling" refers to a cyclical process whereby a target nucleic acid following sequence specific hybridisation to an oligonucleotide probe and cleavage of said probe by a nicking agent, is left intact and able to undergo sequence specific hybridisation to further oligonucleotide probes for the process to repeat. Following cleavage by a nicking agent, an oligonucleotide probe produces two shorter oligonucleotide fragments, which dissociate from the target nucleic acid in a process which is likely to be favoured by a significant decrease in melting temperature of the duplexes formed by said shorter oligonucleotide fragments compared to the original oligonucleotide probe. As it is unaffected by the cleavage and hybridisation process, the target nucleic acid is then subsequently available for sequence specific hybridisation to further oligonucleotide probes for repetition of the process. In the present invention probe fragment (F1) displaced from the double-stranded nucleic acid amplifier acts as a target nucleic acid for the cleavage of oligonucleotide probe (P2). As such the concept of target recycling should also be considered to encompass the recycling of probe fragment (F1) (see FIG. 1).

Typically the sequence of probe (P1) is designed such that it or the probe (P1) derived strand contains one or more region with the same sequence as the complementarity region of probe (P2) that is capable of sequence specific hybridisation to fragment (F1). Therefore, when the polymerase extends from the nicking cleavage site(s) of the target derived nucleic acid strand, fragment (F1) is produced with the reverse complementary sequence necessary for sequence specific hybridisation to probe (P2) at the cleavage site for the second nicking agent. Following specific recognition of the double stranded nucleic acid by the second nicking agent, the second nicking agent cleaves (P2) to produce the second probe fragment (F2) leaving (F1) at least functionally intact, in that it is capable of target recycling. When probe (P1) contains one or more region with the same sequence as the complementarity region of (P2), the (P1) derived strand of the double-stranded nucleic acid amplifier has the potential to be cleaved by the second nicking agent, which could hamper the performance of step a) of the method. The cleavage of the (P1) derived strand by the second nicking agent may be avoided by the use of two different nicking agents as the first and second nicking agent when step a) is performed as a separate step prior to contacting the double-stranded nucleic acid amplifier with the second nicking agent in step b). A more versatile option to avoid the cleavage of the (P1) derived strand is to use a modified form of oligonucleotide probe (P1), e.g. wherein one or more of the nucleotide bases or phosphodiester linkages of (P1) is resistant to cleavage by the second nicking agent. Thus, in an embodiment of the invention the probe (P1) derived strand of the double-stranded nucleic acid amplifier comprises one or more modifications, such as one or more phosphorothioate linkage, that render it resistant to cleavage by the first and/or second nicking agent.

In an alternative embodiment of step b) of the method, fragment (F1) is capable of sequence specific hybridisation to probe (P2) such that its 3' terminus is extended by a polymerase to produce the double stranded nucleic acid that contains the cleavage site for the second nicking agent within (P2). Following specific recognition of the double stranded nucleic acid by the second nicking agent, the second nicking agent cleaves (P2) to produce the second probe fragment (F2) leaving the extended form of (F1) at least functionally intact, in that it is capable of target recycling.

In step c) of the method the presence of the probe fragment (F2) produced at the end of step b) is detected and the presence of said detected probe fragment (F2) indicates the presence of the target nucleic acid in said sample.

The double-stranded nucleic acid amplifier in step a) may be produced in a number of different ways. In one embodiment illustrated in FIG. 1, the first oligonucleotide probe (P1) comprises a complementarity region capable of sequence specific hybridisation to the target nucleic acid to produce a cleavage site for the first nicking agent in the target derived strand; and whereby the first nicking agent specifically recognises the double-stranded nucleic acid formed when the first oligonucleotide probe (P1) hybridises to the target nucleic acid in said sample and cleaves said target nucleic acid to produce a primer that remains hybridised to the probe (P1); and the polymerase extends the primer to produce the double-stranded nucleic acid amplifier.

Figure 2A:
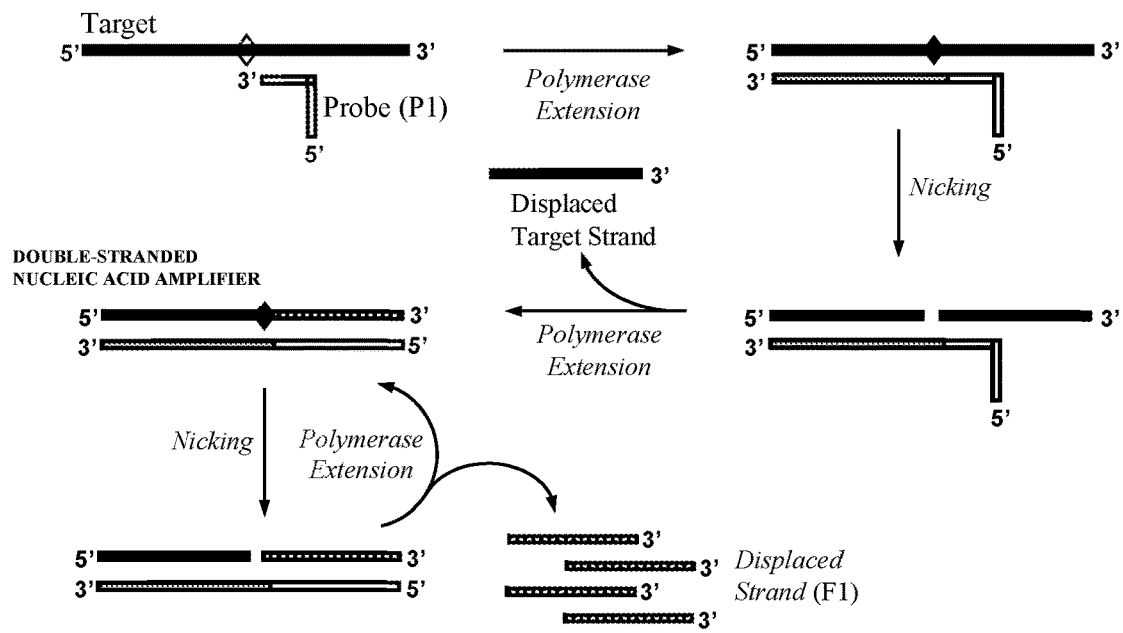
FIG. 2A. Schematic representation of production of a double-stranded nucleic acid amplifier by polymerase extension of oligonucleotide probe (P1).

In another embodiment, illustrated in FIG. 2A, the first oligonucleotide probe (P1) comprises a complementarity region at its 3' end that is capable of sequence specific hybridisation to the target nucleic acid; whereby, on hybridisation of probe (P1) to the target nucleic acid, extension of (P1) by the polymerase forms a double-stranded nucleic acid that contains the cleavage site for the first nicking agent within the target nucleic acid strand; and whereby the first nicking agent specifically recognises said double-stranded nucleic acid and cleaves said target nucleic acid strand to produce a primer that remains hybridised to the probe (P1) derived strand; and the polymerase extends the primer to produce the double-stranded nucleic acid amplifier.

Figure 2B:
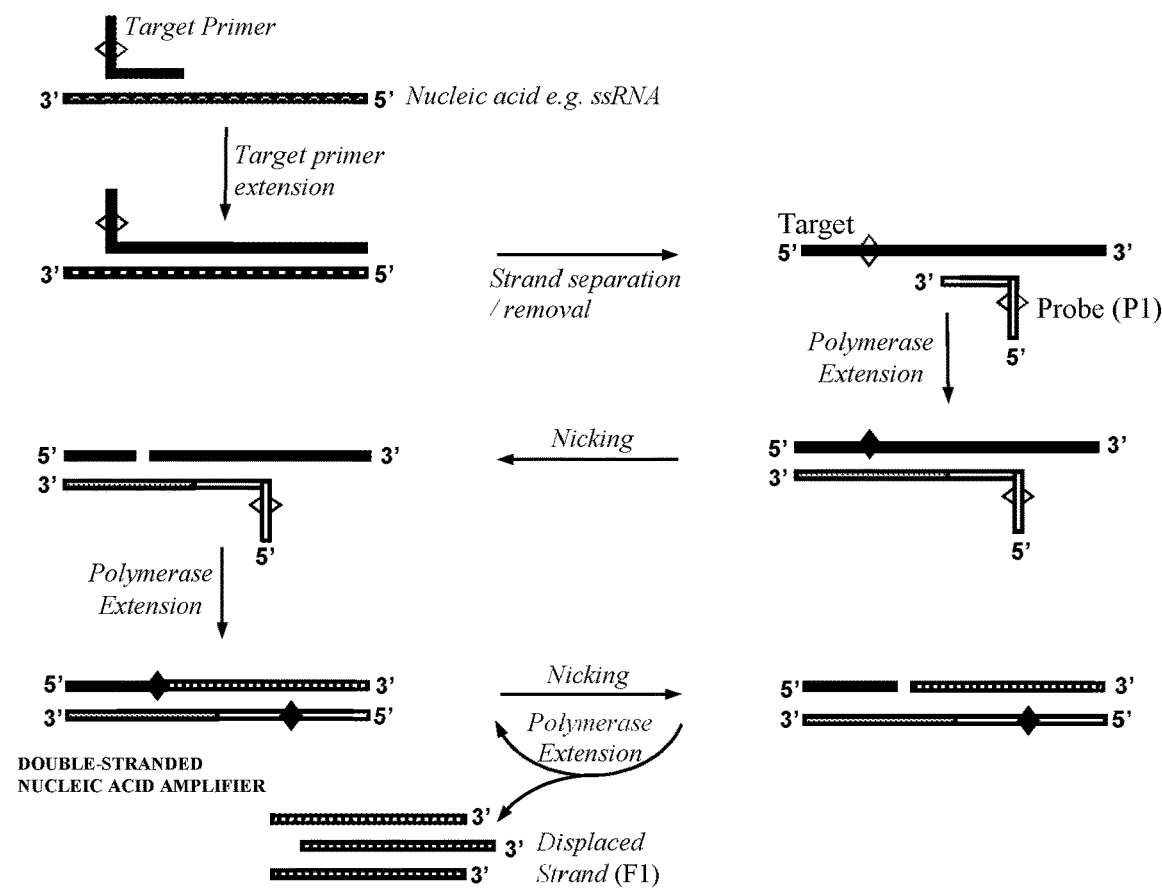
FIG. 2B. Schematic representation of production of a double-stranded nucleic acid amplifier that contains one or more cleavage site in the target derived strand and one or more cleavage site in the probe (P1) derived strand, wherein the target nucleic acid is single-stranded cDNA produced by reverse transcription.

In a further embodiment, illustrated in FIG. 2B, probe (P1) contains the recognition sequence for a probe (P1) nicking agent and wherein the double-stranded nucleic acid amplifier therefore contains two or more nicking agent cleavage sites, one or more cleavage site in the target derived strand and one or more cleavage site in the probe (P1) derived strand. Optionally, the target nucleic acid is produced by extension of a target nucleic acid primer that contains the recognition sequence for the first nicking agent. For example, the target nucleic acid may be a single-stranded cDNA produced by reverse transcription of an endogenous single-stranded RNA, wherein the target nucleic acid primer containing the recognition sequence for the first nicking agent is the primer for the reverse transcription. In this embodiment, separation of the complementary RNA target following extension of the target nucleic acid primer may be accomplished by RNase H degradation of the RNA, or temperature denaturation. Alternatively, the target nucleic acid may be a single-stranded DNA produced by polymerase copying of an endogenous DNA sequence, wherein the target nucleic acid primer containing the recognition sequence for the first nicking agent is the primer for the polymerase. In this embodiment, separation of the complementary DNA target following extension of the target nucleic acid primer may be accomplished by strand displacement using an additional upstream primer.

Figure 2C:
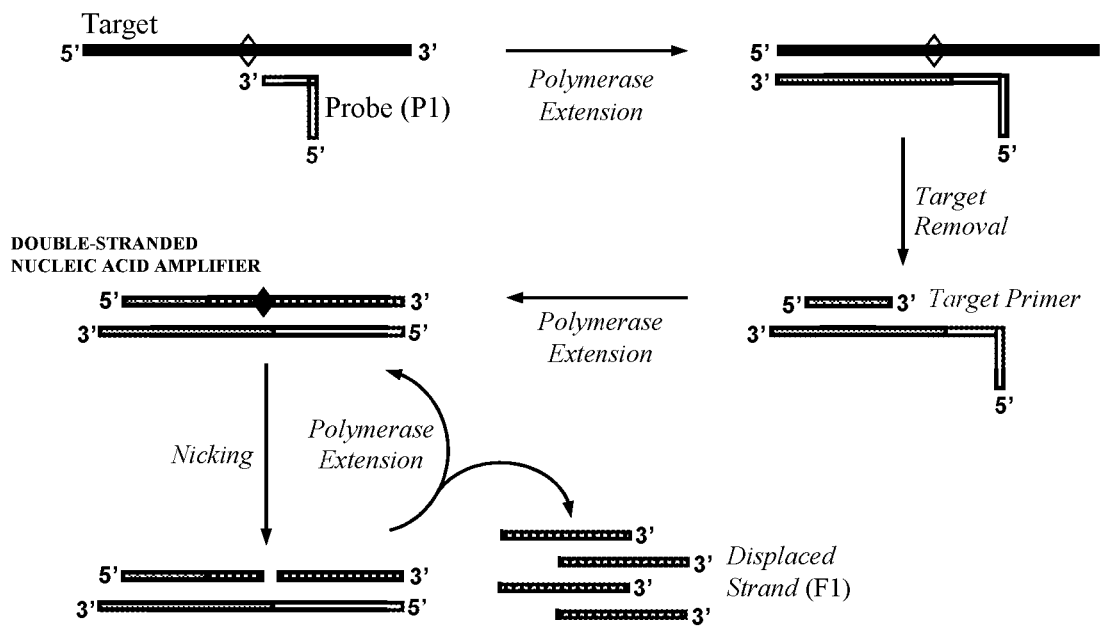
FIG. 2C. Schematic representation of production of a double-stranded nucleic acid amplifier by polymerase extension of oligonucleotide probe (P1) and a target nucleic acid primer.

In another embodiment, illustrated in FIG. 2C, the first oligonucleotide probe (P1) comprises a complementarity region at its 3' end that is capable of sequence specific hybridisation to the target nucleic acid and the sample is also contacted with a target nucleic acid primer; whereby, on hybridization of probe (P1) to the target nucleic acid, extension of (P1) by the polymerase forms a sequence that is complementary to the cleavage site of the first nicking agent; the target nucleic acid strand is separated from the extended probe (P1) derived strand; the target nucleic acid primer then hybridises to the probe (P1) derived strand and the polymerase extends the target nucleic acid primer to produce the double-stranded nucleic acid amplifier.

Figure 2D:
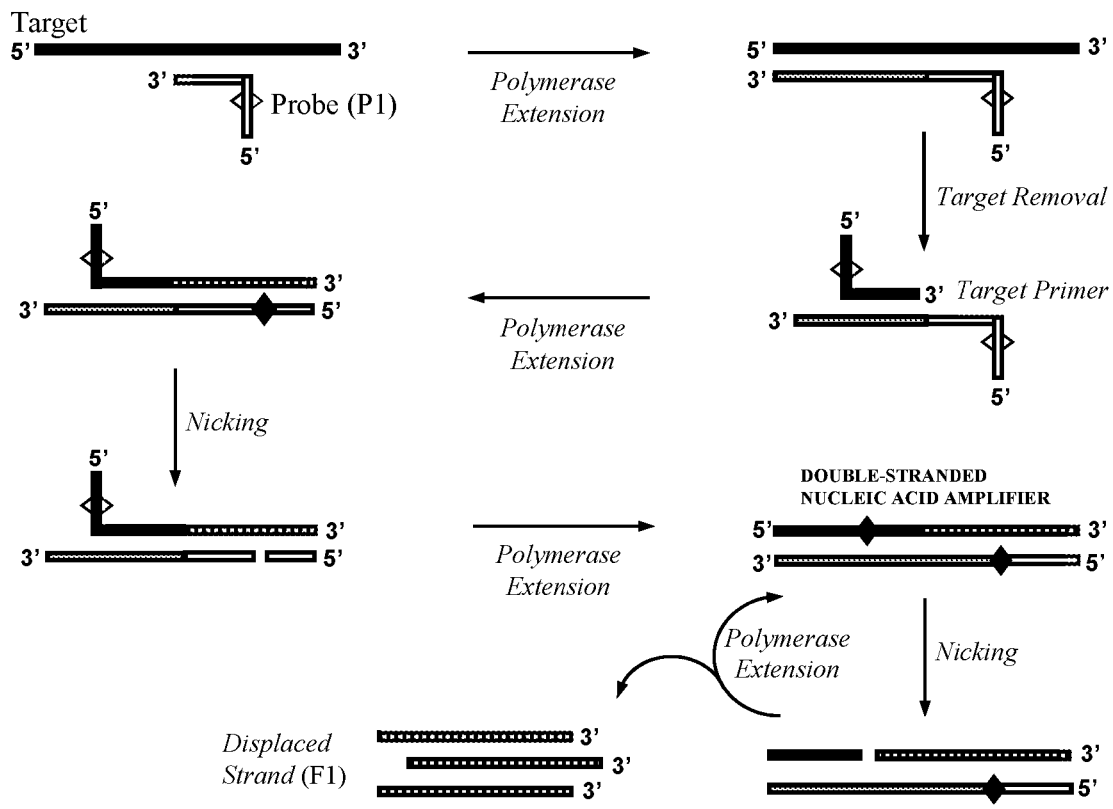
FIG. 2D. Schematic representation of production of a double-stranded nucleic acid amplifier that contains one or more cleavage site in the target derived strand and one or more cleavage site in the probe (P1) derived strand, wherein the target nucleic acid is single-stranded RNA.

In a further embodiment illustrated in FIG. 2D, the first oligonucleotide probe (P1) comprises the recognition sequence for a probe (P1) nicking agent and comprises a complementarity region at its 3' end that is capable of sequence specific hybridisation to the target nucleic acid and the sample is also contacted with a target nucleic acid primer that contains the recognition sequence for the first nicking agent; whereby, following hybridisation of probe (P1) to the target nucleic acid, extension of (P1) by the polymerase forms a sequence that is capable of sequence specific hybridisation to the 3' end of the target nucleic acid primer; the target nucleic acid strand is separated from the extended probe (P1) derived strand; the target nucleic acid primer then hybridises to the probe (P1) derived strand and the polymerase extends the target nucleic acid primer to produce a double-stranded nucleic acid containing a cleavage site for the probe (P1) nicking agent in the probe (P1) derived strand. Following production of said double-stranded nucleic acid: (X) the probe (P1) nicking agent specifically recognises the double-stranded nucleic acid and cleaves the (P1) derived strand of said double-stranded nucleic acid at said cleavage site to produce a primer that remains hybridised to the target derived strand; and (Y) the polymerase extends said primer to produce the double-stranded nucleic acid amplifier which is cleaved in step a) (A).

The embodiments illustrated in FIG. 2C and FIG. 2D may be employed, for example, in the event the target nucleic acid is RNA and the DNA/RNA hybrid sequence formed following extension of (P1) by the polymerase, which may be a reverse transcriptase, does not produce a nicking agent cleavage site within the target nucleic acid strand because the first nicking agent is not capable of functioning with DNA/RNA hybrid sequences. In this situation, separation of the complementary RNA target following extension of (P1) may be accomplished by RNase H degradation of the RNA, or temperature denaturation, or strand displacement, for example. The target nucleic acid primer contains a portion, typically 10-30 bases, of the same or similar sequence as a region of the target nucleic acid at its 3' end such that it is capable of sequence specific hybridisation to the (P1) strand produced after (P1) has been extended by the polymerase and is thereafter capable of itself being extended by a polymerase. In a further embodiment there is no requirement for the target nucleic acid primer to contain the cleavage site for the first nicking agent.

Figure 2E:
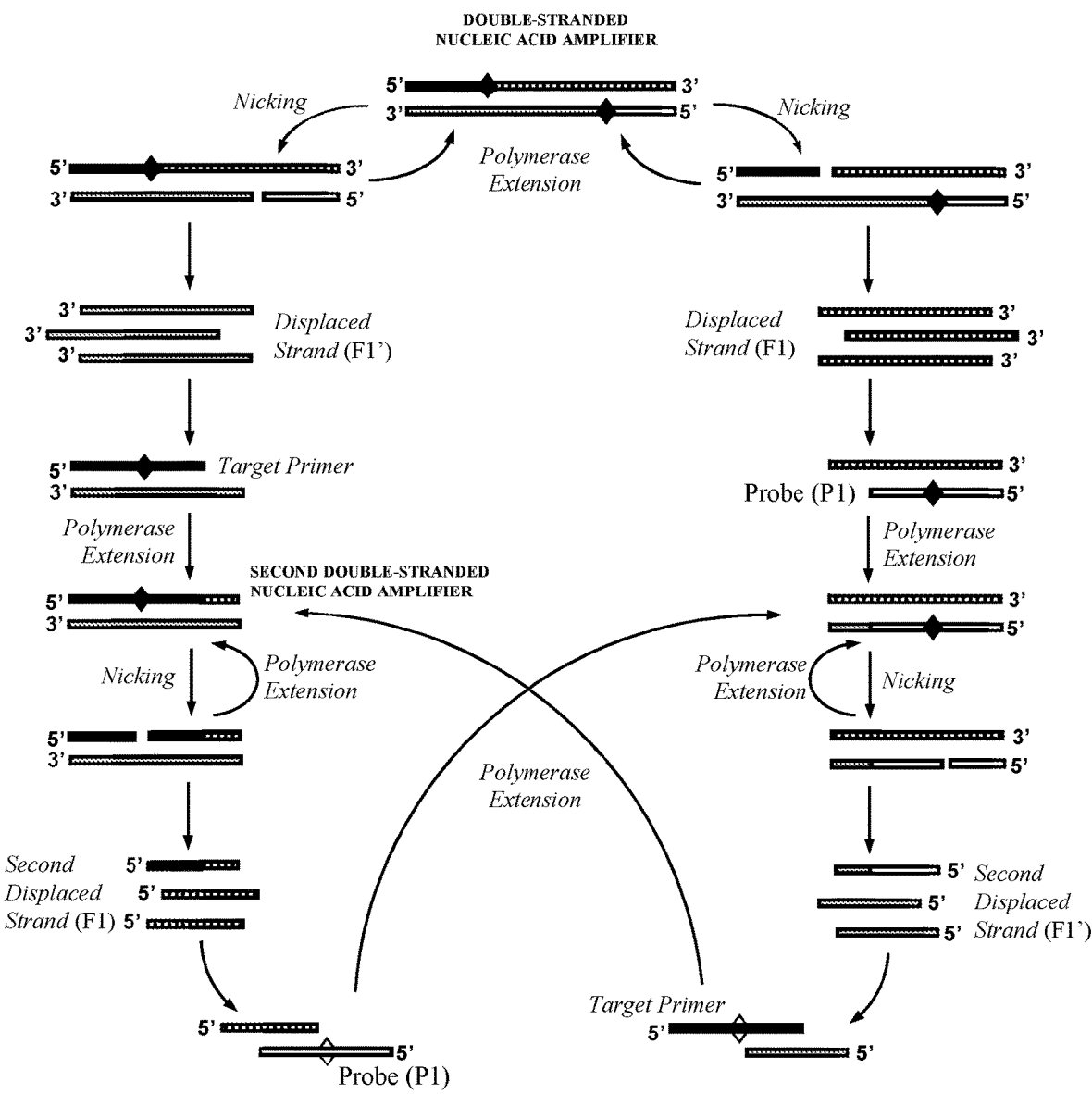
FIG. 2E. Schematic representation of the cycling amplification process that occurs in step a) when the target nucleic acid primer contains the recognition sequence for the first nicking agent and probe (P1) contains the recognition sequence for a probe (P1) nicking agent.

Embodiments of the invention wherein the double-stranded nucleic acid amplifier which is cleaved in step a) (A), contains two or more nicking agent cleavage sites, one or more cleavage site in the target derived strand and one or more cleavage site in the probe (P1) derived strand, illustrated in FIGS. 2B and 2D, have potential for additional amplification in step a). In an embodiment wherein a target nucleic acid primer contains the recognition sequence for the first nicking agent and probe (P1) contains the recognition sequence for a probe (P1) nicking agent, a cycling process occurs as illustrated in FIG. 2E resulting in additional amplification in step a) as described below:

i) The double-stranded nucleic acid amplifier displaces a first target derived strand fragment (F1) that is 3' of the cleavage site in the target derived strand and also displaces a first probe (P1) derived strand fragment (F1') that is 3' of the cleavage site in the probe (P1) derived strand.

ii) (F1') comprises a complementarity region capable of sequence specific hybridisation to the target nucleic acid primer to produce a cleavage site for the first nicking agent in the target nucleic acid primer; whereby the first nicking agent specifically recognises the double-stranded nucleic acid formed when (F1') hybridises to the target nucleic acid primer and cleaves the target nucleic acid primer to produce a primer that remains hybridised to fragment (F1'); and the polymerase extends said primer to produce a second double-stranded nucleic acid amplifier. In one embodiment the second double-stranded nucleic acid amplifier is the double-stranded nucleic acid amplifier which is cleaved in step a) (A). Following production of the second double-stranded nucleic acid amplifier: (x) the first nicking agent specifically recognises said second double-stranded nucleic acid amplifier and cleaves the target derived strand of said second double-stranded nucleic acid amplifier at said cleavage site to produce a primer that remains hybridised to the target derived strand; and (y) the polymerase extends said primer to reproduce said second double-stranded nucleic acid amplifier and displaces a second target derived strand fragment (F1) that is 3' of said cleavage site.

iii) The first target derived strand fragment (F1) comprises a complementarity region capable of sequence specific hybridisation to probe (P1) to produce a cleavage site for the probe (P1) nicking agent in probe (P1); whereby the probe (P1) nicking agent specifically recognises the double-stranded nucleic acid formed when (F1) hybridises to probe (P1) and cleaves probe (P1) to produce a primer that remains hybridised to fragment (F1); and the polymerase extends said primer to produce an extended double-stranded nucleic acid; and whereby following production of said extended double-stranded nucleic acid: (x) the probe (P1) nicking agent specifically recognises said extended double-stranded nucleic acid and cleaves the (P1) derived strand of said extended double-stranded nucleic acid at said cleavage site to produce a primer that remains hybridised to the target derived strand; and (y) the polymerase extends said primer to reproduce said extended double-stranded nucleic acid and displaces a second probe (P1) derived strand fragment (F1') that is 3' of said cleavage site.

iv) The second target derived strand fragment (F1) comprises a complementarity region at its 3' end that is capable of sequence specific hybridisation to probe (P1); whereby, following hybridisation of said second target derived strand fragment (F1) to probe (P1), the polymerase extends both probe (P1) and said second target derived strand fragment (F1) to produce the extended double stranded nucleic acid described in (iii) above.

v) The second probe (P1) derived strand fragment (F1') comprises a complementarity region at its 3' end that is capable of sequence specific hybridisation to the target primer; whereby, following hybridisation of said second probe (P1) derived strand fragment (F1') to the target primer, the polymerase extends both the target primer and said second probe (P1) derived strand fragment (F1') to produce the second double stranded nucleic acid amplifier.

vi) The first target derived strand fragment (F1) and/or the second target derived strand fragment (F1) are produced exponentially in step a) of the method and in each case either hybridise to probe (P1) leading to production of additional copies of (F1) through the cyclical process illustrated in FIG. 2E, or hybridise to probe (P2) in step b) of the method.

The probe (P1) nicking agent used in various embodiments of the invention optionally is the same as the first and/or second nicking agent.

Embodiments comprising a target nucleic acid primer that contains the recognition sequence for the first nicking agent and a probe (P1) that contains the recognition sequence for a probe (P1) nicking agent, have potential for additional amplification in step a) which can provide for more sensitive detection of the target nucleic acid. Furthermore, specificity is typically enhanced due to the requirement for sequence specific hybridisation of both probe (P1) and the target primer and the further requirement for the reverse complement of the recognition sequence of the second nicking agent to be present in the target derived strand so it can be displaced in fragment (F1) for hybridisation to probe (P2) in step b). Typically, for the detection of an endogenous target using such embodiments, the presence of a nicking agent recognition sequence within an endogenous target sequence is used to identify the appropriate sequence regions for hybridisation of probe (P1) and the target nucleic acid primer, such that the reverse complement to the second nicking agent recognition sequence is comprised in fragment (F1). The strand of an endogenous target sequence that contains the reverse complement of the recognition sequence for the second nicking agent forms the target nucleic acid strand for the method. A single-stranded endogenous target may either form the target nucleic acid for the method as illustrated in FIG. 2D, or alternatively may be converted to the target nucleic acid by extension of the target nucleic acid primer as illustrated in FIG. 2B. Thus any recognition sequence for the second nicking agent present within the endogenous target can be selected for use in the method regardless of which strand is cleaved by the second nicking agent at the cleavage site in respect of that recognition sequence. An embodiment of the invention therefore consists of the following:

A method for detecting the presence of a target nucleic acid of defined sequence in a sample which method comprises the steps of:

a) contacting said sample with:
   i. a first nicking agent;
   ii. a target nucleic acid primer that contains a complementary region at its 3' end that has the same sequence as a region of the target nucleic acid and contains the recognition sequence for the first nicking agent;
   iii. a first oligonucleotide probe (P1) that contains a complementarity region at its 3' end that is capable of sequence specific hybridisation to the target nucleic acid and contains the recognition sequence for a probe (P1) nicking agent;
   iv. a probe (P1) nicking agent; and
   v. a polymerase.

to produce in the presence of the target nucleic acid a double-stranded nucleic acid amplifier comprising a target derived strand containing at least one cleavage site for the first nicking agent and a probe (P1) derived strand containing at least one cleavage site for the probe (P1) nicking agent; whereby, either:

I. following hybridisation of probe (P1) to the target nucleic acid, extension of probe (P1) by the polymerase forms a double-stranded nucleic acid that contains the cleavage site for the first nicking agent within the target nucleic acid strand; and whereby the first nicking agent specifically recognises said double-stranded nucleic acid and cleaves said target nucleic acid strand to produce a primer that remains hybridised to the probe (P1) derived strand; and the polymerase extends the primer to produce said double-stranded nucleic acid amplifier; or II. following hybridisation of probe (P1) to the target nucleic acid, extension of (P1) by the polymerase forms a sequence that is capable of sequence specific hybridisation to the 3' end of the target nucleic acid primer; the target nucleic acid strand is separated from the probe (P1) derived strand; the target nucleic acid primer then hybridises to the probe (P1) derived strand and the polymerase extends the target nucleic acid primer to produce a double-stranded nucleic acid containing a cleavage site for the probe (P1) nicking agent in the probe (P1) derived strand, wherein following production of said double-stranded nucleic acid: (x) the probe (P1) nicking agent specifically recognises the double-stranded nucleic acid and cleaves the (P1) derived strand of said double-stranded nucleic acid at said cleavage site to produce a primer that remains hybridised to the target derived strand; and (y) the polymerase extends said primer to produce said double-stranded nucleic acid amplifier;

and, whereby following production of the double-stranded nucleic acid amplifier: (A) the first nicking agent specifically recognises the double-stranded nucleic acid amplifier and cleaves the target derived strand of the double-stranded nucleic acid amplifier at said cleavage site to produce a primer that remains hybridised to the probe (P1) derived strand; and (B) the polymerase extends said primer to reproduce said double-stranded nucleic acid amplifier and displaces the target derived strand fragment (F1) that is 3' of said cleavage site;

b) contacting the fragment (F1) produced in step a) with:
   i. a second oligonucleotide probe (P2); and
   ii. a second nicking agent;

wherein the second oligonucleotide probe (P2) comprises a complementarity region capable of sequence specific hybridisation to fragment (F1) which following hybridisation to fragment (F1) produces a cleavage site for the second nicking agent; whereby the second nicking agent specifically recognises the double-stranded nucleic acid formed when the second oligonucleotide probe (P2) hybridises to fragment (F1) and cleaves said second oligonucleotide probe (P2) to produce a probe fragment (F2); and c) detecting the presence of the probe fragment (F2) produced in step b) wherein the presence of said detected probe fragment (F2) indicates the presence of the target nucleic acid in said sample.

In said embodiment, the cycling amplification process illustrated in FIG. 2E also occurs in step a) following the following the production of the double-stranded nucleic acid amplifier. Thus each fragment (F1) produced either hybridises to probe (P2) in step b) of the method or hybridises to probe (P1) leading to the generation of further copies of fragment (F1) and the second fragment (F1) through the cycling amplification process. An intrisic aspect of the cycling amplification process that occurs following production of the double-stranded nucleic acid amplifier is that a functionally equivalent process occurs on both strands. Thus, the probe (P1) nicking agent cleavage site in the double-stranded nucleic acid amplifier is cleaved by the probe (P1) nicking agent to produce a primer that remains hybridised to the target derived strand; and the polymerase extends said primer to reproduce said double-stranded nucleic acid amplifier and displaces the target derived strand fragment (F1') that is 3' of said cleavage site. A cyclical exponential amplification process occurs as illustrated in FIG. 2E.

In various embodiments the target derived strand fragment (F1) comprises a complementarity region at its 3' end that is capable of sequence specific hybridisation to probe (P1); whereby, on hybridisation of fragment (F1) to probe (P1), extension of (F1) by the polymerase forms a double-stranded nucleic acid that contains the cleavage site for a nicking agent within the target nucleic acid strand. In such embodiments with cross-priming capability, step a) becomes intrinsically an exponential (second order) reaction wherein each target nucleic acid molecule initially produces one double-stranded nucleic acid amplifier, each of which in turn each produces a given number of displaced fragment(s) (F1) in a given period of time; but wherein each displaced fragment is then capable of sequence specific hybridisation to another copy of oligonucleotide probe (P1) present in the reaction to produce, for example, further copies of the double-stranded nucleic acid amplifier.

Since F1 is synthesised by the polymerase using the P1 derived strand as a template, F1 is typically capable of sequence specific hybridisation to oligonucleotide probe (P1) with complementarity at each base position of F1. The property that extension of F1 by the polymerase forms a double-stranded nucleic acid that contains the cleavage site for a nicking agent within the target nucleic acid strand is achieved by (i) F1 having multiple distinct sites at which it is capable of sequence specific hybridisation within oligonucleotide probe (P1) with one or more additional sites to the 5' and/or 3' of the original hybridisation site; and/or (ii) the target derived strand of the double-stranded nucleic acid amplifier contains multiple nicking agent cleavage sites such that multiple oligonucleotide probe fragments are displaced from P1. Accordingly in an embodiment of the invention, the target derived strand of the double-stranded nucleic acid amplifier in step a) (A) contains two or more nicking agent cleavage sites. In an embodiment, P1 contains the necessary sequence at its 5' end such that the target derived strand of the double-stranded nucleic acid amplifier comprises two or more repeats of the same sequence that produce two or more copies of F1 from the same double-stranded nucleic acid amplifier molecule, following cleavage at two or more nicking agent cleavage sites. In other embodiments, the sequence of each displaced oligonucleotide probe fragment produced from the same double-stranded nucleic acid amplifier is varied to achieve the desired properties, such as the ability to hybridise (prime) further oligonucleotide probes and/or to lead to the optimal performance of steps b) and c) of the method. Furthermore, two or more nicking agents each of which determines the 5' end of a displaced fragment may be used by including the necessary complementary sequence of the relevant recognition sequences within oligonucleotide probe (P1).

An integral aspect of the method is the use of one or more nicking agent(s) and one or more polymerase.

A "nicking agent" refers to any means, chemical, biological or physical, which cleaves or preferentially cleaves the phosphodiester bond on a single strand of two duplexed or double-stranded nucleic acid molecules at an intended target site. A number of embodiments of the present invention employ a class of enzyme known as nicking endonucleases or nicking restriction endonucleases, which may be a naturally occurring enzyme or an engineered enzyme such as a mutated form of a naturally occurring enzyme or a DNAzyme. Such enzymes specifically recognise a particular recognition sequence within a double-stranded nucleic acid and cleave only one strand of the nucleic acid duplex at a particular cleavage site leaving the other strand intact.

A "double-strand cleaving agent" or "double-stranded cleaving agent" refers to any means, chemical, biological or physical which cleaves the phosphodiester bond on both strands of two duplexed or double-stranded nucleic acid molecules at an intended target site. Double-strand cleaving agents include double strand cleaving restriction enzymes or restriction endonucleases, a broad class of enzyme capable of recognising a particular recognition sequence within a double-stranded nucleic acid and cleaving both strands of the nucleic acid duplex at particular cleavage sites. A large number of restriction enzymes are available covering a wide range of recognition sequences. Such restriction enzymes, despite being capable of cleaving both strands of a double-stranded nucleic acid, can in certain circumstances also function as nicking agents and be employed as nicking agents for the performance of the invention in a number of ways, including the following:

(a) Certain double-strand cleaving restriction enzymes have a preference (increased rate) for the cleavage of one strand of a double-stranded nucleic acid over the other strand and therefore are capable of binding to a double-stranded nucleic acid and cleaving only one of the strands and thus acting as a nicking agent, at least for a certain proportion of binding/cleavage events. For example, the double-strand cleaving restriction endonuclease FokI has such a "strand preference" for cleavage of the bottom strand of its recognition site, whilst the double-strand cleaving restriction endonuclease BbsI has a strong preference for cleavage of the top strand of its recognition site (Example 3.10, FIG. 12A and FIG. 12B).

(b) One of the strands within the double-stranded nucleic acid at the recognition and cleavage site is not capable of being cleaved by said restriction enzyme. This can be accomplished in a number of ways, including the following.

i) One of the two nucleic acid strands in the duplexed nucleic acid target consists of a sequence that terminates prior to, and therefore does not contain, the phosphodiester bond that would be capable of being cleaved by the enzyme. Such nucleic acid strand whose sequence terminates one side of the known phosphodiester cleavage site for said enzyme may be referred to as a 'truncated template'. For example, Example 3.10 (FIG. 12C) demonstrates that the double-strand cleaving restriction endonuclease BccI can act as a nicking agent using a truncated template, as illustrated below:

BccI Restriction Site (recognition sequence in
bold; cut sites shown by triangles):
5'-ATTAATACCATCAAAA▼TGTATATAT-3'

3'-TAATTATGGTAGTTTTA▲TATATA-5'

BccI as a Nicking Agent (truncated template is not
cleaved)
5'-ATTAATACCATCAAAA▼TGTATATAT-3'

Truncated Template
3'-TAATTATGGTAGTTTTA-5' ii) Double-strand cleaving restriction enzymes are typically able to act as nicking agents if one strand of the double-stranded nucleic acid target site is modified such that the phosphodiester bond of the cleavage site on one of the strands is protected using a nuclease resistant modification, such as a phosphorothioate (PTO), boranophosphate, methylphosphate or peptide internucleotide linkage. Certain modified internucleotide linkages, e.g. PTO linkages, can be chemically synthesised within oligonucleotides probes and primers or integrated into a double-stranded nucleic acid by a polymerase, such as by using one or more alpha thiol modified deoxynucleotide. For example, Example 3.10 (FIG. 12A-C) demonstrates the use of enzymes FokI, BbsI and BccI as nicking agents with PTO linkages.

Due to the very large number of double-strand cleaving agents, with over 3,000 reported and over 600 commercially available, the ability to use double-strand cleaving agents as nicking agents in the method overcomes the sequence space limitations of known methods that are only performed with nicking endonucleases, and therefore enables restriction enzyme binding sites of a wider range of target sites to be identified. The present invention enables a broad range of such double-strand cleaving agents to be employed as a nicking agent. Certain enzyme classes may be prioritised based on the particular embodiment and/or the target nucleic acid sequence. Typically, double-strand cleaving agents which recognise a palindromic recognition sequence are deprioritised because when such a recognition sequence is contained in an oligonucleotide probe, the double-stranded nucleic acid sequence that is specifically recognised by said palidromic double-strand cleaving agent can be produced by such probe hybridising to itself. "Assymetric" restriction endonucleases with a non-palindromic recognition sequence that cleave outside of their restriction site are ideally suited for use in the present invention particularly when used with a truncated template. Partial or degenerate palindromic sequence recognising restriction endonucleases that cleave within their recognition site may also be used as nicking agents through use of a truncated template. Strand preference is typically more pronounced for assymetric restriction endonucleases than for palidromes. Nuclease resistant nucleotide linkage modifications, e.g. PTO, may be used to block the cleavage of either strand of a wide range of commercially available double-strand cleaving agents of various different classes, including type IIS and type IIG restriction endonucleases with both partial or degenerate palindromic and asymmetric restriction recognition sequences, in order to enable their use as nicking agents in the methods of the invention.

Nicking agent(s) are typically employed in the relevant steps of the method in an amount of 0.1-100 Units, where one unit is defined as the amount of agent required to digest 1 μg T7 DNA in 1 hour at a given temperature (e.g. 37° C.) in a total reaction volume of 50 μl. However, the amount depends on a number of factors such as the activity of the nicking agent selected, the concentration and form of the nicking agent, the anticipated concentration of the target nucleic acid, the volume of the reaction, the number and concentration of the oligonucleotide probes and the reaction temperature, and should not be considered limiting in any way. Those skilled in the art will understand that a nicking agent such as a restriction enzyme employed in the method will require a suitable buffer and salts, e.g. divalent metal ions, for effective and efficient function, control of pH and stabilisation of the enzyme.

As nicking agents cleave only one strand of the nucleic acid duplex, following cleavage they present an exposed 3' hydroxyl group which can act as an efficient priming site for a polymerase. A polymerase is an enzyme that synthesises chains or polymers of nucleic acids by extending a primer and generating a reverse complementary "copy" of a DNA or RNA template strand using base-pairing interactions. Polymerases include DNA dependent DNA polymerase, RNA dependent DNA polymerase (reverse transcriptase), DNA dependent RNA polymerase and RNA-dependent RNA polymerase. Certain polymerases possess the ability to copy RNA and DNA as the template strand with either an RNA or DNA primer. For example, polymerases from *Bacillus* species or *Thermus* species can frequently possess both DNA dependent DNA polymerase activity as well as RNA dependent DNA polymerase (reverse transcriptase) activity.

Typically, a polymerase with strand displacement capability is employed in the performance of the method in order that, for example, the probe fragment (F1) may be displaced from the double-stranded nucleic acid amplifier for its use in step b) of the method. The term "strand displacement" refers to the ability of a polymerase to displace downstream DNA encountered during synthesis. A range of polymerases with strand displacement capability that operate at different temperatures have been characterised and are commercially available. Phi29 polymerase has a very strong ability to strand displace. Polymerases from *Bacillus* species, such as Bst DNA Polymerase Large Fragment, typically exhibit high strand displacing activity and are well-suited to use in the performance of the method.

Polymerase(s) are typically employed in the relevant steps of the method in an appropriate amount which is optimised dependent on the enzyme and concentration of oligonucleotide probe (P1) and desired temperature of the reaction, for example. For example, of 0.1-100 Units of a *Bacillus* polymerase may be used, where one unit is defined as the amount of enzyme that will incorporate 25 nmol of dNTP into acid insoluble material in 30 minutes at 65° C. However, the amount depends on a number of factors such as the activity of the polymerase, its concentration and form, the anticipated concentration of the target nucleic acid, the volume of the reaction, the number and concentration of the oligonucleotide probes and the reaction temperature, and should not be considered limiting in any way. Those skilled in the art will know that polymerases require dNTP monomers to have polymerase activity and also that they require an appropriate buffer, with components such as buffer salts, divalent ions and stabilising agents. The concentration of dNTP for the method may be optimised for any given enzyme and reagents, in order to maximise activity and minimise ab initio synthesis to avoid background signal generation and "mis-priming" of probe (P1). A wide range of polymerases and nicking agents have been employed in the performance of the method (see Example 3) and suitable buffer conditions are readily identified in which both are active.

According to an embodiment of the invention, two or more of steps a), b) and c) are performed simultaneously.

Steps a), b) and c) may be performed over a wide range of temperatures. Whilst the optimal temperature for each step is determined by the temperature optimum of the relevant polymerase and nicking agent and the melting temperature of the complementarity region(s) of the oligonucleotide probes and the fragments produced following cleavage of said probes, the exponential amplification of the method allows the steps to be performed over a wide temperature range, e.g. 20-60° C.

According to an embodiment of the method, the first nicking agent and the second nicking agent are the same. The probe (P1) nicking agent may also be the same or different from the first and/or second nicking agent(s). For example, the same nicking agent may be used in steps a) and b). Thus according to an embodiment of the invention, the first nicking agent and/or the second nicking agent and/or the probe (P1) nicking agent may be the same.

Our investigations have revealed that the present method is effective over a wide range of target nucleic acid levels including detection down to very low copy numbers.

The potential for intrinsic exponentiality of step a) through cross-priming or the cyclical process illustrated in FIG. 2E, together with the further amplification in step b) through target recycling provides for a strong and rapid exponential signal amplification effect to be obtained in various embodiments of the method. Oligonucleotides probes (P1) and (P2) are typically provided in excess of target nucleic acid. The concentration of P1, typically 0.01-1 pmol, defines how many double-stranded nucleic acid amplifiers may be produced from the target nucleic acid and, where relevant, cross-priming fragments. Various experiments have also revealed that the thermodynamic equilibrium of the polymerase extension, strand displacement and oligonucleotide probe cleavage in the method lie substantially in favour of the reaction end-point, being cleavage of P2 to produce many copies of F2 and can therefore proceed to completion if the rate is sufficient. The oligonucleotide probe (P2) that produces the probe fragment (F2) to be detected in step c) is preferably at a level wherein the number of copies of the probe fragment (F2) produced following cleavage of said oligonucleotide probe (P2) is sufficiently above the limit of detection of the detection method employed to allow said probe fragment (F2) to be readily detected. Typically using polyacrylamide gels with SYBR gold staining we have observed detection of as little as 0.01 pmol of probe fragment (F2) (approximately 6 billion copies). A similar range is observed using detection with a colorimetric moiety, such as gold nanoparticles, although the appropriate level would depend on the detection method to be employed. It would be advantageous to design the method such that neither of the oligonucleotide probes (P1) and (P2) would become exhausted (i.e. all copies cleaved) prior to the probe fragment (F2) detected in step c) reaching a detectable amount. The method may be designed such that oligonucleotide probe (P2) is at a higher level than probe (P1), due to the exponential cascade effect that occurs. However, this needs to be balanced with the possibility that increased concentration of oligonucleotide probe may increase the rate of its cleavage at a given level of target nucleic acid. Thus typically, the first oligonucleotide probe (P1) is present at 0.01-1 pmol and the second oligonucleotide P2 at 0.1-10 pmol, although such ranges should be regarded as non-limiting. The target nucleic acid primer, in certain embodiments, is typically present at a level in the same range as probe (P1), although the ratio of probe (P1) and the target nucleic acid primer would be explored during optimisation of the reaction to enhance the performance of the method.

"Sequence specific hybridisation" refers to the ability of an oligonucleotide probe to bind to a target nucleic acid or a probe fragment by virtue of the hydrogen bond base pairing between complementary bases in the sequence of each nucleic acid. Typical base pairings are Adenine-Thymine (A-T), or Adenine-Uracil in the case of RNA or RNA/DNA hybrid duplexes, and Cytosine-Guanine (C-G), although a range of natural and non-natural analogues of nucleic acid bases are also known with particular binding preferences. In the present invention, the complementarity region of an oligonucleotide probe or primer does not necessarily need to comprise natural nucleic acid bases in a sequence with complete and exact complementarity to the target nucleic acid or relevant probe fragment; rather for the performance of the method the oligonucleotide probes/ primers only need to be capable of sequence specific hybridisation to the target nucleic acid or probe fragment sequence sufficiently to form the double-stranded recognition sequence to produce the cleavage site of the relevant nicking agent to allow cleavage of the target and/or oligonucleotide probe and/or to permit extension by the polymerase employed in the method. Such hybridisation may be possible without exact complementarity, and with non-natural bases or abasic sites. Sequence specific hybridisation is an important factor in the design of oligonucleotide probes to perform specific detection of target nucleic acids, which in certain applications may be present at low copy number and in the presence of a large excess of other nucleic acids. The design of oligonucleotide probes is described in more detail below. Nevertheless, in an embodiment, the complementarity between the complementarity region of the first oligonucleotide probe (P1) and the target nucleic acid is 100%. In other embodiments there are one or more non-complementing base pairs. In some circumstances it may be advantageous to use a mixture of oligonucleotide probes in a given step of the method (or all of them). Thus, by way of example, in the case of a target nucleic acid comprising a single nucleotide polymorphism (SNP) site having two polymorphic positions, a 1:1 mixture of oligonucleotide probes differing in one position (each component having complementarity to the respective base of the SNP) may be employed. During manufacture of oligonucleotides it is routine practice to randomise one or more bases during the synthesis process. Similarly, in an embodiment, the complementarity between the complementarity region of probe fragment (F1) and the complementarity region of probe (P2) to which it is intended to hybridise is 100%. In other embodiments there may be 1 or 2 or more non-complementing base pairs.

The present invention yields exponential production of oligonucleotide probe fragments over time. Exponential signal amplification is an essential property of sensitive nucleic acid detection methods, such as PCR and isothermal methods that have been employed widely in various fields. In polymerase based methods, following separation of the DNA duplex both strands are available to be copied by DNA polymerase thus doubling the starting amount. This theoretical doubling of the signal after each cycle means the method can be employed in highly sensitive detection of very small quantities of nucleic acid material. In step a) of the method comprising a target nucleic acid and a single oligonucleotide probe (P1) (in excess) with no cross-priming capability the reaction proceeds in a directly proportional (first order) fashion in the steady state wherein the amount of probe fragment (F1) formed accumulates in a directly proportional amount over time, until one or more reagent becomes limiting. Through use of a second oligonucleotide probe (P2) in this method, exponential production of the second probe fragment (F2) results. The basis of this is that as the amount of first probe fragment (F1) accumulates over time, the amount of target available for the cleavage of the second oligonucleotide probe (P2) is continually increasing. Due to target recycling of the first probe fragment (F1), the result is an exponential (second order) reaction for production of the second probe fragment (F2). Thus the present invention provides enhanced amplification over known methods.

For sensitive detection, where it is desirable to further enhance the sensitivity of the method, cross-priming is employed in step a) of the method to render intrinsic exponential amplification to that step of the method alone. "Cross-priming" refers to the ability of probe fragment (F1) to hybridise to a further copy of oligonucleotide probe (P1) upstream of a nicking agent cleavage site, such that further downstream fragments may be synthesised and displaced, each in turn producing more copies of the double-stranded nucleic acid amplifier, or a secondary double-stranded nucleic acid amplifier, thus leading to a further enhanced exponential effect. Oligonucleotide probe (P1) may be designed such that two or more nicking agent cleavage sites are introduced into the double-stranded nucleic acid amplifier. For example, 2-20, e.g. 10, cleavage sites could be employed, with the sequence between each cleavage site defining the sequence of the displaced strand (F1). In an array in which 10 repeats of the same sequence are employed, each probe fragment, following its displacement from the double-stranded nucleic acid amplifier may bind to any of the reverse complementary repeat sites on another copy of oligonucleotide probe (P1), before being extended by the polymerase, cleavage by the necessary nicking agent(s) and displacing strands downstream of said fragment. In this way exceptional signal enhancement effect may be readily obtained. The alternative embodiment of the method wherein probe (P1) contains a cleavage site for a probe (P1) nicking agent and wherein a target nucleic acid primer is used that contains the cleavage site for the first nicking agent, also typically has exponential amplification in step a) as a result of the cyclical process illustrated in FIG. 2E. Such process also comprises cross-priming where in the second displaced strand fragment (F1) hybridises to probe (P1) to generate a secondary double-stranded nucleic acid amplifier.

There are a number of considerations for the design of the oligonucleotide probes for performance of the method. The first oligonucleotide probe (P1) must comprise a complementarity region capable of sequence specific hybridisation to the target nucleic acid to produce a double-stranded nucleic acid amplifier containing at least one cleavage site for the first nicking agent in the target-derived strand. Typically said complementarity region is designed to target a nicking agent cleavage site within the target nucleic acid, which brings additional specificity to the method by providing further sequence verification in addition to that derived from the hybridisation of nucleic acids alone. Known methods frequently require two independent primer hybridisation events to derive necessary specificity. Due to the enhanced specificity derived from restriction enzyme binding, the present invention can even perform specific and sensitive detection with only a single probe interacting with the target, thus greatly simplifying assay design. Alternative embodiments that exploit two target-specific probe or primer interactions derive enhanced specificity over known methods by additionally exploiting the restriction enzyme binding site present within the target nucleic acid. Furthermore, improved rigour of sequence verification enables low temperature reactions to be performed without loss of specificity and enables increased multiplexing, where multiple reactions are performed for simultaneous detection of multiple targets.

Typically the relevant nicking agent cleavage site within the target nucleic acid would comprise at least 7 bases for a restriction endonuclease, and probe (P1) may be designed to either target that site within the complementarity region capable of sequence specific hybridisation, or to enable the polymerase to extend over said nicking agent cleavage site. It is not essential that the target nucleic acid contains a nicking agent cleavage site for the method and thus embodiments of the method may also be employed to detect a target solely through its hybridisation to oligonucleotide probe (P1), wherein the nicking agent cleavage site necessary for production of the double-stranded nucleic acid amplifier is derived from the sequence of P1 alone.

The sequence of P1 5' of the complementarity region capable of hybridisation to the target nucleic acid is typically designed, in relevant embodiments of the invention, to contain the desired sequence that integrates the designed number of nicking agent cleavage sites and the reverse complementary sequence to the designed fragments to be displaced from the target derived strand of the resulting double-stranded nucleic acid amplifier. The designed sequence will define the nicking agent(s) to be employed, and the sequence of the probe fragments produced for subsequent hybridisation to oligonucleotide probe (P2) and, where desired, cross-priming to other copies of P1 for enhanced amplification effect. Typically, in such embodiments, P1 will contain one or more chemical modifications, such as a phosphorothioate modification to the nucleic acid backbone, to block the cleavage of P1 by the nicking agent(s) employed. This also permits the use of double-strand cleaving agents as nicking agents for the performance of the methods and is a requirement for steps a) and b) to be performed simultaneously even if nicking endonucleases that are not double-strand cleaving agents are employed in the method.

In any embodiment where there is no requirement for the 3' hydroxyl end of P1 to be extended by a polymerase, the 3' end of P1 may optionally be capped, e.g. through use of a 3' phosphate or C-3 modification during oligonucleotide synthesis, if deemed desirable to reduce any risk of non-specific background amplification.

During probe design it is necessary to define the sequence and length of each complementarity region in order to permit optimal sequence specific hybridisation and disassociation of the fragments produced following oligonucleotide probe cleavage and/or polymerase extension. The target nucleic acid contains the antisense of a recognition sequence and cleavage site for a nicking agent that defines the minimal potential sequence of the first complementarity region of the first oligonucleotide probe. In the event that a double-strand cleaving restriction endonuclease is employed as nicking agent for the cleavage of the second oligonucleotide probe (P2), it is necessary that the sequence of the first oligonucleotide probe (P1) be designed to ensure that the correct strand (top or bottom) is used such that the fragment (F1) provides a truncated template and/or that it contains the sequence that has the highest rate of cleavage in the event the chosen nicking agent exhibits a strand preference. The theoretical melting temperature of the sequence of the displaced fragments from probe (P1) and the cleaved fragments (F2) from probe (P2) are also considered in the context of the likely temperature of the reaction and the nicking agent selected, which is balanced with the improvement to specificity of binding and detection that results as sequence length is increased. Our various investigations have indicated considerable versatility in the design of P1 to be used effectively in the method. We have performed reactions with P1 of up to 100 bases in length. Furthermore, the method has been performed with a circularised P1, which effectively provides an endless chain of repeat units.

Depending on the properties of the particular nicking agent (e.g. temperature activity range and sequence specificity) and target nucleic acid sequence (e.g. % of GC), we would typically expect an optimal P1 length of between 7 and 150 bases. The target nucleic acid is defined as the functional sequence capable of sequence specific hybridisation to the relevant complementarity region of P1, the sequence for the relevant nicking agent cleavage site present in the target nucleic acid to permit cleavage of the target nucleic acid and the sequence of the functional primer that remains hybridised to the probe (P1) derived strand following said cleavage. In embodiments wherein the cleavage site for the first nicking agent is not encoded by the target nucleic acid sequence either through direct hybridisation to P1 or through extension of P1, the target nucleic acid is defined simply as the functional sequence capable of sequence specific hybridisation to the relevant complementarity region of P1.

There is considerable flexibility in the design of the region of oligonucleotide probe (P1) to the 5' of the complementarity region that hybridises to the target and of the sequence of oligonucleotide probe (P2). This is because the nicking agent(s) other than any site present in the target nucleic acid may be selected without any limitation of the target nucleic acid sequence. The overall size of the probes and the size and sequence of any spacers and non-complementary sequences may be optimised to ensure the reaction proceeds efficiently. Advantageously said region of P1 and the second oligonucleotide probe (P2) and relevant nicking agents used and any additional methods used for detection of F2 in step c), once they have been optimised, can form a "universal amplification and detection system" which can be applied to the detection of any target by replacing only the target binding complementarity region of the first oligonucleotide probe (P1). This is particularly advantageous for the application of the present invention as the oligonucleotide probes, e.g. P2, and associated detection reagents only need to be optimised once and can then be manufactured in bulk for multiple applications. Oligonucleotide probes for use in the method would typically comprise nucleic acid (e.g. DNA) of standard base composition. However, use of non-natural bases or abasic sites may provide greater flexibility in probe design in certain embodiments. A number of alternative variants of the nucleic acid (e.g. DNA) backbone are also available for use in synthetic oligonucleotide probes, such as phosphorothioate oligos, boranophosphate, methylphosphate or peptide internucleotide linkages. Such modified backbones can be resistant to nuclease cleavage and therefore would allow double-strand cleaving agents to be employed as nicking agents in the method. The first fragment (F1) may also comprise a truncated template sequence that permits the use of double-strand cleaving agents (e.g. restriction endonucleases) as nicking agents. Alternatively, introduction of scissile linkage(s) within the backbone at a particular cleavage site, may permit use of other enzymes, e.g. RNaseH, in the performance of the method.

In various embodiments wherein a target nucleic acid primer is employed that contains the recognition sequence for the first nicking agent and wherein probe (P1) contains the recognition sequence for a probe (P1) nicking agent, as illustrated in FIG. 2B or 2D with cycling amplification process in step a) as illustrated in FIG. 2E, it is necessary to design both probe (P1) and a target nucleic acid primer. Probe (P1) and the target primer would each comprise: (i) a 3' hydroxyl group capable of polymerase extension; (ii) a complementarity region, typically of 10-25 bases in length, at the 3' end that is capable of efficient sequence specific hybridisation at the intended incubation temperature to the target nucleic acid strand, in the case of P1, or to the reverse complement of the target nucleic acid strand, in the case of the target primer; (iii) a recognition sequence for the first nicking agent, in the case of the target primer, or the probe (P1) nicking agent, in the case of probe (P1), which nicking agent recognition sequence is typically immediately upstream of said complementarity region; and (iv) a further sequence upstream that forms the stable primer produced following cleavage by the first nicking agent, in the case of the target primer, or the probe (P1) nicking agent, in the case of probe (P1). Probe (P1) and the target nucleic acid primer do not typically contain phosphorothioate bases. In order to use double-strand cleaving agents as the first, second and/or probe (P1) nicking agent(s), phosphorothioate linkage(s) can be integrated into the double-stranded nucleic acid produced in step a) by the polymerase using one or more alpha thiol modified deoxynucleotide, or an equivalent nucleotide derivative, e.g. Borano. Typically, a single modified nucleotide would be used (e.g. alpha-thiol dTTP) in combination with unmodified variants of the other three nucleotides (dATP, dCTP and dGTP). The 3' complementarity region of probe (P1) and the target nucleic acid primer are designed such that a phosphorothioate linkage is integrated at the internucleotide position necessary to block cleavage of the strand that is reverse complementary to probe (P1) or the target nucleic acid primer, such that one strand of the double-stranded nucleic acid that is specifically recognised by the relevant double-strand cleaving agent is rendered resistant to cleavage by said double-stranded cleaving agent. Furthermore, in embodiments where steps a) and b) are performed simultaneously and the second nicking agent is a double-strand cleaving agent, it may be preferable to use the appropriate modified nucleotide base such that the cleavage site for such double-strand cleaving agent in one or both of the strands is rendered resistant to cleavage in order to improve the efficiency of the cycling amplification process illustrated in FIG. 2E and to allow said double-stranded cleaving agent to act as a nicking agent in step b) of the method.

Detection of an "end-point" probe fragment (F2) which is not capable of sequence specific hybridisation to any complementarity region of any of the oligonucleotide probes, offers advantages over a "closed-loop" system wherein all of the detected probe fragments are capable of sequence specific hybridisation to one or more of the oligonucleotide probes, since it avoids competitive binding for that probe fragment, which reduces the efficiency of the method and hampers detection of that probe fragment. Furthermore, there is no requirement to generate "functional equivalent" copies of the target nucleic acid in the method, such as occurs in PCR, NEAR and other methods, since the intended application is not to amplify the target, but rather to detect its presence in a sample.

For optimal practice of the invention it may be beneficial to separate the oligonucleotide probe (P1) from fragment (F1) such that it does not compete for hybridisation to the fragment (F1) during step b). Furthermore, the oligonucleotide probe fragment (F2) and not the uncleaved oligonucleotide probe (P2) should form the basis of detection in step c). There are a number of ways in which the separation of probe fragments from the respective oligonucleotide probe can be achieved. In various embodiments of the method, therefore, one or more of the oligonucleotide probes is attached to a solid material. In an embodiment the second oligonucleotide probe (P2) is attached to a solid material or to a moiety that permits its attachment to a solid material. In other embodiments, the probe fragment (F2) produced from the oligonucleotide probe (P2) is separated from said oligonucleotide probe (P2) on the basis of its physicochemical properties, such as its size, sequence or charge, prior to the performance of the relevant step.

In embodiments of the method wherein one or more of the oligonucleotide probes is attached to a solid material during the performance of the method, the solid material to which an oligonucleotide probe is attached can be readily separated from the aqueous phase and, if relevant, from the solid material to which another oligonucleotide probe is attached. Attachment of P1 may be performed such that, following its displacement probe fragment (F1) is released from the solid material into the aqueous phase and thus becomes available for sequence specific hybridisation to probe (P2). Attachment of P2 may be performed such that, following cleavage of the oligonucleotide probe (P2) attached to the solid material, the probe fragment (F2) produced is released from the solid material into the aqueous phase and thus becomes available for detection in step c). Uncleaved oligonucleotide probes and hybridised probe fragments remain attached to the solid material and therefore are less likely to cause interference to performance of the method. Release of probe fragment (F2) into the aqueous phase greatly facilitates its detection in step c) to determine the presence of target nucleic acid in a sample, because differential detection from other oligonucleotides, which remain attached to the solid material, is not required. In an embodiment of the method where separate steps a), b) and/or c) are performed sequentially, release of probe fragment into the aqueous phase ensures only the probe fragment, and not the respective uncleaved oligonucleotide probe, is transferred to the subsequent step if only the aqueous phase is transferred between reactions.

It is possible to covalently attach one or both of the oligonucleotide probes to a variety of solid materials for the performance of the method. A number of different solid materials are available which have or can be attached or functionalised with a sufficient density of functional groups in order to be useful for the purpose of attaching or reacting with appropriately modified oligonucleotide probes. Further, a wide range of shapes, sizes and forms of such solid materials are available, including beads, resins, surface-coated plates, slides and capillaries. Examples of such solid materials used for covalent attachment of oligonucleotides include, without limitation: glass slides, glass beads, ferrite core polymer-coated magnetic microbeads, silica microparticles or magnetic silica micro-particles, silica-based capillary microtubes, 3D-reactive polymer slides, microplate wells, polystyrene beads, poly(lactic) acid (PLA) particles, poly(methyl methacrylate) (MA) micro-particles, controlled pore glass resins, graphene oxide surfaces, and functionalised agarose or polyacrylamide surfaces. Polymers such as polyacrylamide have the further advantage that a functionalised oligonucleotide can be covalently attached during the polymerisation reaction between monomers (e.g. acrylamide monomers) that is used to produce the polymer. A functionalised oligonucleotide is included in the polymerisation reaction to produce a solid polymer containing covalently attached oligonucleotide. Such polymerisation represents a highly efficient means of attaching oligonucleotide to a solid material with control over the size, shape and form of the oligonucleotide-attached solid material produced.

Typically in order to attach an oligonucleotide probe to any such solid materials, the oligonucleotide is synthesised with a functional group at either the 3' or 5' end; although functional groups may also be added during the oligonucleotide production process at almost any base position. A specific reaction may then be performed between the functional group(s) within an oligonucleotide and a functional group on the relevant solid material to form a stable covalent bond, resulting in an oligonucleotide attached to a solid material. Typically such an oligonucleotide would be attached to the solid material by either the 5' or 3' end. Two commonly used and reliable attachment chemistries utilise a thiol (SH), or amine ($NH_3$) group and the functional group in the oligonucleotide. A thiol group can react with a maleimide moiety on the solid support to form a thioester linkage, while an amine can react with a succinimidyl ester (NHS ester) modified carboxylic acid to form an amide linkage. A number of other chemistries can also be used, including, without limitation: (i) reaction of an amine group with an epoxide group to form an epoxyamine bond; (ii) reaction of a terminal hydrazide group on an oligonucleotide with an aldehyde, epoxide or ketone group on the solid surface to form a hydrazone bond; (iii) reaction of a alkyne group with an azide moiety to form a 1,2,3-triazole linkage via a click reaction; (iv) reaction of a tosyl group with a thiol or amine group to form an amine bond, and (v) the Solulink™ proprietary reaction chemistry between an aromatic aldehyde (4FB) and an aromatic hydrazine-modified (HyNic) amine group to form a bis aryl hydrazone covalent bond Amine modified glass surfaces, either pre modified or induced by silanization, can be utilized by reaction of the amine group with a succinimidyl ester (NHS ester), isothiocynate, or sulfonyl chloride to form an amino reactive intermediate. This group can then react with a terminal amine group on an oligo, or a thiol group if using a succinimidyl ester with a maleimide moiety on the opposite end such as N-Succinimidyl 4-(maleimidomethyl)cyclohexanecarboxylate (SMCC) or 4-(4-Maleimidophenyl)butyric acid N-hydroxysuccinimide ester (SMPB), to form a stable covalent linkages.

As well as chemical conjugation of an oligonucleotide probe to a solid material, it is possible and potentially advantageous to directly synthesise oligonucleotide probes on a solid material for use in the performance of the method. This again can be achieved by a number of methods including but not limited to techniques such as standard phosphoramidite chemistry for oligonucleotide synthesis on a solid material with a chemical linker attached to the solid material that is not broken by standard deprotection steps used in this methodology of oligonucleotide synthesis. Alternatively photolithography, a process commonly applied in microarray fabrication, can also be used to synthesise oligonucleotides directly onto a solid material.

In other embodiments one or more of the oligonucleotide probes is attached to a moiety that permits attachment of said oligonucleotide probe to a solid material. One strategy is to employ a method of affinity binding whereby a moiety that permits specific binding may be attached to the oligonucleotide probe such that the probe fragment either contains or does not contain said moiety, which thus enables differential separation of the probe fragment from the respective oligonucleotide probe to be performed. This may be performed, for example, using antibody-antigen binding or an affinity tag, such as a poly-histidine tag, or by using nucleic acid based hybridisation. An exemplary such moiety is biotin, which is capable of high affinity binding to streptavidin or avidin which itself is attached to beads or another solid surface. In one embodiment of the invention, step b) may be performed with aqueous biotinylated oligonucleotide probe (P2) before an excess of streptavidin coated beads is added to the reaction. A biotin moiety present on the oligonucleotide probe but not probe fragment causes the full length oligonucleotide probe and remaining fragment to become attached to the beads. The beads are subsequently removed from the reaction, using centrifugation, or a magnet in the case of magnetic beads, and the presence of the probe fragment (F2) can be detected in the aqueous phase.

In other embodiments, the probe fragment (F2) produced from the oligonucleotide probe P2 in step b), is separated from said oligonucleotide probe on the basis of its physicochemical properties, such as its size, sequence or charge, prior to its detection in step c). For example, any form of separation based on physicochemical properties such as size, sequence or charge of the smaller probe fragment from the larger oligonucleotide probe may be employed. Examples of techniques capable of separation of unmodified nucleic acids include, without limitation, capillary electrophoresis, gel electrophoresis, ion exchange, gel filtration, high performance liquid chromatography, dialysis and membrane filtration. Further the sequence difference between the probe fragment and the respective oligonucleotide probe, may be exploited for separation using differential hybridisation of the two species to complementary probes.

While it is envisaged that any nicking agent capable of cleaving the phosphodiester bond on a single strand of two duplexed nucleic acid molecules at an intended target site could feasibly be used in the performance of the method, nicking endonucleases are particularly well suited to the task. Nicking endonucleases are a subtype of type II restriction endonuclease enzymes that can catalyse the hydrolysis of the phosphodiester bond in the backbone of DNA molecules in a sequence specific manner. Double-strand cleaving restriction endonucleases, of which a much larger number are available, can also be readily employed as nicking agents for use in the performance of the method, as described herein, providing a large number of enzymes from which to select the optimal nicking agent for a given target site and to optimise the parameters of the method (e.g. temperature and time). A number of other alternative types of enzyme could potentially be used or engineered to be suitable for performance of the method, such as, for example, a programmable nicking enzyme. One skilled in the art will recognise that a number of such programmable enzymes that are encoded by bacterial CRISPR-associated genes or 'Cas genes' and could potentially be exploited to specifically target any desired sequence through the use of a guide RNA sequence (Hsu et al. (2014) Cell 157, 1262). The CRISPR\Cas system, originally discovered as a conserved form of a prokaryotic immunity, is currently being employed in a number of areas of biotechnology for the purpose of precisely targeting DNA and RNA nucleic acid sequences for site specific cleavage, usually but not exclusively for the purpose of gene editing (Sander et al. (2014) Nature Biotechnology 32, 347). The programmable nature of these enzymes, make them ideal candidate enzymes to increase the repertoire of recognition sites available within a given target nucleic acid for use in the method. One advantage would be to provide a more convenient option than isolating or engineering a nicking agent for a particular target nucleic acid for which a nicking agent is not yet readily available. The extensive published work on programmable nicking enzymes, provides a proof of concept for the potential for them to be adopted directly as a nicking agent for the performance of the method.

Additionally, it is also envisaged that other enzymes may be used as nicking agents. A non-limiting list of examples would include enzymes such as RNaseH, DNAzymes, current or newly discovered, mutant or engineered versions of known restriction enzymes and newly discovered nicking endonucleases. Enzymes may be engineered by both rational design and/or directed evolution, which mimics the process of natural evolution to engineer new enzymes and functionalities in a controlled laboratory experiment. A number of nicking endonucleases from those currently commercially available have been engineered by rational modification of existing double-strand cleaving endonucleases of which a larger number are currently commercially available. Additionally, another potentially interesting nicking agent for the performance of the method could be the CEL I nuclease or "surveyor enzyme". This endonuclease has a novel ability to cleave mismatched base pairings, and cleave duplexed nucleic acid molecules when it recognises small insertions or deletions present between the two hybridised nucleic acid sequences. This could be of potential benefit in targeting certain probes for detection in which the sequence of interest is not precisely known, for example, targeting a region of unknown mutational status.

Thus, in one embodiment one or more of the nicking agents in steps a) and/or b) is a naturally occurring enzyme, such as a nicking restriction endonuclease. Alternatively, one or more of the nicking agents in steps a) and/or b) is an engineered enzyme, such as a mutated form of a naturally occurring enzyme or a DNAzyme. Alternatively, one or more of the nicking agents in steps a) and/or b) is a programmable nicking enzyme.

In order to determine the presence of target nucleic acid, the probe fragment (F2) produced is detected either during or at the end of a reaction, which can be accomplished by any technique which can detect the presence of the probe fragment produced following cleavage of oligonucleotide probe (P2). Alternatively the presence or level of the probe fragment (F2) can be inferred by detection of the presence or quantity of uncleaved oligonucleotide probe (P2) during or after a cleavage reaction, or alternatively by detection of the presence or quantity of both of the fragments produced in the cleavage of oligonucleotide probe (P2). Simple embodiments of the invention may achieve such detection through the use of intercalating nucleic acid dyes, such as for example, SYBR gold, in conjunction with a size separation technique such as agarose gel electrophoresis, polyacrylamide gel electrophoresis (PAGE) or capillary electrophoresis. A large number of such intercalating dyes are available, such as, for example Ethidium bromide, SYBR green, picogreen, GelRed, GelStar etc. Other techniques that may be employed for the detection of nucleic acids such as probe fragment(s) which could be employed in embodiments of the method include: mass spectrometry (such as MALDI or LC-TOF), luminescence spectroscopy or spectrometry, fluorescence spectroscopy or spectrometry, liquid chromatography or fluorescence polarization.

For practical application of the invention, it may be advantageous to couple the performance of the method with a technique capable of quantitative and real-time detection of the formation of one or more probe fragment. A number of approaches which can achieve this are envisaged.

The components required for performance of the method, including nicking agent and oligonucleotide probes may be lyophilised for stable storage and the reaction may then be triggered by rehydration, such as upon addition of the sample.

In the simplest form colorimetric and fluorometric methods can be used to detect probe fragment (F2) in step c), without any modification to the oligonucleotide probes used in the method, by, for example, specifically binding or attaching dyes to the probe fragment(s) during or after the method.

Alternatively, the probe fragment (F2) produced in step b) is attached to a moiety that permits its detection, such as a colorimetric or fluorometric dye or a moiety that is capable of attachment to a colorimetric dye e.g. biotin.

In an alternative approach, the probe fragment (F2) produced in step b) is attached to an enzyme and the presence of said probe fragment is detected by contacting said enzyme with a substrate that yields a signal, such as a colorimetric or fluorometric signal, following action of the enzyme, wherein the presence of signal indicates the presence of the target nucleic acid in said sample. In an embodiment said substrate may be insoluble in water under the conditions employed in the cleavage reactions.

In one embodiment the probe fragment (F2) is detected using nucleic acid lateral flow. Nucleic acid lateral flow, wherein nucleic acids are separated from other reaction components by their diffusion through a membrane, typically made of nitrocellulose, is a rapid and low-cost method of detection capable of coupling with a range of signal read-outs, including colorimetric, fluorometric and electrical signals. The present invention is particularly amenable to use with nucleic acid lateral flow because the single-stranded probe fragments generated through the performance of the method readily flow along the membrane and are available for sequence specific detection via hybridisation. Thus in some embodiments the nucleic acid lateral flow detection utilises one or more oligonucleotide(s) that is capable of sequence specific hybridisation to one or more of the probe fragments. Alternative methods, such as PCR or polymerase based isothermal amplification methods, typically generate double-stranded DNA products, which are not available for detection based upon sequence specific hybridisation. Furthermore, the probe fragments to be detected are particularly amenable to multiplex detection, by virtue of the use of location specific hybridisation based detection.

In another approach, the presence of probe fragment (F2) in step c) is detected electrically, such as by a change in impedance resulting from the cleavage of the second oligonucleotide probe P2, or other conductimetric, amperometric, voltammetric or potentiometric methods.

Fluorometric detection can be achieved through the performance of any method which is based on the incorporation of an intercalating dye which binds to either single stranded nucleic acids. These types of dye, under appropriate excitation stimulus, emit a fluorescent signal leading to subsequent detection of the target nucleic acid. Other dyes for direct fluorescence detection include, without limitation: quantum dots, ALEXA dyes, fluorescein, ATTO dyes, rhodamine and texas red. In embodiments of the method that employ a fluorescent dye moiety attached to an oligonucleotide probe or probe fragment, it is also possible to perform detection based on fluorescence resonance energy transfer (FRET), such as employed in Taqman quantitative PCR or Molecular Beacon based strategies for nucleic acid detection, whereby the signal would increase upon cleavage of an oligonucleotide probe to produce a probe fragment. Generally, when a fluorometric approach is used a number of different detectors devices can be used to record the generation of fluorescent signal, such as for example CCD cameras, fluorescence scanners, fluorescence based microplate readers or fluorescence microscopes.

Other embodiments of the invention use colorimetric signal to detect the presence of probe fragment (F2). Such methods would have the advantage of not requiring an instrument to perform fluorescence excitation and detection and potentially of allowing the presence of target nucleic acid to be determined by eye. Colorimetric detection can be achieved by directly attaching a colorimetric dye or moiety to the oligonucleotide probe of interest prior to its use in the method, or alternatively specifically attaching or binding the dye or moiety to the probe fragment following cleavage. For example, a probe fragment(s) to be detected may contain a biotin moiety that permits its binding to a streptavidin conjugated colorimetric dye for its subsequent detection. One such example of a colorimetric dye that is widely used in detection assays is gold nanoparticles. Similar methods can be employed with a variety of other intrinsically colorimetric moieties, of which a very large number are known and widely used in biochemical research (such as carbon nanoparticles, silver nanoparticles, iron oxide nanoparticles, quantum dots etc.). Gold nanoparticles or other dyes could, for example, exist in the solid phase when attached to oligonucleotide probes that are attached to a solid surface, leading to a colourless aqueous phase. Cleavage of the oligonucleotide probe would then release the probe fragment and consequently the colorimetric dye into solution, which disperses and causes the appearance of colour in solution. A high extinction coefficient dye also provides potential for sensitive real-time quantification during the reaction.

In some embodiments of the invention, colorimetric dyes such as carbon or gold nanoparticles may also be detected using lateral flow, for example, on a nitrocellulose strip. As in aqueous embodiments, such carbon or gold nanoparticles may be released as a result of probe cleavage, but would migrate on the nitrocellulose strip. The released nanoparticles may still be attached to a fragment of oligonucleotide probe. A nitrocellulose strip would contain a probe complementary to the relevant probe fragment attached to the carbon or gold nanoparticles. Interaction between complementary probe on the nitrocellulose and gold particles causes local concentration of carbon or gold, causing appearance of a black or red colour, respectively. Alternatively the probe fragments to be detected would contain a moiety, such as a biotin, that permits their binding to a colorimetric dye prior to detection following the sequence specific hybridisation of the relevant probe fragment to a complementary oligonucleotide probe on a nucleic acid lateral flow strip, or a sandwich assay may be performed where the probe fragment produced hybridises to a dye-conjugated complementary oligonucleotide and also binds to a complementary third oligonucleotide immobilised on a lateral flow strip.

A number of considerations are taken into account when choosing an appropriate dye for a given application. For example, in embodiments where it is intended to perform visible colorimetric detection in solution, it would generally be advantageous to choose larger size particles and/or those with a higher extinction coefficient for ease of detection, whereas for embodiments incorporating a lateral flow membrane intended for visible detection, might benefit from the ability of smaller sized particles to more rapid diffuse along a membrane. While various sizes and shapes of gold nanoparticles are available, a number of other colorimetric moieties of interest are also available which include polystyrene or latex based microspheres/nanoparticles. Particles of this nature are also available in a number of colours, which can be useful in order to tag and differentially detect different oligonucleotide probe fragments during the performance of the method, or "multiplex" the colorimetric signal produced in a detection reaction.

Certain embodiments of the method involve one or more of the probe fragments being attached to an enzyme capable of generating a colorimetric or fluorometric signal after contacting said enzyme with a substrate. In this way the presence of the colorimetric or fluorometric signal corresponds to the presence of the probe fragment and therefore to the presence of the target nucleic acid in the sample. Some embodiments of the method use horseradish peroxidase (HRP) as the enzyme, which has been widely used as a reporter for ELISA, Western blot and immunohistochemistry applications. Its exceptionally high substrate turnover rate, and stability under relevant assay conditions (temperature, buffer and pH) make it particularly amenable to colorimetric reporting and signal amplification. Another reporter system involves the use of glycosyl hydrolase enzymes. This class of enzyme catalyses the hydrolysis of a polymeric sugar molecules, which can be synthesized with internal AZCL dye molecules. The sugar resides in the solid phase until enzymatic hydrolysis liberates dye molecules, which diffuse into solution. One example is endo-1,4-β-galactanase from *Clostridium* thennocellum which exhibits high specific activity and stability under assay conditions. Importantly, horseradish peroxidase and endo-1,4-β-galactanase can be conjugated efficiently to an oligonucleotide probe. Both enzymes also have a relatively low molecular weight (40 kDa and 36 kDa respectively) which minimizes steric hindrance of probe cleavage event. Certain embodiments of the method could rely on alternative enzymes for generating a colorimetric signal. In theory, any enzyme which can be conjugated to an oligonucleotide probe and which can convert a substrate to a coloured product may be appropriate for use in the performance of the method. Suitable colorimetric enzymes might include: peptidases or amylases, esterases (e.g. carboxyesterase), glycosidases (e.g. galactosidase), and phosphatases (e.g. alkaline phosphatase). This list should not be considered in any way limiting.

The substrate for an enzyme used in detection may be insoluble in water. If such a substrate (e.g. AZCL Galactan in the case of Galactose or o-Dianisidine in the case of HRP) is insoluble in water under the aqueous conditions of the probe cleavage reaction, probe fragment conjugated to enzyme released into the aqueous phase following cleavage of an oligonucleotide probe attached to a solid material, would be able to access and digest the substrate to produce a colour change. In this way said enzyme may be used to produce a colorimetric signal in the presence of target nucleic acid in a single pot reaction. If oligonucleotide probe (P2) is attached to an enzyme then enhanced amplification effect may be obtained, by virtue of the fact that each molecule of enzyme released following cleavage of the probe would thereafter generate many copies of its substrate to its product.

The detection method to be employed in step c) of the method may include further amplification initiated by oligonucleotide probe fragment (F2). For example, fragment (F2) may be contacted with:
  i. a third oligonucleotide probe (P3); and
  ii. a third nicking agent;
  wherein the third oligonucleotide probe (P3) comprises a complementarity region capable of sequence specific hybridisation to fragment (F2) which following hybridisation to fragment (F2) produces a cleavage site for the third nicking agent; whereby the third nicking agent specifically recognises the double-stranded nucleic acid formed when the third oligonucleotide probe (P3) hybridises to fragment (F2) and cleaves said third oligonucleotide probe (P3) to produce a probe fragment (F3). Optionally the foregoing may be repeated n times, wherein n is a positive integer, using fourth and subsequent sequential (3+n)th oligonucleotide probe(s) to produce fourth and subsequent sequential (3+n)th probe fragment(s). The detection of fragment(s) F3, F(3+n) is then performed as a surrogate for the detection of the presence of fragment F2 in step c) of the method.

In a number of embodiments detection may be performed in a quantitative manner. Thus, the level of target nucleic acid in the sample may be quantified in step c).

A further aspect of the invention relates to kits for use in the detection of nucleic acids of defined sequence in a sample. Thus the invention also provides a kit comprising the following:
  a) a first oligonucleotide probe (P1); and
  b) a second oligonucleotide probe (P2);
  wherein the first oligonucleotide probe (P1) and the second oligonucleotide probe (P2) are as defined in any of the methods of the invention as described herein.

The invention also provides a kit comprising the following:
  a) a first oligonucleotide probe (P1);
  b) a first nicking agent;
  c) a second oligonucleotide probe (P2); and
  d) a second nicking agent;
  wherein the first oligonucleotide probe (P1), the first nicking agent, the second oligonucleotide probe (P2) and the second nicking agent are as defined in any of the methods of the invention as described herein.

The first and second nicking agents may be the same.

In particular, the kits according to the invention may, optionally in addition to first and/or second nicking agents, comprise:
  a) first oligonucleotide probe (P1) comprising a complementarity region capable of sequence specific hybridisation to a target nucleic acid to produce a double-stranded nucleic acid amplifier comprising a target derived strand containing at least one cleavage site for a first nicking agent which when cleaved produces a primer and fragment (F1), and a probe (P1) derived strand; and
  b) a second oligonucleotide probe (P2) comprising a complementarity region capable of sequence specific hybridisation to fragment (F1) which following hybridisation to fragment (F1) produces a cleavage site for a second nicking agent.

In embodiments of the invention probes (P1) and (P2) have sequence homology, they may be homologous over their full length or over part of their length, the probes (P1) and (P2) may, for example, have homology over 8 to 20, e.g. about 10, contiguous bases. In certain embodiments P1 may have additional sequence to P2 at its 3' end such sequence providing the complement to the primer produced upon cleavage of the double-stranded nucleic acid amplifier. In other embodiments P2 may have additional sequence to P1 at either its 5' or 3' end such sequence enhancing the detection of fragment (F2) that is released from P2 following hybridisation of F1 and cleavage by the second nicking agent. Probes (P1) and (P2) may both comprise the recognition site for the nicking agent(s), the recognition sites are preferably the same.

In certain embodiments oligonucleotide probe (P1) comprises one or more modifications, such as one or more phosphorothioate linkages, that render it resistant to cleavage by the first and/or second nicking agent(s).

The first oligonucleotide probe may comprise a complementarity region at its 3' end that is capable of sequence specific hybridisation to the target nucleic acid. When the first oligonucleotide probe comprises a complementarity region at its 3' end that is capable of sequence specific hybridisation to the target nucleic acid the kit may optionally also comprise a target nucleic acid primer. The target nucleic acid primer optionally may not contain the recognition sequence or cleavage site for the first nicking agent.

The kits may additionally comprise:
a) a probe (P1) nicking agent; and/or
b) a target nucleic acid primer.
wherein the probe (P1) nicking agent and/or target nucleic acid primer are as defined above in relation to the methods of the invention.

In the kits the second oligonucleotide probe (P2) may be attached to a solid material or to a moiety that permits its attachment to a solid material. The first oligonucleotide probe (P1) may also be attached to a solid material or to a moiety that permits its attachment to a solid material.

The kits according to the invention may further comprise additional components and/or reagents for use in the methods, for example the kits may also comprise a polymerase, for example a strand displacement polymerase. The kits may also include reagents such as reaction buffers, salts e.g. divalent metal ions and deoxyribonucleotides.

In one embodiment the kits of the invention may comprise the following:
a) a probe (P1) nicking agent;
b) a first nicking agent;
c) a first oligonucleotide probe (P1) that contains a complementarity region at its 3' end that is capable of sequence specific hybridisation to a target nucleic acid and contains the recognition sequence for the probe (P1) nicking agent;
d) a target nucleic acid primer that contains a complementary region at its 3' end that has the same sequence as the target nucleic acid and contains the recognition sequence for the first nicking agent;
e) a polymerase;
f) a second nicking agent; and
g) a second oligonucleotide probe (P2) that contains a complementarity region capable of sequence specific hybridisation to a fragment displaceable from the target nucleic acid primer and a cleavage site for the second nicking agent.

The kits according to the invention may further comprise components for the detection of a probe fragment (F2) as herein described.

The kits according to the invention may be provided together with instructions for the performance of the methods according to the invention.

The invention also provides the use the kits of the invention for the detection of a target nucleic acid of defined sequence in a sample.

It is to be understood that all the optional and/or preferred embodiments of the invention described herein in relation to the methods of the invention also apply in relation to the kits of the invention and the use thereof, and vice versa.

The method of the invention may also be used independently from the detection step c) for amplifying a nucleic acid signal from a target nucleic acid of defined sequence, such a method may be used, for example, if the amplified signal is to be stored and/or transported for detection of the target nucleic acid at a future date and/or alternative location if required. The amplified signal comprises probe fragments of defined sequences produced through performance of the method. Thus in a further embodiment the invention provides a method of amplifying a nucleic acid signal from a target nucleic acid of defined sequence in a sample comprising steps a) and b) of the method of the invention, wherein amplified nucleic acid is a probe fragment produced at the end of step b).

The invention also provides the use the kits of the invention for amplifying a nucleic acid signal from a target nucleic acid of defined sequence as defined above.

It is to be understood that all the optional and/or preferred embodiments of the invention described herein in relation to the methods for detecting the presence of a target nucleic acid of defined sequence in a sample of the invention also apply in relation to the method for amplifying a nucleic acid signal from a target nucleic acid of defined sequence.

The current invention is of broad utility to various fields and applications which require detection of nucleic acid of defined sequence in a sample. It represents a fast, cheap and convenient means of determination of the presence of a target nucleic acid sequence within a sample. By way of a list of applications that is in no way limiting, we envisage that the invention could be of value in fields such as; diagnostics, forensics, agriculture, animal health, environment, defence, human genetic testing, prenatal testing, blood contamination screening, pharmacogenomics or pharmacokinetics and microbiological, clinical and biomedical research. Suitably the sample is a biological sample such as a human sample. The sample may be a human sample, a forensic sample, an agricultural sample, a veterinary sample, an environmental sample or a biodefence sample. It is envisaged that the invention would be amenable for use with a broad array of sample types, such as, for example: Nasal swabs or aspirates, nasopharyngeal swabs or aspirates, throat swabs or aspirates, cheek swabs or aspirate, blood or a sample derived from blood, urine or a sample derived from urine, sputum or a sample derived from sputum, stool or a sample derived from stool, cerebrospinal fluid (CSF) or a sample derived from CSF, and gastric fluids or a sample derived from gastric fluids, human or animal samples derived from any form of tissue biopsy or bodily fluid. The target nucleic acid may be (a) viral or derived from viral nucleic acid material (b) bacterial or derived from bacterial nucleic acid material (c) circulating cell-free DNA released from cancer cells (d) circulating cell-free DNA released from foetal cells or (e) micro RNA or derived from micro RNA inter alia.

The target nucleic acid may also be the product of reverse transcriptase, an RNA polymerase or a DNA polymerase. The target nucleic acid sequence may be naturally occurring or non-naturally occurring. The target nucleic acid may be generated in situ or produced from a naturally occurring nucleic acid prior to performance of the method. A target nucleic acid may be prepared by digestion by a nicking agent or double-strand cleaving agent in order to expose the necessary 3' complementarity region for sequence specific hybridisation to oligonucleotide probe (P1) and polymerase extension necessary to produce the double-stranded nucleic acid amplifier in step a) of the method. The target nucleic acid may alternatively be a probe fragment produced following cleavage of an oligonucleotide probe by a nicking agent or a restriction enzyme other than a nicking agent, such as a double strand cleaving restriction endonuclease, of which a large number are available covering a broad range of recognition sequences. Said probe fragment may be produced by contacting a naturally occurring nucleic acid in a sample with such a nicking agent or double strand cleaving restriction endonuclease and an oligonucleotide comprising a first complementarity region capable of sequence specific hybridisation to said naturally occurring nucleic acid and a cleavage site for said nicking agent or restriction endonuclease; and wherein said nicking agent the restriction endonuclease specifically recognises double-stranded nucleic acid formed when said oligonucleotide probe hybridises to said naturally occurring nucleic acid in said sample and cleaves said oligonucleotide probe to produce the target nucleic acid for the method. Therefore in an embodiment the target nucleic acid is a probe fragment produced following cleavage of an oligonucleotide probe by a double-strand cleaving agent.

Generating the target nucleic acid for the method in this way has a number of potential advantages. For example, if a conventional nicking agent could not be identified for a particular nucleic acid, a double strand cleaving restriction endonuclease, of which a greater number are currently known, could be employed to produce a target nucleic acid probe fragment containing a sequence that contains the antisense of a recognition sequence and cleavage site for a nicking agent to allow the method to be performed. Provided that the "real" nucleic acid in the sample to be detected is converted into the "surrogate" target nucleic acid for performance of the method with reliable conversion (which may be <1:1, 1:1 or 1:>1 i.e. possibly with some element of amplification) then detection of the "surrogate" target nucleic acid will allow the "real" nucleic acid to be detected and/or quantified. Furthermore, production of a surrogate target from a naturally occurring target in this way can be used to generate in a specific manner a target nucleic acid for the method with any desired sequence, such as a probe fragment that is capable of sequence specific hybridisation to probe (P1) before being extended to produce the double-stranded nucleic acid amplifier.

It is also envisaged that the current invention has the potential to be of utility in screening samples for cell free DNA and epigenetic modifications such as, for example, CpG methylation of DNA sequences. Such epigenetic modification of particular cancer associated target genes can serve as useful biomarkers in a number of diseases and disease states. Methylation of nucleic acid recognition sequence is known to form part of the recognition site for certain nicking endonucleases, for example, Nt.BsmAI, Nt.CviPII and Nt.BbvCI are sensitive to CpG methylation at their recognition sequence. Given the growing appreciation of the importance of epigenetic modification in human disease, there is potential for the present invention to be used to specifically assess the epigenetic modification of particular target nucleic acid biomarkers. Therefore, in an embodiment, the target nucleic acid contains a site of epigenetic modification, such as methylation. Alternative the "real" nucleic acid used to produce a "surrogate" target nucleic acid for the performance of the method, as described above, contains a site of epigenetic modification.

Detection of target nucleic acid may be used for the diagnosis, prognosis or monitoring of disease or a diseased state such as an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, *chlamydia*, herpes, gonorrhoea, measles, mumps, rubella, cholera or smallpox, or cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma, or in the fields of human genetic testing, prenatal testing, blood contamination screening, pharmacogenetics or pharmacokinetics.

The presence of two or more different target nucleic acids of defined sequence may be detected in the same sample. In an embodiment of the method, separate series of steps a), b), and c), using different oligonucleotide probes (P1) and (P2) for each of the two or more target nucleic acids is performed, which separate steps may be conducted simultaneously. For example, in an embodiment, one set of oligonucleotide probes would be used for the detection of one target nucleic acid in a sample and another set of oligonucleotide probes would be used for the detection of another target nucleic acid in the same sample. The detection of the probe fragment(s) produced from the two or more different sets of probes could each be coupled to a particular signal, such as different colorimetric or fluorometric dyes or enzymes, to allow multiplex detection. The fact that the probe fragment(s) to be detected are single-stranded nucleic acids, typically released into the aqueous phase from a solid material, enables their subsequent differential detection based upon sequence specific hybridisation, which means the present invention possesses a powerful advantage over other methods in terms of its multiplexing capability (see Example 3). For example, most polymerase-based methods produce a double-stranded nucleic acid product, which would not be suitable for subsequent detection based upon sequence-specific hybridisation. Since the present method does not involve the generation of the target sequence and instead produces an end-point amplicon fragment (F2), it avoids competition for binding to F2 wherein other nucleic acids present in the reaction would act as a 'sink' thus hampering the ability to detect said probe fragment F2. Instead, in certain embodiments of the present invention an 'end-point' detection system is employed wherein probe fragment (F2) accumulates without such competitive binding, enabling its efficient subsequent detection. In certain embodiments, multiple different probe fragments produced from different series of oligonucleotide probes can be differentially detected using nucleic acid lateral flow, wherein multiple oligonucleotides comprising complementary sequence to each of the probe fragment(s) are each immobilised on the nitrocellulose membrane in a discrete location; thus a single colorimetric dye can be used for simultaneous detection of many different target nucleic acids in the same sample.

In alternative embodiments two or more variants of the first oligonucleotide probe could be used to detect different target nucleic acids; whilst the probe fragment (F1) from both probes would hybridise to the same second oligonucleotide probe (P2) and therefore link to the same fragment (F2) and, ultimately, the same detection signal. More generally, any probe fragment may be designed to hybridise to almost any other oligonucleotide probe employed in the method, by virtue of the flexibility in the design of the complementarity regions of the oligonucleotide probes. There is typically no requirement for the oligonucleotide probes of the present method to produce functional equivalents of the target nucleic acid for its use in the detection of said target nucleic acid, as is the case for methods such as PCR. By avoiding amplification of the target sequence in this way, considerably increased versatility in multiplexing is conferred. Furthermore, the sequence of most of the first oligonucleotide probe (P1) and all of the second oligonucleotide probe (P2) can be defined, enabling the same reagents to be employed for the amplification and detection of many different target nucleic acids by replacing only the first oligonucleotide probe; a "universal amplification and detection system".

The following examples serve to further illustrate various aspects and embodiments of the methods described herein. These examples should not be considered limiting in any way.

EXAMPLES

Materials and Methods

The following materials and methods are used in the examples below unless otherwise indicated.

Oligonucleotides: Except as otherwise indicated custom oligonucleotides were manufactured using the phosphoramidite method by Integrated DNA Technologies.

Attachment of oligonucleotide probes to streptavidin magnetic beads: Streptavidin-coupled beads are super paramagnetic beads used for attaching biotin containing biomolecules to a solid matrix in a variety of applications. They can be efficiently bound to biotinylated oligonucleotides probes. To ensure complete absorption of biotinylated oligonucleotides and avoid the presence of unbound oligonucleotide in solution when generating reagents for performance of the method, beads were typically saturated to approximately 50% of their binding capacity. In a standard coupling reaction streptavidin magnetic beads (C1 Dynabeads, Life technologies) were prepared by washing by incubation at 2 mg/ml (w/v) in 2×BW buffer (10 mM Tris HCl (pH 7.5), 1 mM EDTA, 2M NaCl) at room temperature for one min. Beads were then recovered using a magnet and washed at 2 mg/ml in 1×BW buffer at room temperature for one minute. For coupling, beads were resuspended at 2 mg/ml in 1×BW buffer with 25 pmol of biotinylated oligonucleotide per 100 µg of streptavidin beads. This mixture was incubated for 30 min at room temperature, shaking vigorously. After conjugation, the beads were thoroughly washed according to the manufacturer's protocol and resuspended in appropriate buffer for immediate use or storage.

Attachment of oligonucleotide probes to carboxylic acid beads: Carboxylic acid beads (MyOne, Life Technologies) are 1 µm, mono-sized super paramagnetic beads with a highly cross-linked polystyrene surface functionalised with carboxylic acid groups Amine modified oligonucleotide probes can be reacted with the beads in the presence of a suitable carbodiimide cross-linking reagent, such as 1-ethyl-3-(3-dimethylaminopropyl) carbodiimide (EDC). The reaction forms an amide bond rendering the amine modified oligonucleotide probe immobilised on the bead surface. In a standard coupling reaction protocol 1.2 mg of Dynabeads MyOne Carboxylic acid beads were prepared by washing twice at room temperature in 1×PBS for 5 min. Following each wash the beads were recovered by magnet pull-down and the supernatant was discarded. Beads were then added to conjugation reactions in 100 µl of 100 mM MES buffer (pH 4.8), containing 200 mM EDC (added from freshly prepared 1M EDC stock) and 4.8 nmol of amine modified oligonucleotide and incubated at room temperature for 2 hours with vigorous shaking. Following the reaction, beads were recovered using a magnet, the supernatant was discarded and the beads were quenched by addition of 50 µl of 50 mM ethanolamine solution in 1×PBS (pH 8.0) for 60 mM at room temperature with shaking. The beads were then washed three times in 1 ml PBS (pH 7.4)+0.1% Tween 20 for 2 mM with mixing and re-suspended in appropriate buffer for immediate use or storage.

Traut's reagent conversion of amine modified oligonucleotide to sulfhydryl: A reaction was prepared containing 100 pmol/µl amine modified oligonucleotides, 2 nmol/µl Traut's reagent (2-iminothiolane) and 1 mM EDTA in 1×PBS (pH 8.0) and incubated at room temperature for one hour with shaking. Subsequently, removal of excess Traut's reagent and clean-up was performed using a 7 kDa MWCO desalting column (Zeba Spin Desalting Column, Life Technologies) equilibrated with 1×PBS (pH 7.2)+1 mM EDTA, following the manufacturer's protocol. The thiol modified oligo produced was used directly for maleimide bead coupling as described below. In order to prepare sulfhydryl oligonucleotide for conjugation to maleimide-activated proteins the protocol was performed as described above but at 200 pmol/µl amine modified oligonucleotides and 4 nmol/µl Traut's reagent.

Attachment of oligonucleotide probes to maleimide beads: Maleimide beads (Cube Biotech GmbH) are spherical 25 µm diameter magnetic beads coated with 6% cross-linked agarose. The maleimide moiety is coupled to the magnetic agarose via an epoxide function and C40 spacer to obtain a high binding capacity for conjugation to thiol groups and reduced non-specific binding. Thiol modified oligonucleotide probes can be conjugated to the beads in order to create a stable covalent thioether bond. In a standard coupling reaction 30 mg (120 µl of 25% w/v suspension) of maleimide activated beads were prepared by washing four times in 1×PBS (pH 7.2)+1 mM EDTA. Following each wash the beads were recovered by magnet pull-down and the supernatant was discarded. 4 nmol of thiol modified oligonucleotide was incubated for one hour at room temperature with shaking in 40 µl of 1×PBS (pH 7.2) containing 10 mM TCEP and 1 mM EDTA. The oligonucleotide was then desalted using a 7 kDa MWCO desalting column (Zeba Spin Desalting Column, Life Technologies) equilibrated with 1×PBS (pH 7.2)+1 mM EDTA and added to the 30 mg of beads. For thiol oligo prepared by Traut's treatment, TCEP treatment of the oligo was omitted and 4 nmol oligo was added directly to 30 mg beads in 40 µl of 1×PBS (pH 7.2)+1 mM EDTA. In each case the conjugation reaction was incubated for two hours at room temperature with shaking. The beads were then washed six times in 1×PBS (pH 7.4) with 0.1% Tween 20 and twice in 1×PBS (pH 7.4), before resuspension in an appropriate buffer for storage or use.

Polyacrylamide Gel electrophoresis (PAGE): Samples were separated using 15% polyacrylamide, 7M urea gels using standard procedures described in detail elsewhere (Sambrook, J., and Russell, D. 2001, Molecular Cloning a laboratory manual, Third Ed. Cold Spring Harbor Press).

Carbon Nucleic Acid Lateral Flow Assay: Carbon nanoparticles were conjugated via non-covalent adsorption to various biotin-binding proteins, e.g. streptavidin. Typically, a colloidal carbon suspension was prepared in Borate Buffer followed by sonication using a probe sonicator. Carbon was subsequently adsorbed to biotin-binding protein by incubation at room temperature before being extensively washed. Carbon was applied to glass fibre conjugate pads before being air dried. Typically, additives, e.g. BSA, were added to the buffer used for washing and drying the carbon. Lateral flow strips were constructed by combining a dried carbon conjugate pad, with a sample pad, nitrocellulose membrane and adsorbent pad (Merck Millipore) following the manufacturer's guidelines. Prior to its use in lateral flow strips, the relevant oligonucleotide(s) containing the reverse complement of the sequence of the probe fragment(s) to be detected in the method were printed onto the nitrocellulose membrane at a defined location and attached to the membrane via UV cross-linking.

TABLE 1

Oligonucleotide sequences used in the examples
(* = phosphorothioate internucleotide linkage).

| ID | Oligonucleotide Sequences (5'-3') |
|---|---|
| SEQ1 | ATATATATATAGGAGTCTCGGCATCTATATATATATAT |
| SEQ2 | ATATATATATATATATTTGAGTCATAGAGATGCCGAGACTCCT |
| SEQ3 | TTTTTTTTTTTTTTGAGAGCCAGGACCAGGAACACA |
| SEQ4 | TTTTTTTTTTTTTTTGTGTTCCTGGTCCTGGCTCTC |
| SEQ5 | ATTAATACCATCAAAATGTATATAT |
| SEQ6 | ATATATAC*ATTTTGATGGTAT |
| SEQ7 | ATATATAC*ATTTTGAAGGTAT |
| SEQ8 | ATTTTGATGGTAT |
| SEQ9 | TTACTGAGGATATTGCTTGAAGCTGGCAGTGCCTCTCGATCCGAATGCTCAGAGACA GAAGAGCGCAATGGGGACTCTTACTGAGGATATTGCTTGAAGCTG |
| SEQ10 | AAAAAAAAAAGTAAAAGAGTCTGTCCATCACTAAAAAAAAAA |
| SEQ11 | ATATATATATATTAAACCAAGTACCGCACTATATATATAT |
| SEQ12 | ATATATATATCGCAGTCTCTGAATATATATATAT |
| SEQ13 | AAAAAAAAAAGAGAGGCACTGCCAGCTTAAAAAAAAAA |
| SEQ14 | ATATATATACGCCAGCCATTGCAACAGGAATATATATAT |
| SEQ15 | ATATATATATATATTTCGTCTCGATTCGATATCTTGACTCCTT |
| SEQ16 | TTCTTCTTCTTGGTCTCACTCATGAGGACGCC |
| SEQ17 | TTCTTCTTCTTGGTCTCCAGGAGACCGGTCTT |
| SEQ18 | CAGGAGACCGGTCTTCCCGAGGGCGTCCTCAGGAGT |
| SEQ19 | CCTTGTGTTCACCGGTCTTCCCGAGGGTTTTCTTCTTCTTTTTT |
| SEQ20 | TTCTTCTTCTTGGTCTCACTCATGAGGACGCC |
| SEQ21 | TTGTTGTTGTTGGTCTCGGAGACCGGATCGTT |
| SEQ22 | TGTCCATGTTTTTTTGGAGACCGGATCGTTACGGCGTCCTCATGAGTAAAAATGTCCATG |
| SEQ23 | CCTTGTGTTCCCGGATCGTTACGGCTTTTCTTCTTCTTTTTT |
| SEQ24 | GTTGTTGTGCTTCCCGAGGACGCCAATAGAGGA |
| SEQ25 | GTTGTTGTGCTTCCCGAGTAGAGGCAGGTGACC |
| SEQ26 | TGTCCATGTTTTTTTAGAGGCAGGTGACCGGTCTCCTCTATTGGCGTCCAAAAAATGTCCATG |
| SEQ27 | CCTTGTGTTCCCGGTCTCCTCTATTGTTTTCTTCTTCTTTTT |

Example 1

Detection of Target Nucleic Acids Using Linear Amplification in Step a)

In this example we performed detection of a control target nucleic acid using an embodiment of the method of the invention with linear amplification in step a), i.e. with no cross-priming and with a single nicking agent cleavage site in the double-stranded nucleic acid amplifier. A synthetic DNA oligonucleotide was employed as control target and detection of probe fragments F2 produced following cleavage of probe P2 was performed using either polyacrylamide gel electrophoresis, stained with SYBR Gold, or by nucleic acid lateral flow with colorimetric detection (carbon nanoparticles).

Firstly oligonucleotide probe P1 was designed comprising in the 5' to 3' direction 26 nucleotide bases of single stranded DNA with the following sequence components: (i) 10 bases comprising the complementary sequence of a nicking agent recognition sequence and cleavage site present within the target nucleic acid; and (ii) 16 bases of additional sequence complementary to the target nucleic acid. A double strand cleaving agent (a class II restriction endonuclease) was employed as the first and second nicking agent and the potential cleavage of P1 was blocked by use of a phosphorothioate base at the potential top strand cleavage site (indicated by *). The following symbols are used to indicate the design of the probes: X=Nucleotide base (A, T, C or G) of the nicking agent recognition site; B=Nucleotide base (A, T, C or G) of complementary sequence to the target nucleic acid. The target contained the reverse complement of the sequence of P1 (indicated by lower case). /=cleavage position.

```
P1:
5'-XXXXXB*BBBB_BBBBBBBBBBBBBBBB-3'

Target:
3'-xxxxxb_bbbb/bbbbbbbbbbbbbbbb-5'
```

Oligonucleotide probe P2 was designed to contain in the 5' to 3' direction: (i) an 11 base spacer; (ii) the same 10 base pair nicking agent recognition sequence and cleavage site as in P1 but without the phosphorothioate base, and (iii) 21 bases of sequence for detection of fragment F2, e.g. by nucleic acid lateral flow, indicated by L. N=any nucleotide base (A, T, C or G) spacer.

```
P2:
5'-NNNNNNNNNNNXXXXXB/BBBBLLLLLLLLLLLLLLLLLLLLL-3'
```

Based on the design of P1 and P2 outlined above, during performance of the method, P1 hybridises to the target nucleic acid which is cleaved to produce a primer consisting of the 16 bases at the 5' end of the target derived strand (indicated by 'b') and extended to form the double-stranded nucleic acid amplifier, of the following composition. TS=Target derived strand.

```
P1:
5'-XXXXXB*BBBB_BBBBBBBBBBBBBBBB-3'

TS:
3'-xxxxxb_bbbb/bbbbbbbbbbbbbbbb-5'
```

Many copies of the 10 base sequence 3'-xxxxxbbbbb-5' (fragment F1) are produced by the sequential action of the polymerase and the nicking agent. Fragment F1 represents a truncated template for the nicking agent. F1 hybridises to P2 to form the nicking agent cleavage site, leading to the cleavage of P2 to produce the detection fragment F2 comprising the sequence 5'-BBB-BLLLLLLLLLLLLLLLLLLLLL-3'. Due to target recycling, each copy of F1 leads to the cleavage of many copies of P2 to produce many copies of F2.

Figure 3A:
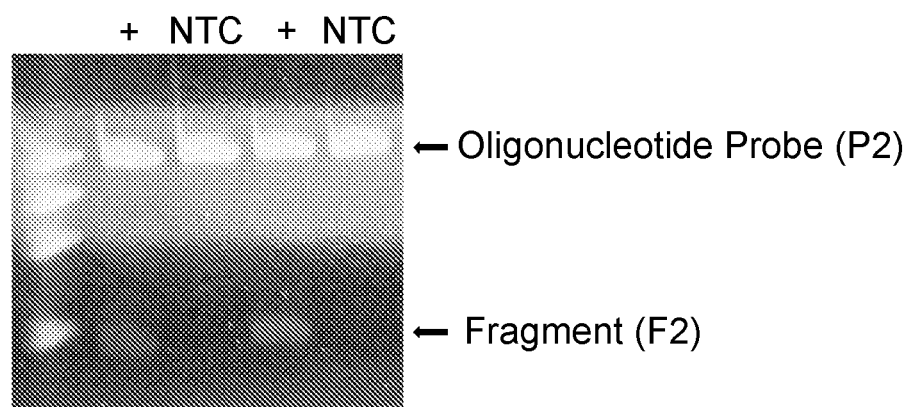
FIG. 3A. Linear amplification in step a) and gel electrophoresis detection in step c) (see Example 1).

Reactions were typically assembled in a 10 µl volume containing: 0.01-0.05 pmol probe P1; 1× Cutsmart buffer (NEB); 5 U nicking agent; 5 pmol probe P2, 1 µM dNTP and 1 U of Bst 3.0 polymerase (NEB) and various quantities of target nucleic acid. Reactions were incubated at 37° C. for 30 min. Following incubation, entire reactions were analysed by TBE-Urea polyacrylamide gel electrophoresis (PAGE) using a 15% w/v gel stained with SYBR Gold (Life Technologies) and visualised using a UV transilluminator. Exemplary data (FIG. 3A) displays a photograph of the stained polyacrylamide gel electrophoresis gel. Lane 1 displays a size marker with (50, 40, 30 and 20 bases). +=50 fmol target nucleic acid; NTC=no target control. Lanes 2 and 3 display the results obtained with 0.01 pmol P1 and lanes 4 and 5 display the results obtained with 0.05 pmol P1. A band corresponding to fragment F2 is clearly visible in lanes 2 and 4 indicating that it is only produced in the presence of target nucleic acid.

Figure 3B:
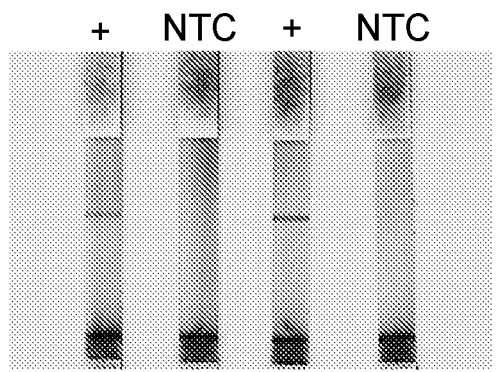
FIG. 3B. Linear amplification in step a) and nucleic acid lateral flow detection in step c) (see Example 1).

In order to demonstrate colorimetric detection using nucleic acid lateral flow, oligonucleotide probe P2 was synthesised with a biotin group on the 3' end and was covalently attached to beads at the 5' end following standard protocols. Reactions were performed in the same way except that probe P2 was added in the form of 3.5 µg beads. Following incubation, 50 µl running buffer was added and each reaction was analysed by applying the entire contents of the reaction onto the sample pad of a lateral flow strip. The nitrocellulose membrane of the lateral flow strip was printed with an oligonucleotide containing the reverse complement to part of the probe fragment F2 released from the bead following cleavage. A photograph of the nitrocellulose membranes following development of the lateral flow strips is displayed in FIG. 3B. The reactions displayed on the 1st and 2nd strips were performed with 0.01 pmol P1 and the 3rd and 4th strips were performed with 0.05 pmol P1. Colorimetric signal was only observed in the presence of target nucleic acid.

This example shows that the method of the invention can be employed in an embodiment in which oligonucleotide probe P1 does not contain any additional designed sequence for cross-priming. In contrast to known methods, it demonstrates that simply by targeting a single nicking agent cleavage site in a target nucleic acid, a readily detectable signal can be generated in a single integrated reaction, with detection of probe fragment F2 by fluorescence (gel electrophoresis, FIG. 3A) or by visual detection by colorimetric methods (nucleic acid lateral flow, FIG. 3B).

Example 2

Detection of Target Nucleic Acids Using Exponential Amplification in Step a)

In this example we performed detection of a viral target nucleic acids using various embodiments of the method of the invention with exponential amplification in step a), i.e. P1 was designed to include cross-priming capability and with multiple nicking agent cleavage sites in the double-stranded nucleic acid amplifier.

2.1. Exponential Amplification in Step a) with No Extension of Oligonucleotide Probe P1.

In this embodiment the double-stranded nucleic acid amplifier is produced as illustrated in FIG. 1, in that oligonucleotide probe P1 does not require extension and can be capped at the 3' end. Steps a), b) and c) of the reaction were performed sequentially and detection in step c) was performed by gel electrophoresis.

Firstly oligonucleotide probe P1 was designed comprising in the 5' to 3' direction 39 bases of single stranded DNA with the following sequence components: (i) 13 bases comprising the complementary sequence of a nicking agent recognition sequence and cleavage site capable of producing a displaced strand fragment that can act as a truncated template for P2; (ii) 10 bases comprising the complementary sequence of a nicking agent recognition sequence and cleavage site present within the target nucleic acid; and (iii) 16 bases of additional sequence complementary to the target nucleic acid. A single double strand cleaving agent (a class II restriction endonuclease) was used as both the first and second nicking agent and cleavage of P1 was blocked by use of a phosphorothioate base at the cleavage site (indicated by *). The following symbols are used to indicate the design of the probes: X=Nucleotide base (A, T, C or G) of the nicking agent recognition site; B, C=Any nucleotide (A, T, C or G) with sequence designed to facilitate cross-priming and detection; D=Any nucleotide (A, T, C or G) of homologous bases to the target nucleic acid. The target contains the reverse complement of part of the sequence of P1 (indicated by lower case); /=cleavage position.

```
P1:
5'-BBBXXXXXC*CBBB_XXXXXD*DDDD_DDDDDDDDDDDDDDD-3'

Target:
3'-xxxxxd_dddd/dddddddddddddddd-5'
```

Following cleavage of the target nucleic acid to produce a primer and extension by the polymerase, the double-stranded nucleic acid amplifier was produced of the following composition.

```
P1:
5'-BBBXXXXXC*CBBB_XXXXXD*DDDD_DDDDDDDDDDDDDDD-3'

Target Strand:
3'-bbbxxxxxc_cbbb/xxxxxd_dddd/dddddddddddddddd-5'
```

Oligonucleotide probe P2 was designed to contain in the 5' to 3' direction: (i) an 11 base spacer; (ii) the same 10 base nicking agent recognition sequence and cleavage site as in P1 but without the phosphorothioate base, and (iii) 21 bases of sequence for detection of fragment F2 by nucleic acid lateral flow, indicated by L. N=any nucleotide (A, T, C or G) spacer.

```
P2:
5'-NNNNNNNNNNNXXXXXC/CBBBLLLLLLLLLLLLLLLLLLLLL-3'
```

Based on the design of P1 and P2 outlined above, following production of the double stranded nucleic acid amplifier, the nicking agent cleaves the target derived strand in two places as indicated and subsequent extension by the polymerase displaces two strand fragments. One of the strand fragments comprises the 13 base sequence denoted as 3'-bbbxxxxxccbbb-5' (F1) which forms the truncated template which is capable of hybridising to P2 to form a cleavage site for the nicking agent. F1 also contains a three base motif at its 3' end 'blob' designed to increase its ability to cross-prime with comparable efficiency to either of the two potential binding sites ('BBBXXXXX') within probe P1. The other strand fragment displaced from P1 comprises the 10 base sequence denoted as 3'-xxxxxddddd-5' which serves as a cross-priming fragment, since after it is displaced it will prime another molecule of probe P1, yielding a secondary double-stranded nucleic acid amplifier capable of generating additional copies of F1. The sequential action of the polymerase and the nicking agent produces many copies of each of the two strand fragments in an exponential step a) reaction. Fragment F1 hybridises to P2 to form the nicking agent recognition site leading to the cleavage of P2 to produce the detection fragment F2 comprising the sequence 5'-DDDDLLLLLLLLLLLLLLLLLLLLL-3'. Due to target recycling, each copy of F1 leads to the cleavage of many copies of P2 to produce many copies of F2.

Reactions for step a) were prepared containing: 0.1 pmol probe P1; 1 U nicking agent; 50 µM dNTP and 1 U of Bst 3.0 polymerase (NEB) and various quantities of target nucleic acid in a final volume of 10 µl containing 1× Isothermal Buffer II (NEB). Reactions were incubated at 32° C. for up to 60 min before inactivation of the polymerase by heating at 95° C. for 10 min. Reactions for step b) were then prepared containing 2 µl of the step a) reaction; 5 pmol probe P2; and 2.5 U nicking agent, in a 10 µl total volume containing 1× Cutsmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 4A:
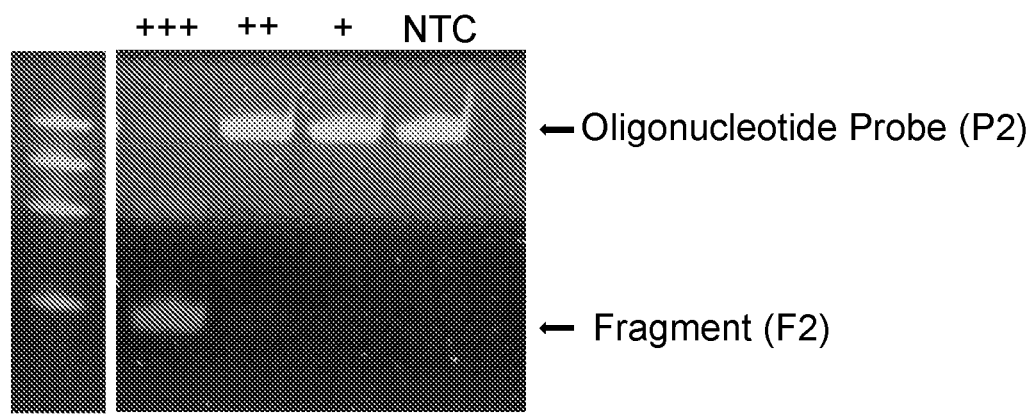
FIG. 4A. Exponential amplification in step a) with no extension of oligonucleotide probe (P1) (see Example 2.1).

Exemplary data (FIG. 4A) displays a photograph of the stained polyacrylamide gel electrophoresis gel. Lane 1 displays a size marker with (50, 40, 30 and 20 bases). +++=1 fmol target nucleic acid; ++=10 amol target nucleic acid; +=0.1 amol target nucleic acid; NTC=no target control. A band corresponding to the probe fragment F2 was visible in each of lanes 2, 3 and 4 evidencing sensitive detection of the target to the zeptomole range. No band was visible in lane 5 (NTC).

This example demonstrates that the method of the invention can be employed for highly sensitive detection through designing probe P1 to be capable of cross-priming. Further enhancement in sensitivity is obtained by increasing further the cross-priming capability and/or the number of nicking cleavage sites within the double-stranded nucleic acid amplifier. Therefore the sensitivity of the method can be increased or decreased as required for a particular application, based upon the copy number range of the target nucleic acid. This represents the powerful versatility of the method of the invention. No loss of specificity was observed in many experiments performed under different conditions. Step a) of the reaction was performed at just 32° C., significantly lower than recommended for known methods, and advantageous for integration into a low-cost testing device.

2.2. Exponential Amplification in Step a) with Extension of Oligonucleotide Probe P1.

In this embodiment the double-stranded nucleic acid amplifier is produced as illustrated in FIG. 2A, in that oligonucleotide probe P1 is extended by the polymerase to produce the double-stranded nucleic acid amplifier. Steps a), b) and c) of the reaction were performed sequentially and detection in step c) was performed by gel electrophoresis.

Firstly oligonucleotide probe P1 was designed to detect a viral DNA target comprising in the 5' to 3' direction 26 bases of single stranded DNA with the following sequence components: (i) 10 bases comprising the complementary sequence of a nicking agent recognition sequence and cleavage site capable of producing a displaced strand fragment (F1) that can act as a truncated template for P2; (ii) 9 bases comprising the complementary sequence of a nicking agent recognition sequence and cleavage site present within the target derived strand following production of the double-stranded nucleic acid amplifier; (iii) a further 13 bases sequence comprising the same 10 bases as (i) above; and the first three bases of (ii) above; and (iv) 18 bases of sequence that is complementary to the target nucleic acid. A double strand cleaving agent (a class II restriction endonuclease) was used as the first nicking agent and cleavage of P1 was blocked by use of a phosphorothioate base at the cleavage site (indicated by *). The following symbols are used to indicate the design of the probes: X=Nucleotide base (A, T, C, G) of the first nicking agent recognition site; Y=Nucleotide base (A, T, C, G) of the second nicking agent recognition site; B, C=Nucleotide base (A, T, C or G) with sequence designed to facilitate cross-priming and detection; D=Nucleotide base (A, T, C or G) of complementary bases to the target nucleic acid. The target contains the reverse complement of part of the sequence of P1 (indicated by alternative case); /=cleavage position.

```
P1:
5'YYYYYBBBB*BCCC_CxxxxxYYYYYBBBBBCCCDDDDDDDDDDDD*
DDDD_D-3'

Target:
3'-ddddddddddddd_dddd/dXXXXXd...5'
```

Following extension of oligonucleotide probe P1 by the polymerase in the presence of the target nucleic acid, a cleavage site for the first nicking agent is formed within the target when the complementary bases to the recognition sequence present in the target nucleic acid are synthesised. Additional sequence is also produced depending on the length of target nucleic acid to the 5' of its region of complementarity to P1. The exact length of this sequence (indicated by . . . ') depends on the length of the target nucleic acid and the length of the complementary sequence that is extended by the polymerase; however the only requirement for the method is that the extended sequence is of sufficient length such that an effective primer is produced from the target nucleic acid. The nicking agent cleavage site in the target nucleic acid is cleaved by the first nicking agent to produce a primer (3' dXXXXXd . . . 5') and, following extension by the polymerase, the double-stranded nucleic acid amplifier was produced of the following composition.

```
P1:
5'YYYYYBBBBBCCC_CxxxxxYYYYYBBBBBCCCDDDDDDDDDDDD*
DDDD_DxxxxxD...3'

TS:
3'yyyyybbbbbccc/cXXXXXyyyyybbbbbcccdddddddddddd_
dddd/dXXXXXd...5'
```

Oligonucleotide probe P2 was designed to contain in the 5' to 3' direction: (i) a 10 base nicking agent recognition sequence and cleavage site as in P1 but without the phosphorothioate base; (ii) a 3 base additional homology region to the displaced strand fragments; and (iii) 26 bases of sequence to facilitate detection of fragment F2, indicated by L.

```
P2:
5'-YYYYYBBBB/BCCCLLLLLLLLLLLLLLLLLLLLLLLLLL-3'
```

Based on the design of P1 and P2 outlined above, following production of the double stranded nucleic acid amplifier, the nicking agent cleaves the target derived strand in two places as indicated and subsequent extension by the polymerase displaces two strand fragments. One of the two strand fragments comprises the 13 base sequence denoted as 3'-yyyyybbbbbccc-5' (F1) which forms a truncated template which is capable of hybridising to P2 to form a cleavage site for the second nicking agent. It also has two potential binding sites within P1 allowing cross-priming leading to an enhanced amplification effect. The other strand fragment displaced from P1 comprises the 36 base sequence denoted as 3'-cXXXXXyyyyybbbbbcccdddddddddddddddd-5' which serves as a cross-priming fragment, since after it is displaced it will prime another molecule of probe P1 at the same relative position, yielding a secondary double-stranded nucleic acid amplifier capable of generating additional copies of F1. The sequential action of the polymerase and the nicking agent produces many copies of each of the two strands in an exponential step a) reaction. Fragment F1 hybridises to probe P2 to form the nicking agent cleavage site leading to the cleavage of P2 to produce the detection fragment F2 comprising the sequence 5'-BCC-CLLLLLLLLLLLLLLLLLLLLLLLLLL-3'. Due to target recycling, each copy of F1 leads to the cleavage of many copies of P2 to produce many copies of F2.

Reactions for step a) were prepared containing: 0.5 pmol probe P1; 1 U first nicking agent; various concentrations of dNTP; 1 U of Bst 3.0 polymerase (NEB) and 1 fmol target nucleic acid in a final volume of 10 µl containing 1× Isothermal Buffer II (NEB). Reactions were incubated at 37° C. for 15 min before inactivation of the polymerase by heating at 95° C. for 10 min. Reactions for step b) were then prepared containing 2 µl of the step a) reaction; 5 pmol probe P2; and 2.5 U second nicking agent, in a 10 µl total volume containing 1× Cutsmart buffer (NEB). Following incubation at 37° C. for 20 min the entire reactions were analysed by TBE-Urea polyacrylamide gel electrophoresis (PAGE) using a 15% w/v gel stained with SYBR Gold (Life Technologies) and visualised using a UV transilluminator.

Figure 4B:
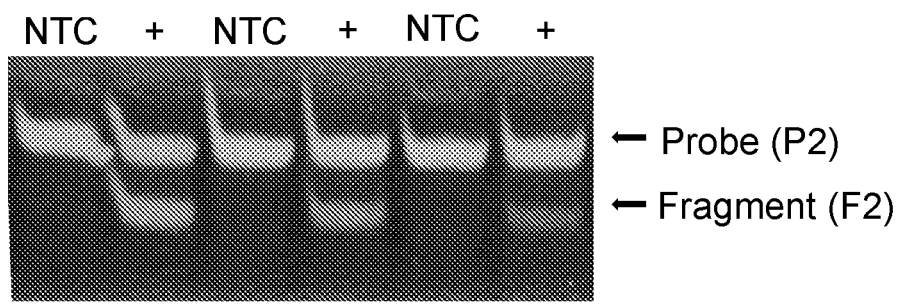
FIG. 4B. Exponential amplification in step a) with extension of oligonucleotide probe (P1) (see Example 2.2).

FIG. 4B displays a photograph of the stained polyacrylamide gel electrophoresis gel. +=1 fmol target nucleic acid; NTC=no target control. Reactions were performed at various dNTP levels; lanes 1 and 2=5 µM; lanes 3 and 4=15 µM; and 5 and 6=500 µM. A band corresponding to the probe fragment F2 was visible in each of the +lanes 2, 4 and 6 evidencing sensitive operation of the method and increased amplification at higher dNTP levels. No band was visible in NTC lanes 1, 3 and 5 evidencing no background signal was detected even at the highest dNTP level.

This example demonstrates that the method of the invention can be employed for sensitive detection through design of an extendable form of probe P1, demonstrating the versatility of the method. It is advantageous to have the option to generate the double stranded nucleic acid amplifier through extension of P1, as it provides for flexibility over the site for hybridisation of P1, whilst retaining the specificity arising from targeting a nicking agent cleavage site present in the target nucleic acid. Reducing the number of nicking agent cleavage sites in probe P1 and optimally selecting the strand orientation of the nicking agents, which is only possible using double-strand cleaving agents, allows the present invention to offer substantially improved resistance to background signal than known methods, as demonstrated by the lack of background signal even at high dNTP levels.

2.3. Time Course of Amplification and Comparison to PCR and LAMP.

In this embodiment the time course of amplification of a viral target nucleic acid by the method was performed in comparison to known methods PCR and LAMP. The double-stranded nucleic acid amplifier was produced as illustrated in FIG. 1, in that oligonucleotide probe P1 does not require extension and can be capped at the 3' end. Steps a), b) and c) of the reaction were performed sequentially and detection in c) was performed by gel electrophoresis.

Firstly oligonucleotide probe P1 was designed comprising in the 5' to 3' direction 52 bases of single stranded DNA with the following sequence components: (i) 2 copies of a 13 base sequence comprising the complementary sequence of a nicking agent recognition sequence and cleavage site capable of producing a displaced strand fragment (F1) that can act as a truncated template for P2; (ii) 10 bases comprising the complementary sequence of a nicking agent recognition sequence and cleavage site present within the target nucleic acid; and (iii) 16 bases of additional sequence complementary to the target nucleic acid. A single double strand cleaving agent (a class II restriction endonuclease) was used as both the first and second nicking agent and cleavage of P1 was blocked by use of a phosphorothioate base at the cleavage site (indicated by *). The following symbols are used to indicate the design of the probes: X=Nucleotide base (A, T, C or G) of the first nicking agent recognition site; B, C=Any nucleotide (A, T, C or G) with sequence designed to facilitate cross-priming and detection; D=Any nucleotide base (A, T, C or G) of complementarity to the target nucleic acid. The target nucleic acid contains the reverse complement of part of the sequence of P1 (indicated by lower case); /=cleavage position.

```
P1:
5'-BBBXXXXXC*CBBBBBBXXXXXC*CBBB_XXXXXD*DDDD_
DDDDDDDDDDDDDDDD-3'

Target:
3'-xxxxxd_dddd/dddddddddddddddd-5'
```

Following cleavage of the target nucleic acid to produce a primer and extension by the polymerase, the double-stranded nucleic acid amplifier was produced of the following composition. TS=target derived strand.

```
P1:
5'-BBBXXXXXC*CBBB_BBBXXXXXC*CBBB_XXXXXD*DDDD_
DDDDDDDDDDDDDDDD-3'

TS:
3'-bbbxxxxxc_cbbb/bbbxxxxxc_cbbb/xxxxxd_dddd/
dddddddddddddddd-5'
```

Oligonucleotide probe P2 was designed to contain in the 5' to 3' direction: (i) 27 bases of sequence for detection of fragment F2 by nucleic acid lateral flow, indicated by L; (ii) the same 10 base nicking agent recognition sequence and cleavage site as in P1 but without the phosphorothioate base, and (iii) an 6 base spacer; L=any nucleotide base (A, T, C or G) of a sequence designed to facilitate detection of F2; N=any nucleotide base (A, T, C or G) designed as a spacer sequence.

```
P2:
5'-LLLLLLLLLLLLLLLLLLLLLLLLLLLXXXXXC/
CBBBNNNNNN-3'
```

Following production of the double stranded nucleic acid amplifier, the nicking agent cleaves the target derived strand in three places as indicated and subsequent extension by the polymerase displaces three strand fragments. Two of the three strand fragments comprise the 13 base sequence denoted as 3'-bbbxxxxxccbbb-5' (F1) which forms the truncated template which is capable of hybridising to P2 to form a cleavage site for the nicking agent. These strands are capable of cross-priming to any of the three potential binding sites ('BBBXXXXX') within probe P1. The other strand fragment displaced from P1 comprises the 10 base sequence denoted as 3'-xxxxxddddd-5' which serves as a cross-priming fragment, since after it is displaced it will prime another molecule of probe P1, yielding a secondary double-stranded nucleic acid amplifier capable of generating additional copies of F1. The sequential action of the polymerase and the nicking agent produces many copies of each of the three strands in an exponential step a) reaction. Fragment F1 hybridises to P2 to form the nicking agent recognition site leading to the cleavage of P2 to produce the detection fragment F2 comprising the sequence 5'-LLLLLLLLLLLLLLLLLLLLLLLLLLLXXXXXC-3'. Due to target recycling, each copy of F1 leads to the cleavage of many copies of P2 to produce many copies of F2.

Reactions for step a) were prepared containing: 0.05 pmol probe P1; 1 U nicking agent; 3 µM dNTP and 1 U of Bst 2.0 polymerase (NEB) and either 1 fmol or 0.1 amol of target nucleic acid in a final volume of 10 µl containing 1× Isothermal Buffer (NEB). Reactions were incubated at 37° C. for up to 60 min before inactivation of the polymerase by heating at 95° C. for 10 min. Reactions for step b) were then prepared containing 2 µl of the step a) reaction; 5 pmol probe P2; and 2.5 U nicking agent, in a 10 µl total volume containing 1× Cutsmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 5:
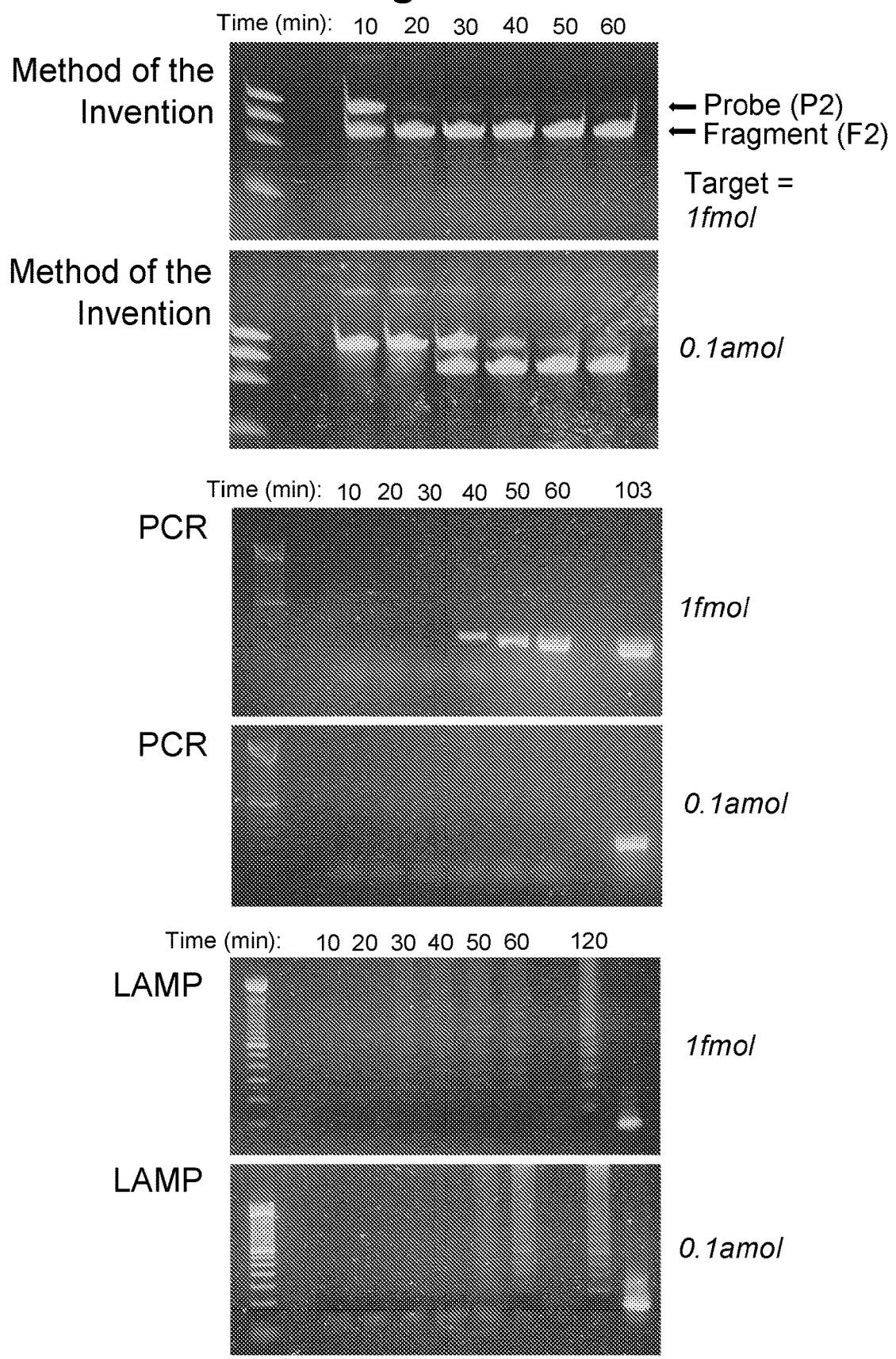
FIG. 5. Time course of amplification of the method of the invention and comparison to PCR and LAMP (see Example 2.3).

FIG. 5 displays photographs of the stained polyacrylamide gel electrophoresis gel displaying a time course of step a), with 10 min increments in lanes 3-8 as indicated. Lane 1 displays a size marker with (50, 40, 30 and 20 bases). Lane 2 is blank. Very rapid production of the oligonucleotide probe fragment F2 was observed, evidencing sensitive detection of the target, even at the lowest level of target nucleic acid. In order to compare the rate of amplification with known methods, an optimised assay for PCR and LAMP reported for the same virus were selected from published literature and used to generate a comparable time course of amplification. Samples were analysed from throughout a similar time course using 2% agarose gels. In the case of the final lane of the LAMP gels, a HinfI digest of the end-point reaction product was performed to verify the amplicon identity. LAMP assay was heated at 60° C., whilst the PCR assay was incubated at various temperatures as is standard.

This example demonstrates the powerful amplification potential of the method of the invention, with very rapid accumulation of the detected probe fragment F2 observed proving further evidence of its exceptional sensitivity. The probe cleavage band indicative of amplification using the method of the invention was visible after just 10, and 30 min at the 1 fmol, and 0.1 amol target levels, respectively, which is significantly faster that the comparator methods. PCR, the most widely researched and employed method in the field, was found to require 40 min and 103 min (end-point) before any amplified signal was detected on the gel, evidencing significantly slower amplification than the method of the invention. LAMP is widely used in the field as an isothermal alternative to PCR and was found to require 30 min and 50 min before amplified product was detected, again significantly slower than the method of the invention. Furthermore, given the undefined size of the amplified product resulting from LAMP amplification, a digest was subsequently required to confirm the identity of the amplified product before the result could be reliably interpreted (see right hand lane).

In addition to more rapid amplification observed compared to the most widely used comparator methods, the method of the invention exhibited simpler requirements in terms of the incubation temperature. PCR requires using many different temperatures which necessitates a machine for controlled temperature cycling. LAMP required incubation at 60° C. and was found to give no amplification at all in an equivalent experiment when the time course was performed at the same temperature employed for the method of the invention (i.e. 37° C.). Taken together these data evidence the powerful potential for the method of the invention to be employed in rapid detection of low levels of a given target nucleic acid, in a reaction with simple performance requirements, such as low temperature. Performance of integrated reactions of the method of the invention in which step a) and b) are performed simultaneously and colorimetric nucleic acid lateral flow is used in step c), further enhance sensitivity and have the potential to further improve the speed and sensitivity of detection. In addition to its sensitivity, again this example demonstrates the versatility of the method, its low temperature operation and its simplicity, with just a single double strand cleaving agent required.

Example 3

Investigation of Reaction Parameters

We have explored a number of parameters of the method of the invention. These examples demonstrate the versatility of the method in terms of, for example, reaction conditions, target type and detection modality.

3.1. Performance of the Method of the Invention at Different Temperatures

Our investigations with a range of variants of oligonucleotide probe P1 and P2 have revealed that the method of the invention operates over a broad temperature range, including unusually low temperatures compared to known methods without significant loss of reaction performance, such as sensitivity or specificity.

In this example, P1 was designed as follows:

```
P1:
5'-BBBXXXXXC*CCCCBBBXXXXXC*CCCCDDDDDDDDDD*DDDD_
D-3'

TS:
3'-dddddddddddd_dddd/dXXXXXd...5'
```

A double-stranded nucleic acid amplifier is produced of the following composition following the action of the first nicking agent and the polymerase. A single double-strand cleaving agent with recognition sequence indicated by 5'XXXXX3' (1/5) was employed as both the first and second nicking agent and cleavage of P1 was blocked by use of phosphorothioate bases at the cleavage site (indicated by *).

```
P1:
5'-BBBXXXXXC*CCCC_BBBXXXXXC*CCCC_DDDDDDDDDD*
DDDD_DxxxxxD...3'

Target:
3'-bbbxxxxxc_cccc/bbbxxxxxc_cccc/ddddddddddd_dddd/
dXXXXXd...5'
```

The same P2 as employed in Example 2.3 was used. Following production of the double stranded nucleic acid amplifier, the first nicking agent cleaves the target derived strand in three places as indicated and subsequent extension by the polymerase displaces three strand fragments. Two of the three strand fragments comprise the 13 base sequence denoted as 3'-bbbxxxxxccccc-5' (F1) which forms the truncated template which is capable of hybridising to P2 to form a cleavage site for the nicking agent. These strands are capable of cross-priming to any of the two potential binding sites ('BBBXXXXXCCCCC') within probe P1. The other strand fragment displaced from P1 comprises the 15 base sequence denoted as 3'-dddddddddddddd-5' which serves as a cross-priming fragment, since after it is displaced it will prime another molecule of probe P1, yielding a secondary double-stranded nucleic acid amplifier capable of generating additional copies of F1. The sequential action of the polymerase and the nicking agent produces many copies of each of the three strands in an exponential step a) reaction. Fragment F1 hybridises to P2 to form the nicking agent recognition site leading to the cleavage of P2 to produce the detection fragment F2 comprising the sequence 5'-LLLLLLLLLLLLLLLLLLLLLLLLLLLLLXXXXXC-3'. Due to target recycling, each copy of F1 leads to the cleavage of many copies of P2 to produce many copies of F2.

Reactions for step a) were prepared containing: 0.1 pmol probe P1; 1 U first nicking agent; 10 µM dNTP; 1 U of Bst 3.0 polymerase (NEB) and 1 fmol target nucleic acid in a final volume of 10 µl containing 1× Isothermal Buffer II (NEB). Reactions were incubated at various temperatures for 30 min before inactivation of the polymerase by heating at 95° C. for 10 min. Reactions for step b) were then prepared containing 2 µl of the step a) reaction; 5 pmol probe P2; and 2.5 U second nicking agent, in a 10 µl total volume containing 1× Cutsmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 6:
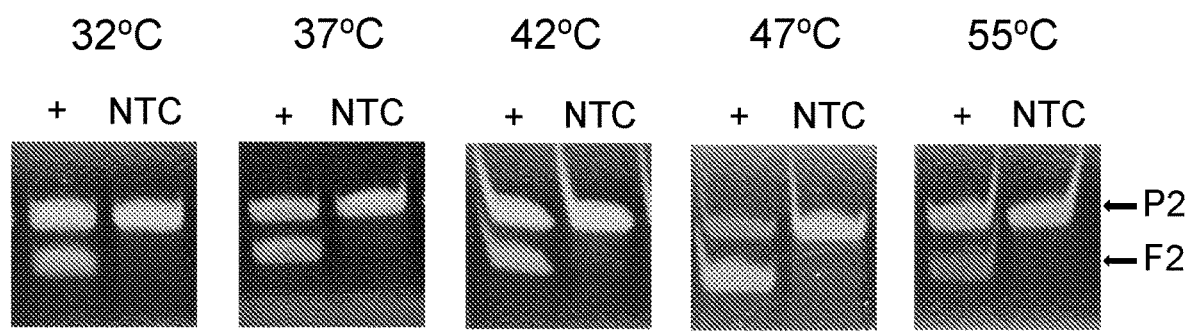
FIG. 6. Performance of the method of the invention at different temperatures (see Example 3.1).

FIG. 6 displays a photograph of the stained polyacrylamide gel electrophoresis gel. +=1 fmol target nucleic acid; NTC=no target control. A band corresponding to the probe fragment F2 was visible in each of the +lanes evidencing sensitive operation of the method over a wide range of temperatures. No band was visible in NTC lanes evidencing no background signal even at lower temperatures. It has been widely reported with known methods that low temperature operation can lead to non-specific background amplification. Therefore this example, demonstrates the robustness of the present invention in this regard.

3.2. Detection of Target Nucleic Acid Generated from Single Stranded RNA by the Action of Reverse Transcriptase When employing the method for the detection of naturally occurring RNA target, it may be preferable to perform a reverse transcriptase reaction to convert the RNA to a single-stranded DNA target either in a separate step prior to the method or in a single-pot reaction. In this example we demonstrate the detection of a single-stranded RNA target by first converting it to a single-stranded DNA through the use of reverse transcriptase with a separate reverse transcriptase primer upstream of the desired target site.

In this example a single-stranded viral RNA target of 1,600 bases was detected. The viral RNA target was synthesised artificially from synthetic double stranded DNA. PCR reactions were then performed to amplify these fragments to incorporate a T7 RNA polymerase promoter sequence onto either 'end' of the PCR amplicon. In this way PCR product was produced and used as an input into a T7 based in vitro transcription kit (Life Technologies TranscriptAid T7 High Yield in vitro transcription (IVT) kit) to generate a single-strand full-length RNA transcript, of either strand.

The reverse transcriptase primer was designed with 20 bases of sequence complementarity between base positions 170 and 189 of the RNA, such that following its extension it would generate a cDNA of 189 bases which formed the 'target nucleic acid' for the method. P1 was designed using similar design parameters to Example 2.2 above. The region of target complementarity (designated by 'D') was designed to contain the same sequence as the RNA bases 79-94, such that it would have complementary to the cDNA target between bases 96 and 111 immediately upstream of the nicking agent recognition sequence present within the target. P1 was constructed with the following composition:

P1:
5'-YYYYYBBBBBXXXXXC*CCCC_YYYYYBBBBBNNNDDDDDDDDDD*DDDD_D-3'

Target:
3'-dddddddddd_dddd/dXXXXXd...5'

A double-strand cleaving agent with recognition sequence indicated by 5'XXXXX3' (1/5) was employed as the first nicking agent and cleavage of P1 was blocked by use of phosphorothioate bases at the cleavage site (indicated by *). A double-stranded nucleic acid amplifier is produced of the following composition following the action of the first nicking agent and the polymerase.

P1:
5'-YYYYYBBBBBXXXXXC*CCCC_YYYYYBBBBBNNNDDDDDDDDDD*DDDD_DxxxxxD...3'

TS:
3'-yyyyybbbbbxxxxxc_cccc/yyyyybbbbbnnndddddddddd_dddd/dXXXXXd...5'

The same P2 as employed in Example 2.1 was used. A double-strand cleaving agent with recognition sequence indicated by 5'YYYYY3' (4/5) was employed as the second nicking agent with the displaced fragment F1 producing a truncated template for the second nicking agent. ' . . . ' again denotes additional sequence of length at least sufficient for the target nucleic acid to form an effective primer following extension of P1 by the polymerase.

Following production of the double stranded nucleic acid amplifier, the first nicking agent cleaves the target derived strand in two places as indicated and subsequent extension by the polymerase displaces two strand fragments. One of the two strand fragments comprise the 20 base sequence denoted as 3'-yyyyybbbbbxxxxxccccc-5' (F1) which forms the truncated template which is capable of hybridising to P2 to form a cleavage site for the nicking agent. This strand is capable of cross-priming to either of the two potential binding sites ('YYYYYBBBBB') within probe P1. The other strand fragment displaced from P1 comprises the 28 base sequence denoted as 3'-yyyyybbbbbnnnddddddddddddddd-5' which serves as a cross-priming fragment, since after it is displaced it will prime another molecule of probe P1, yielding a secondary double-stranded nucleic acid amplifier capable of generating additional copies of F1. It also contains the necessary sequence to act as a truncated template for P2. The sequential action of the polymerase and the nicking agent produces many copies of each of the two strands in an exponential step a) reaction. Fragment F1 hybridises to P2 to form the nicking agent recognition site leading to the cleavage of P2 to produce the detection fragment F2 comprising the sequence 5'-DDDDLLLLLLLLLLLLLLLLLLLLL-3'. Due to target recycling, each copy of F1 leads to the cleavage of many copies of P2 to produce many copies of F2.

Firstly a reverse transcriptase reaction was performed containing: 200 U Superscript III (Life Technologies); 40 U RNase inhibitor (NEB); 10 mM DTT; 800 ng RNA target and 2.5 pmol of reverse transcriptase primer in 1× of First Strand buffer (Life Technologies). Following incubation at 42° C. for 60 min the enzyme was inactivated by heating the reaction at 95° C. for 10 min. Reactions for step a) were prepared containing: 0.5 pmol probe P1; 1 U first nicking agent; 10 µM dNTP; 1 U of Bst 3.0 polymerase (NEB) in a final volume of 10 µl containing 1× Isothermal Buffer II (NEB). Reactions were incubated at various temperatures for 30 min before inactivation of the polymerase by heating at 95° C. for 10 min. Reactions for step b) were then prepared containing 2 µl of the step a) reaction; 5 pmol probe P2; and 2.5 U second nicking agent, in a 10 µl total volume containing 1× CutSmart buffer (NEB). Following incubation at 37° C. for 20 min the entire reactions were analysed by TBE-Urea polyacrylamide gel electrophoresis (PAGE) using a 15% w/v gel stained with SYBR Gold (Life Technologies) and visualised using a UV transilluminator.

Figure 7A:
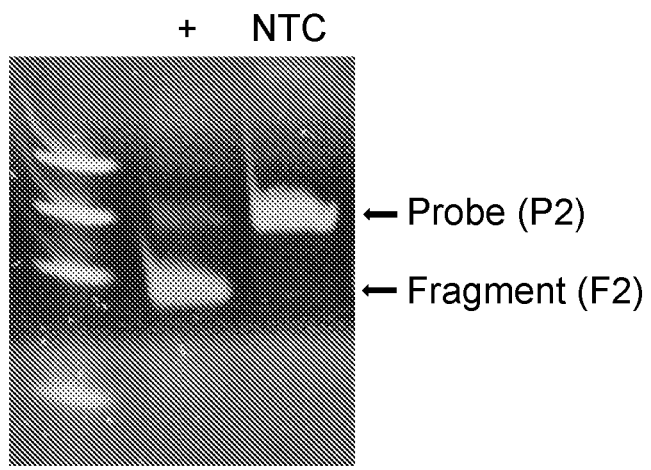
FIG. 7A. Detection of target nucleic acid generated from single stranded RNA by the action of reverse transcriptase (see Example 3.2).

FIG. 7A displays a photograph of the stained polyacrylamide gel electrophoresis gel. +=target nucleic acid; NTC=no target control. A band corresponding to the probe fragment F2 was visible in the +lane evidencing that each step of the process had been successfully performed. No band corresponding to F2 was visible in the NTC lane evidencing no background signal. Whilst the reaction in this example was conducted sequentially, the conditions of the various steps (temperature, buffer etc.) are compatible and the reactions may therefore be readily integrated such that they are performed simultaneously. This example demonstrates the versatility of the method for integration with a reverse transcription reaction for use in the detection of RNA targets.

3.3. Single-Stranded RNA as Target Nucleic Acid

When employing the method for the detection of a natural RNA target, it may be preferable to directly target RNA using oligonucleotide probe P1 as the reverse transcriptase primer. In such an embodiment of the invention, a separate target nucleic acid primer is required such as illustrated in FIG. 2B. In this example, RNA of reverse complementary sequence to that used in Example 3.2 was employed as the target nucleic acid. It was synthesised by in vitro transcription as described in Example 3.2, but with the T7 promotor inserted by PCR at the opposite end of the double stranded nucleic acid. The same probes P1 and P2 were used as in Example 3.2:

```
P1:
5'YYYYYBBBBBXXXXXC*CCCC_YYYYYBBBBBNNNDDDDDDDDDD*
DDDD_D...3'

Target:
3'...dddddddddd_dddd/dXXXXXd...5'
```

Following extension of P1 and removal of the RNA target nucleic acid, which may occur by RNase H activity, denaturation or disassociation, an extended form of P1 is produced which comprises the following sequence, which may comprise an extensive 3' region depending on the read-length of the reverse transcriptase:

```
P1:
5'YYYYYBBBBBXXXXXC*CCCC_YYYYYBBBBBNNNDDDDDDDDDD*
DDDD_DxxxxxDDDDDDDDDDDDDDDDDDDDDDDDDDDDDD...-3'
```

A 15 base target nucleic acid primer was designed to hybridise to the P1 derived strand, to the location indicated by double underlining on the extended P1 primer above. Following extension of the target nucleic acid primer, the double stranded nucleic acid amplifier below is produced. Note: The full sequence to the 3' of P1 that includes the full target nucleic acid primer binding site is not displayed. '...' denotes the additional 11 bases of the target nucleic acid primer sequence and its reverse complement within the P1 derived strand.

```
P1:
5'YYYYYBBBBBXXXXXC*CCCC_YYYYYBBBBBNNNDDDDDDDDDD*
DDDD_DxxxxxDDDDDDDD...3'

TS:
3'yyyyybbbbbxxxxxc_cccc/yyyyybbbbbnnnddddddddddd_
dddd/dXXXXXdddddddd...5'
```

The same P2 as employed in Example 2.1 was used. A double-strand cleaving agent with recognition sequence indicated by 5' YYYYY3' (4/5) was employed as the second nicking agent with the displaced fragment F1 producing a truncated template for the second nicking agent.

Following production of the double-stranded nucleic acid amplifier, the first nicking agent cleaves the target derived strand in two places as indicated and subsequent extension by the polymerase displaces two strand fragments. One of the two strand fragments comprise the 20 base sequence denoted as 3'-yyyyybbbbbxxxxxccccc-5' (F1) which forms a truncated template which is capable of hybridising to P2 to form a cleavage site for the nicking agent. This strand is capable of cross-priming to either of the two potential binding sites ('YYYYYBBBBB') within probe P1. The other strand fragment displaced from P1 comprises the 28 base sequence denoted as 3'-yyyyybbbbbnnnddddddddddddddd-5' which serves as a cross-priming fragment, since after it is displaced it will prime another molecule of probe P1, yielding a secondary double-stranded nucleic acid amplifier capable of generating additional copies of F1. It also contains the necessary sequence to act as a truncated template for P2. The sequential action of the polymerase and the nicking agent produces many copies of each of the two strands in an exponential step a) reaction. Fragment F1 hybridises to P2 to form the nicking agent recognition site leading to the cleavage of P2 to produce the detection fragment F2 comprising the sequence 5'-DDDDLLLLLLLLLLLLLLLLLLLLL-3'. Due to target recycling, each copy of F1 leads to the cleavage of many copies of P2 to produce many copies of F2.

A reaction was performed containing: 200 U MMuLV reverse transcriptase; 8 U RNase inhibitor (NEB); 1 U first nicking agent; 1 U Bst 3.0 (NEB); 500 µM dNTP; 0.5 pmol P1; 0.5 pmol target nucleic acid primer and 100 ng RNA target in 1× of Isothermal buffer II (NEB). Following incubation at 37° C. for 40 min the enzyme was inactivated by heating the reaction at 95° C. for 10 min. Reactions for step b) were then prepared containing 2 µl of the step a) reaction; 5 pmol probe P2; and 2.5 U second nicking agent, in a 10 µl total volume containing 1× CutSmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 7B:
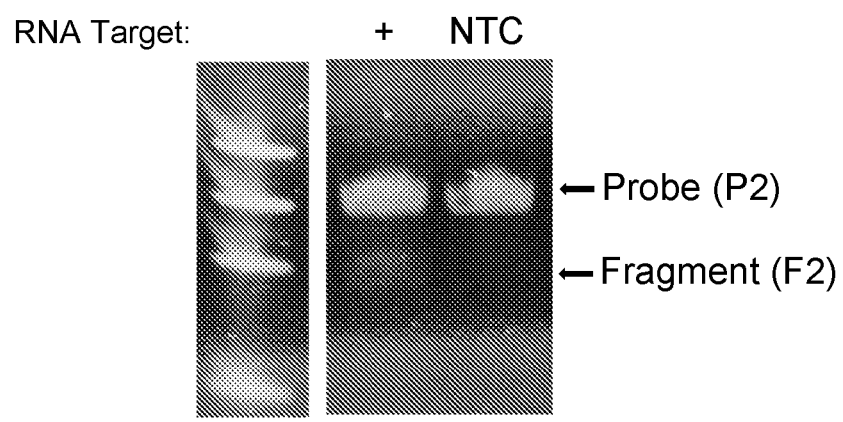
FIG. 7B. Single-stranded RNA as target nucleic acid (see Example 3.3).

FIG. 7B displays a photograph of the stained polyacrylamide gel electrophoresis gel. +=target nucleic acid; NTC=no target control. A band corresponding to the probe fragment F2 was visible in the +lane evidencing the direct detection of RNA by the method. No band corresponding to F2 was visible in the NTC lane evidencing no background signal. This example demonstrates the versatility of the method. Using the oligonucleotide probe P1 as a reverse transcriptase primer for the direct detection of RNA targets provides additional flexibility. It allows the sequence of a natural RNA to be targeted directly without having to target the opposite strand that results from cDNA production. For example, either strand of a nicking agent cleavage site can be exploited for optimal performance of the method to enhance the specificity and efficiency of the reaction. This example, which uses an additional target nucleic acid primer, also highlights the range of different embodiments of the method, in terms of production of the double strand nucleic acid amplifier. An alternative embodiment, for example, with enhanced amplification effect, may include introducing an additional nicking agent cleavage site into the target nucleic acid primer.

3.4. Testing of Alternative Nicking Agents

A wide range of different nicking agents can be employed in the method. In this example, we selected three enzymes with different properties for use as the first nicking agent to demonstrate the versatility of the method in this regard. The enzymes selected were AlwI, a double strand cleaving restriction endonuclease with recognition sequence 5'GGATC3' (4/5), BcoDI, a double strand cleaving restriction endonuclease with recognition sequence 5'GTCTC3' (1/5) and Nt.BstNBI, a nicking endonuclease with recognition sequence 5'GAGTC3' (5/–). Oligonucleotide probe P1 variants were designed following the design parameters described in Example 2. Each probe P1 was designed for use with the same second nicking agent and oligonucleotide probe P2 employed in Example 2.3.

Reactions for step a) for each alternative first nicking agent were performed as follows: AlwI: 1 U AlwI (NEB); 1 U Bst 2.0 (NEB); 0.1 pmol P1; 1 µM dNTP in 10 µl 1× Cutsmart buffer (NEB). Incubation for 30 min at 55° C.

BcoDI: 1 U BcoDI (NEB); 1 U Bst 3.0 (NEB); 0.1 pmol P1; 10 µM dNTP in 10 µl 1× Isothermal II Buffer (NEB). Incubation for 60 min at 37° C.

Nt.BstNBI: 1 U Nt.BstNBI (NEB); 1 U Bst 2.0 (NEB); 0.1 pmol P1; 1 µM dNTP in 10 µl 1× Isothermal Buffer (NEB). Incubation for 20 min at 55° C.

Following incubation each reaction was heated at 95° C. for 10 min to denature the enzymes. Reactions for step b) were then prepared containing 2 µl of the step a) reaction; 5 pmol probe P2; and 2.5 U second nicking agent, in a 10 µl total volume containing 1× CutSmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 8A:
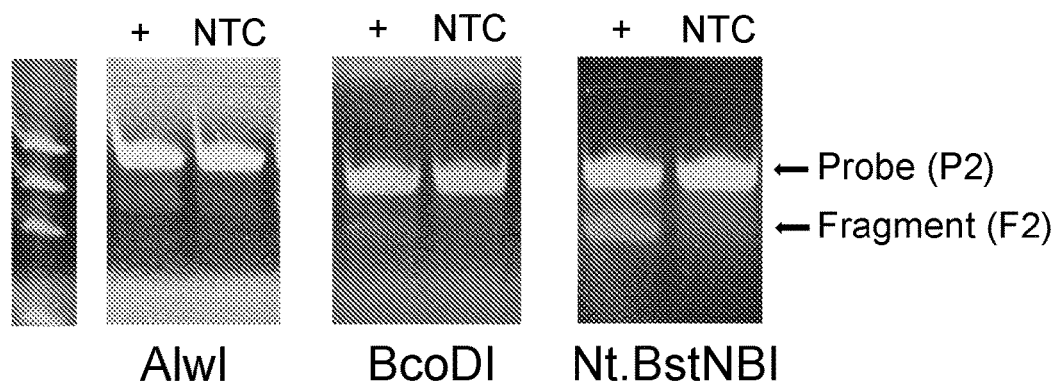
FIG. 8A. Testing of alternative nicking agents (see Example 3.4).

FIG. 8A displays photographs of the stained polyacrylamide gel electrophoresis gels obtained. +=target nucleic acid at 1 fmol in the case of AlwI and BcoDI and 5 fmol in the case of NtBstNBI; NTC=no target control. A band corresponding to the probe fragment F2 was visible in the +lane in each evidencing the efficient performance of the method with a range of alternative nicking agents in step a). This example demonstrates that it is possible to readily develop variants of the method for different nicking agents, which is particularly valuable for embodiments of the invention that target a restriction enzyme binding site within a natural target. Because a wide range of nicking agents with different recognition sequences can be employed, including double strand cleaving restriction endonucleases (see Example 3.10), a commercially available restriction enzyme for almost any given target nucleic acid sequence can be selected. Separately we have tested a wide range of nicking agents, including double strand cleaving agents (Example 3.10) and nicking endonucleases (Example 3.11) in the performance of step b) of the method which together evidences the versatility of the method with regard to the nicking agent(s) employed therein.

3.5. Testing of Alternative Polymerases

A wide range of different polymerases can be employed in the method. In this example, we selected four different polymerases to demonstrate the versatility of the method in this regard. The enzymes selected were Bst Large Fragment, Bst 2.0, Bst 3.0 and Bsu, each of which was obtained from New England Biolabs. Oligonucleotide probe P1 and P2 variants as described in Example 2.3 were employed for the detection of a viral nucleic acid target and a single nicking agent (a class II double strand cleaving restriction endonuclease) was employed as both the first and the second nicking agent in the method.

Reactions for step a) for each polymerase was performed as follows:

Bst Large Fragment: 1 U First nicking agent (NEB); 1 U Bst Large Fragment (NEB); 0.05 pmol P1; 1 µM dNTP in 10 µl 1× ThermoPol Buffer (NEB).

Bst 2.0: 1 U First nicking agent (NEB); 1 U Bst 2.0 (NEB); 0.05 pmol P1; 1 µM dNTP in 10 µl 1× Isothermal Buffer (NEB).

Bst 3.0: 1 U First nicking agent (NEB); 1 U Bst 3.0 (NEB); 0.1 pmol P1; 1 µM dNTP in 10 µl 1× Isothermal II Buffer (NEB).

Bsu: 1 U First nicking agent (NEB); 1 U Bsu Polymerase (NEB); 0.05 pmol P1; 1 µM dNTP in 10 µl 1×NEB 2.1 Buffer (NEB).

All reactions were incubated at 37° C. for 30 min. Following incubation each reaction was heated at 95° C. for 10 min to denature the enzymes. Reactions for step b) were then prepared containing 2 µl of the step a) reaction; 5 pmol probe P2; and 2.5 U second nicking agent, in a 10 µl total volume containing 1× CutSmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 8B:
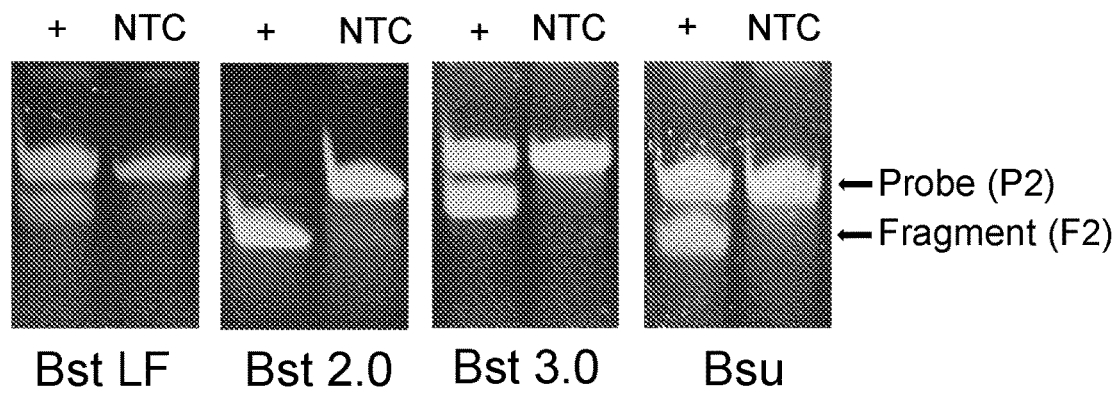
FIG. 8B. Testing of alternative polymerases (see Example 3.5).

FIG. 8B displays photographs of the stained polyacrylamide gel electrophoresis gels obtained. +=target nucleic acid at 1 fmol; NTC=no target control. A band corresponding to the fragment F2 was visible in the +lane in each case evidencing the efficient performance of the method with a range of alternative polymerases in step a). This example demonstrates that it is possible to readily adopt different polymerases for use in the method, which is valuable in that it presents a range of options from which to select the optimal enzyme for a particular reaction dependent on other parameters. For example, a polymerase that has a similar temperature and buffer preference to the nicking agent(s) to be employed in the reaction can be selected. The availability of polymerases for use in the method with activity over a wide temperature range, enables the method to be performed at any desired temperatures provided the relevant complementarity regions of probes P1 and P2 are designed to have appropriate Tm's and a nicking agent is also identified for the desired temperature (see Example 3.4). Preferably the method may be performed at low temperatures e.g. 20-40° C. which simplifies (or removes) the requirement and cost of any device or hardware employed in the performance of the method. More broadly, this example evidences the versatility of the method with regard to the polymerase employed therein.

3.6. Detection of target in the presence of excess nucleic acid material

A number of intended applications for the invention require the detection of a target nucleic acid sequence within a sample which is or may be contaminated with an excess of other nucleic acid(s). For example, large excesses of DNA or RNA may be present within the sample from organisms other than the intended target organism. In order to test whether such non-specific nucleic acid might lead to complications in the performance of the method (e.g. non-specific background amplification and/or interference in the reaction that occurs in the presence of target nucleic acid), we performed a number of experiments in the presence of a high level of spiked contaminating DNA (Herring Sperm DNA) or RNA (Tortula Yeast RNA extract).

Reactions were performed using the same probes P1 and P2 described in Example 3.2, with a viral DNA nucleic acid target. A single double-strand cleaving agent (a class II restriction endonuclease) was employed as both the first and second nicking agent. Reactions were prepared containing: 1 U nicking agent; 1 U Bst 3.0; 0.5 pmol P1; 500 µM dNTP and 5 fmol target nucleic acid in 10 µl of 1× Isothermal II buffer. Selected reactions were spiked with either 100 ng Herring Sperm DNA or with Tortula Yeast Extract. Reactions were incubated at 37° C. for 15 min before being terminated by heating at 95° C. for 10 min. Reactions for step b) were then prepared containing 2 µl of the step a) reaction; 5 pmol probe P2; and 2.5 U second nicking agent, in a 10 µl total volume containing 1× CutSmart buffer (NEB). Following incubation at 37° C. for 30 min, the entire reactions were analysed by TBE-Urea polyacrylamide gel electrophoresis (PAGE) using a 15% w/v gel stained with SYBR Gold (Life Technologies) and visualised using a UV transilluminator.

Figure 9:
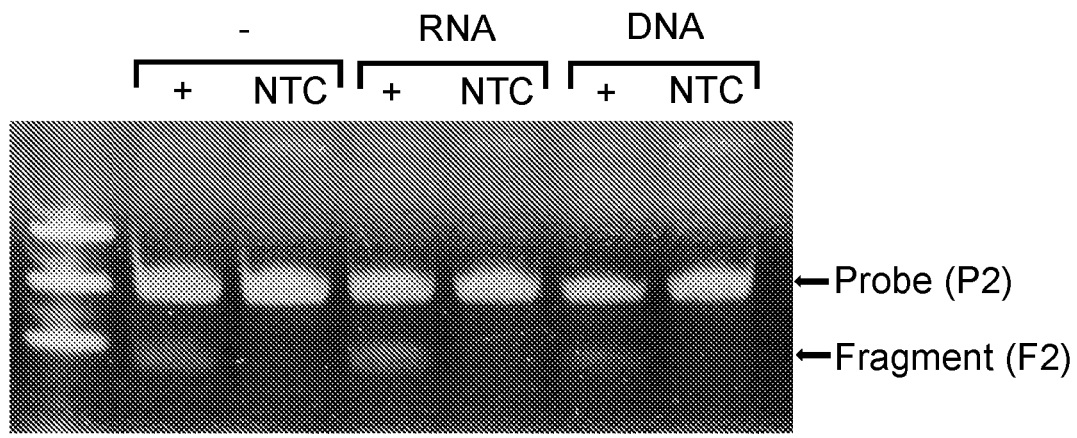
FIG. 9. Detection of target in the presence of excess nucleic acid material (see Example 3.6).

Results are displayed in FIG. 9. No non-specific background was observed in the no target control (NTC) lane in each case. Further in the presence of high levels of contaminating material, no significant loss of efficacy of the reaction was observed, in that the intensity of the F2 cleavage product bands were comparable to that observed in the absence of contaminant. This example evidences the high specificity of the method and its potential for application for use in complex samples, such as clinical or environmental samples, where low levels of target nucleic acids may be present alongside high levels of contaminating substances.

3.7. Colorimetric Detection with One Oligonucleotide Probe Attached to a Solid Material (Streptavidin Magnetic Beads) and to a Colorimetric Dye (Gold Nanoparticles)

We performed an experiment in order to demonstrate the accumulation of colorimetric signal that can be employed in the method with an oligonucleotide probe conjugated to gold nanoparticles. In order to do this, an oligonucleotide probe SEQ1, containing a 3' thiol modification and a 5' biotin moiety was first reduced using TCEP, as described in the general methods section. The oligonucleotide was then conjugated to maleimide activated 40 nm diameter gold nanoparticles (Innova Biosciences) by reacting 2 mg of gold nanoparticles with 1.6 nmol of thiol activated oligonucleotide in 45 µl of reaction buffer for 90 min at room temperature, according to the manufacturer's instructions. The reaction was then quenched by the addition of the quenching reagent provided and subsequently incubated for 20 min at room temperature with gentle agitation. Next, the conjugate gold solution was centrifuged at 7,500×g for five minutes. Supernatant was removed from the conjugated nanoparticles, which were subsequently re-suspended in 200 µl of 1×BW buffer, vortexed for ten seconds and centrifuged at 7,500×g for 5 min. This wash procedure was repeated a total of three times at which point the gold was re-suspended in 50 µl of BW buffer.

Figure 10:
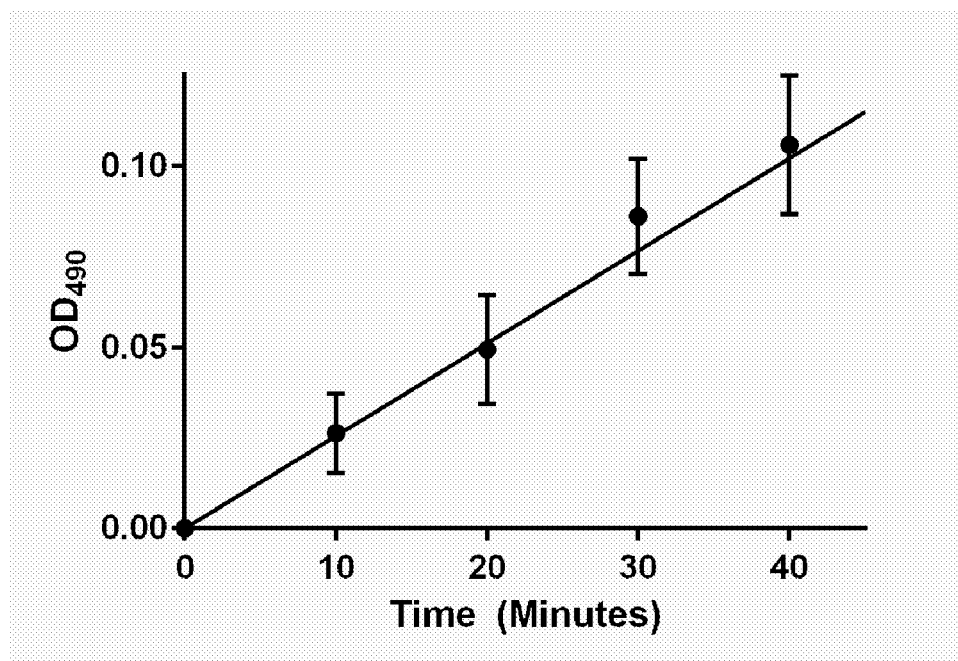
FIG. 10. One oligonucleotide probe (P2) attached to a solid material (streptavidin magnetic beads) and to a colorimetric moiety (gold nanoparticles) (see Example 3.7).

In order to couple the oligonucleotide to a solid material and consequently remove the nanoparticles from the aqueous solution, 30 µl of the conjugate containing approximately $4 \times 10^{14}$ nanoparticles, was incubated with 1.8 mg of Dynabeads (C1, streptavidin magnetic beads, Life Technologies) in a final volume of 300 µl of BW buffer at room temperature for 10 min with gentle agitation. Conjugated beads were then transferred to 1× buffer 3.1 (NEB). Triplicate oligonucleotide probe cleavage reactions were prepared containing 0.6 mg of conjugated beads, 50 U Nt.BstNBI (NEB), 10 µl 10× buffer 3.1 (NEB), 0.125 pmol of target nucleic acid (SEQ2) and dH$_2$O to a final reaction volume of 100 µl. Oligonucleotide probe cleavage reactions were incubated at 55° C. for 50 min. During the incubation reaction, absorbance readings at 490 nm were measured at ten minute intervals over the course of the reaction, following removal of beads from the reaction using a magnet. The results (displayed in FIG. 10, demonstrate a linear progression of colorimetric signal during the course of the oligonucleotide probe cleavage reaction ($R^2$=0.9851). Importantly, this evidences the ability to generate a visible colorimetric signal for detection of probe fragments produced in the performance of the method.

Figure 11A:
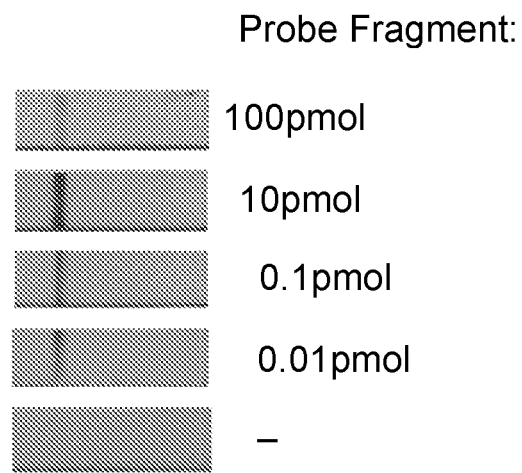
FIG. 11A. Colorimetric detection by nucleic acid lateral flow with gold nanoparticles (see Example 3.8).
Figure 11B:
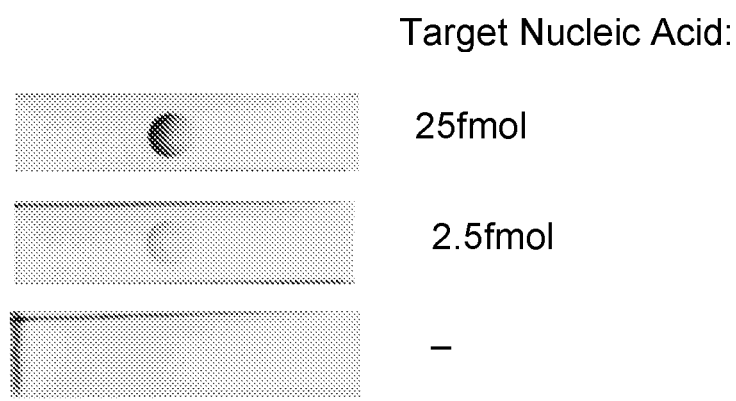
FIG. 11B. Colorimetric detection by nucleic acid lateral flow with carbon nanoparticles (see Example 3.9).

3.8. Colorimetric Detection by Nucleic Acid Lateral Flow with Gold Nanoparticles In order to demonstrate one approach for integration of the method with colorimetric lateral flow read-out, we have prepared gold nanoparticles conjugated to an oligonucleotide probe. 20 nm gold nanoparticles (BioAssay Works) were conjugated to oligonucleotide probe SEQ3 with a thiol modification on the 5' end, using sodium chloride salt-aging. After washing into PBS containing 0.01% (w/v) Tween-20, the gold nanoparticles were pipetted onto the conjugate pad of gRAD lateral flow strips (BioPorto) and air-dried. Various quantities of complementary oligonucleotide, SEQ4, synthesised with biotin on the 5' end, were applied to the lateral flow strips in the manufacturer's recommended running buffer and results were recorded by photography following signal development. Results are displayed in FIG. 11A. A clear visible band appeared on the lateral flow strips only in the presence of the oligonucleotide SEQ4, which hybridises to the SEQ3-conjugated gold nanoparticles deposited on the conjugate pad and flows along the strip before localising at the biotin-binding protein band printed on the nitrocellulose. This example clearly demonstrates one approach to using colorimetric lateral flow for the detection of probe fragments produced in the method. Oligonucleotide SEQ4 represents a biotinylated probe fragment that would be generated during the performance of the method and can be rapidly detected by colorimetric signal at low concentration.

3.9. Colorimetric Detection by Nucleic Acid Lateral Flow with Carbon Nanoparticles In order to demonstrate another approach for integration of the method with a colorimetric lateral flow read-out, we used carbon lateral flow strips prepared as described in the general methods section for sensitive colorimetric detection of probe fragments. An oligonucleotide probe containing the recognition sequence and cleavage site for a double-strand cleaving restriction endonuclease and synthesised with a biotin group on the 5' end was covalently attached to beads following standard protocols. 50 µg beads were incubated at 37° C. for 10 min in a 10 µl reaction containing 20 U of the relevant restriction enzyme, 1 µl of 10× reaction buffer and various concentrations of an oligonucleotide representing the probe fragment that would be produced from the preceding oligonucleotide probe in the method. Following incubation, 60 µl running buffer was added and each reaction was analysed by applying the entire contents of the reaction onto the sample pad of a lateral flow strip. The nitrocellulose membrane of the lateral flow strip was printed with an oligonucleotide containing the reverse complement to the probe fragment released from the bead following cleavage. A photograph of the nitrocellulose membrane following development of the lateral flow strips is displayed in FIG.

11B. Colorimetric signal was only observed in the presence of target nucleic acid and with increasing intensity as the level of target nucleic acid increases. This example demonstrates that carbon-based colorimetric nucleic acid lateral flow detection can be readily integrated for detection of the probe fragments produced in the method, in a simple, low-cost, rapid and sensitive assay format with no requirement for downstream extraction and processing of the reaction.

3.10. Use of Double-Strand Cleaving Agents in the Performance of the Method

In this example we have performed a series of experiments to demonstrate the use of double-strand cleaving agents for the performance of the method using a variety of different enzymes and approaches. We have demonstrated that restriction endonucleases that are capable of cleaving both strands of double-stranded DNA can exhibit a strand preference that permits them to function as nicking agents. We have also demonstrated that such restriction endonucleases can also function as nicking agents when one of the two cleavage sites within the double-stranded nucleic acid is not capable of being cleaved by use of a truncated template or a modification to protect it from nuclease cleavage, e.g. by use of a phosphorothioate (PTO) internucleotide bond.

In order to demonstrate the use of double-strand cleaving agents as nicking agents we have performed a series of probe cleavage reactions with oligonucleotide probes containing various permutations of the restriction recognition sequence and cleavage site(s) of three double-strand cleaving restriction endonucleases: FolI (NEB), BbsI (NEB) and BccI (NEB).

Firstly, we designed oligonucleotide probes for FokI and BbsI wherein the cleavage site of either the top or the bottom strand was protected by use of a PTO. We also synthesised the truncated template variant and the full-length unmodified form of each oligonucleotide probe. Cleavage reactions were assembled with 5 pmol of each oligonucleotide probe, 5 U of the relevant enzyme, 1 µl of 10× Cutsmart buffer (NEB), 0.05 pmol of a reverse complement oligonucleotide as the target (PTO modified, or truncated template (TT) variant as appropriate) and dH$_2$O to a final reaction volume of 10 µl. A control with no target was also performed. Reactions were incubated for 1 hour at the recommended assay temperature.

Figure 12A:
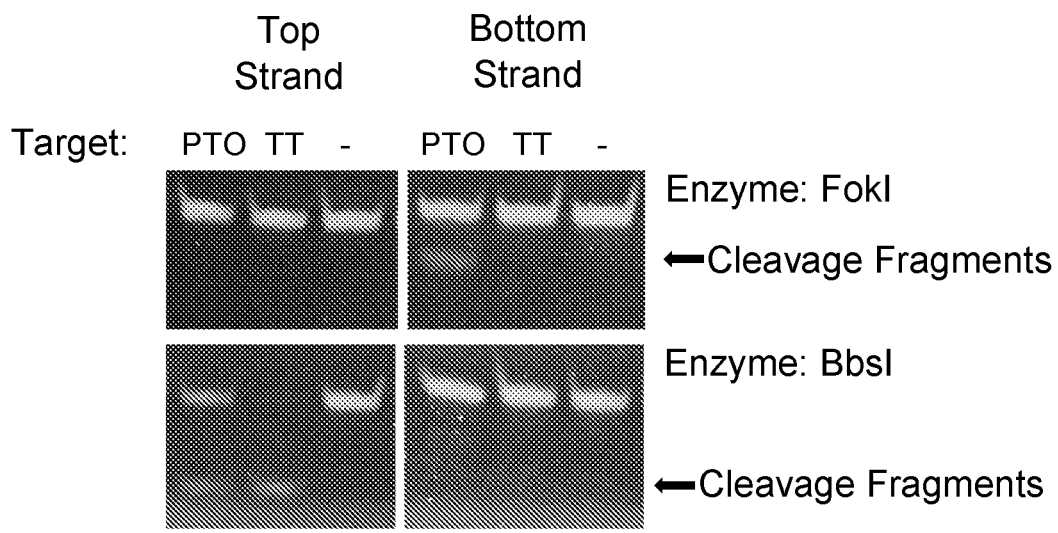
FIG. 12A, FIG. 12B and FIG. 12C. Use of double-strand cleaving agents in the performance of the method of the invention (see Example 3.10).
Figure 12B:
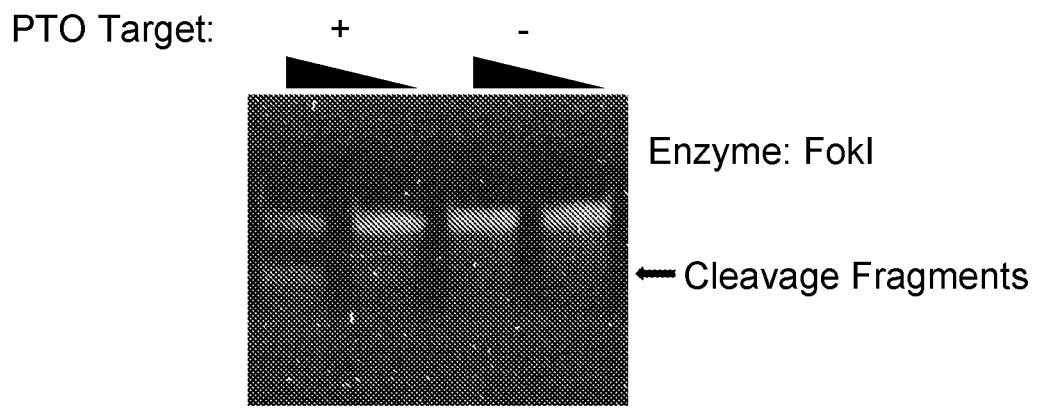

The results are shown in FIG. 12A, with lanes loaded as indicated. In the case of FoId, oligonucleotide probe cleavage was only observed with the bottom strand, demonstrating the strand preference of the FoId enzyme. In contrast BbsI demonstrated a 'top' strand preference. Strikingly in the case of BbsI, almost complete digestion of the oligonucleotide probe was observed in the reaction in which the top strand truncated template was used. Further cleavage reactions were performed for FokI bottom strand cleavage at 0.5 pmol and 0.05 pmol of template following the same protocol. The results are displayed on FIG. 12B and demonstrate that, whilst the enzyme does yield detectable signal solely as a result of strand preference, the sensitivity of the reaction is further enhanced by use of the PTO template. Taken together, these experiments demonstrate that double strand cleaving agents such as FokI and BbsI can be employed as nicking agents for the performance of the method as a result of their strand preference, by use of PTO and/or a truncated template.

Figure 12C:
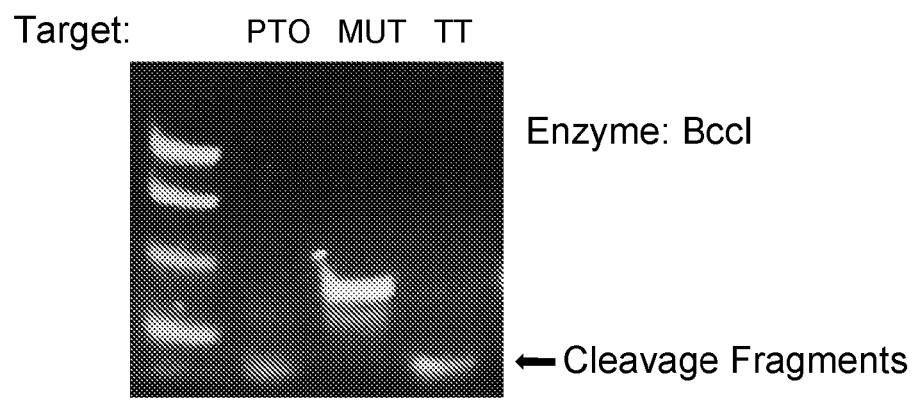

In a similar experiment we have also demonstrated that BccI can also be employed as a nicking agent using either a truncated template or a template which has been PTO modified. Digestion reactions were performed containing 5 pmol of an oligonucleotide probe, SEQ5, containing the top strand of the BccI restriction recognition and cleavage site, 0.05 pmol of either a PTO protected template (SEQ6), a mutated form of the PTO protected template (SEQ7) or a truncated template variant of the template (SEQ8), 5 U BccI (NEB), 1 µl of 10× Cutsmart buffer (NEB) and dH$_2$O to a reaction volume of 10 µl. Results are shown in FIG. 12C. The first lane was loaded with a size marker. The second lane was loaded with the reaction containing the full length PTO modified template, the third with the equivalent template containing a single base mismatch in the recognition sequence and the fourth lane with the reaction where a truncated template was used. Oligonucleotide probe cleavage bands were clearly visible in the first and fourth lanes but not the third lane, demonstrating that BccI can also efficiently utilise a truncated template or a PTO modified template and function as a nicking agent for use in the method.

This example demonstrates that double strand cleaving restriction endonucleases can function efficiently as nicking agents for use in the method, using strand preference, a truncated template and/or modification of the oligonucleotide backbone to make it resistant to nuclease cleavage, e.g. by use of phosphorothioate internucleotide linkage(s). The impact of these results is highly significant in that many double-strand cleaving restriction endonucleases, of which a much greater number are characterised and/or commercially available compared to nicking endonucleases, can thus be readily employed as nicking agents for use in the method. Therefore a much wider range of enzymes can be considered during assay development, which assists the targeting of particular target sequences and selection of enzymes with appropriate properties (e.g. rate, temperature optimum) for a particular purpose.

3.11. Oligonucleotide Probe Cleavage by Five Distinct Nicking Endonucleases

Figure 13A:
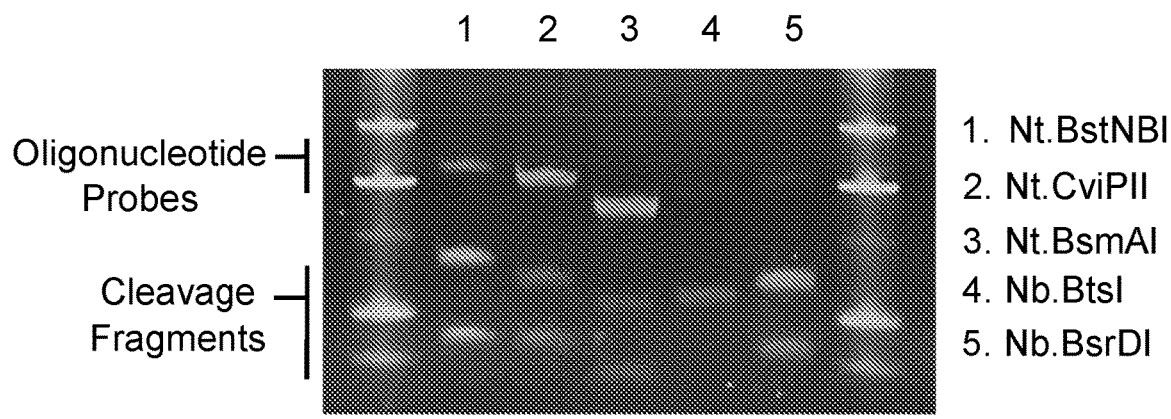
FIG. 13A. Oligonucleotide probe cleavage by five distinct nicking endonucleases (see Example 3.11).

In order to investigate the suitability of various nicking agents for the performance of the method, we carried out oligonucleotide probe cleavages with a panel of five commercially available nicking endonucleases. Digestion reactions were assembled for each enzyme with an associated oligonucleotide probe containing the relevant recognition site and following the manufacturers recommended reaction conditions. Reactions for each enzyme were assembled with a total of 100 ng of the M13mp18 template or in the case of the Nb.BtsI reaction, 0.5 pmol of oligonucleotide probe, SEQ9. Reaction components were added as follows; Nt.BstNBI digestion—5 pmol of oligonucleotide probe SEQ10, 5 U Nt.BstNBI (NEB), 1 µl of 10×NEB buffer 3.1 (NEB), 1 µl of M13mp18 and dH$_2$O to a final reaction volume of 10 µl. The reaction was incubated at 55° C. for one hour. Nt.CviPII digestion-5 pmol of oligonucleotide probe SEQ11, 5 U Nt.CviPII (NEB), 1 µl of 10×NEB buffer 3.1 (NEB), 1 µl of M13mp18 and dH$_2$O to a final reaction volume of 10 µl. The reaction was incubated at 45° C. for one hour. Nt.BsmAI digestion—5 pmol of oligonucleotide probe SEQ12, 5 U Nt.BsmAI (NEB), 1 µl of 10×NEB buffer 3.1 (NEB), 1 µl of M13mp18 and dH$_2$O to a final reaction volume of 10 µl. The reaction was incubated at 55° C. for one hour. Nb.BtsI digestion—5 pmol of oligonucleotide probe SEQ13, 5 U Nb.BtsI (NEB), 1 µl of 10×NEB buffer 3.1 (NEB), 1 µl of SEQ9 and dH$_2$O to a final reaction volume of 10 µl. The reaction was incubated at 55° C. for one hour. Nb.BsrDI digestion—5 pmol of oligonucleotide probe SEQ14, 5 U Nb.BsrDI (NEB), 1 µl of 10×NEB buffer 3.1 (NEB), 1 µl of M13mp18 and dH$_2$O to a final reaction volume of 10 µl. The reaction was incubated at 55° C. for one hour. The digestion products of each reaction were analysed by TBE-Urea polyacrylamide gel electrophoresis (PAGE) using a 15% w/v gel stained with SYBR Gold (Life Technologies) and visualised using a transilluminator, (FIG. 13A). Each nicking endonuclease demonstrated efficient M13mp18 mediated probe cleavage and target recycling in all cases, as evidenced by the presence of bands corresponding to the expected size of cleavage products in each lane of the gel. This example demonstrates the potential to use a number of nicking endonucleases in the method.

3.12. Low Temperature Oligonucleotide Probe Cleavage

Figure 13B:
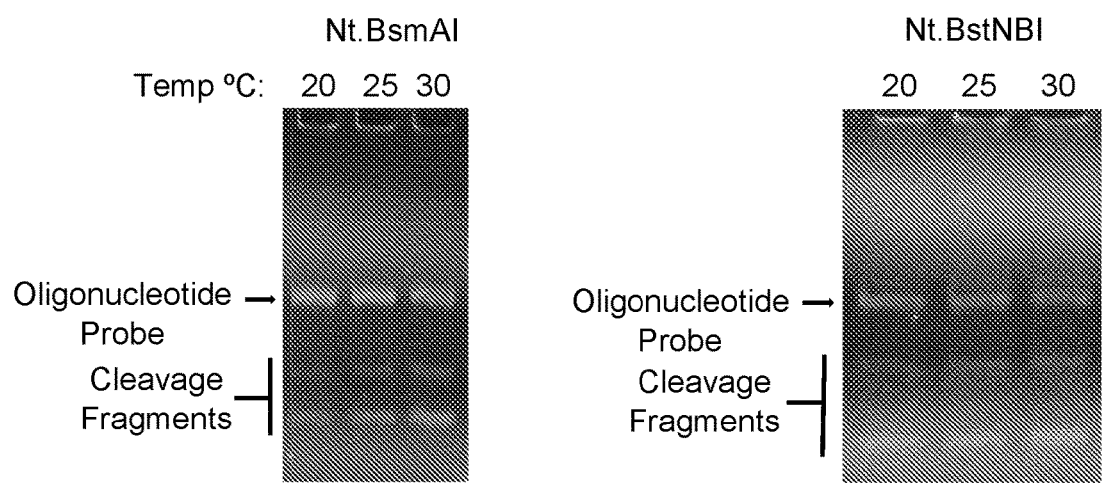
FIG. 13B. Low temperature oligonucleotide probe cleavage (see Example 3.12).

Temperature is thought to have an influence on the rate of the oligonucleotide probe cleavage reactions, due to the thermal optima of the nicking agents used and the respective melting temperature of the probe and the cleavage products. The majority of commercially available nicking endonucleases are recommended to have heated reactions. To determine the ability of certain enzymes to exhibit activity at low temperature, we performed oligonucleotide probe cleavage reactions at low temperatures. Reactions were prepared containing 5 pmol oligonucleotide probe (SEQ2 for Nt.BstNBI or SEQ15 for Nt.BsmAI), 5 U Nt.BstNBI or Nt.BsmAI, 0.5 pmol oligonucleotide target nucleic acid and dH$_2$O to a final volume of 10 µl. Reactions were incubated at 20° C., 25° C. or 30° C. for 1 hour and the entirety of each reaction was analysed by TBE-Urea PAGE (15% w/v gel), FIG. 13B. Surprisingly, efficient probe cleavage was demonstrated using both nicking endonucleases at 20° C. (lane 1), 25° C. (lane 2) and 30° C. (lane 3). Furthermore, there is evidence of target recycling at low temperatures. This example demonstrates that it would be possible to perform the present invention without heating the probe cleavage reactions. It is anticipated that the exponential signal amplification effect of the method will off-set the reduction in rate resulting from performing probe cleavage reactions below their optimum temperature.

3.13. Detection of Two or More Target Nucleic Acids in the Same Sample

The method of the invention may be readily used to differentially detect two of more target nucleic acids in the same sample. In this example we have performed simultaneous detection of two different viral DNA target nucleic acids. For viral target 1 the oligonucleotide probes P1-a and P2-a were the same as employed in Example 3.2. For viral target 2 the oligonucleotide probes P1-b and P2-b were the same as those employed in Example 2.1. In both cases a single double strand cleaving agent (a class II restriction endonuclease) was employed as the first nicking agent. The same double strand cleaving agent was also used as the second nicking agent for viral target 2 (second nicking agent B), although a different nicking agent, AlwI, was used as the second nicking agent for viral target 1 (second nicking agent A). By employing different P2 probes with different nicking agents the probes were designed to maximise the chance of the two reactions functioning at the same time without any unintended cross-talk.

Reactions for step a) were prepared containing: 0.5 pmol probe P1-a; 0.1 pmol probe P1-b; 1 U first nicking agent; 5 µM dNTP; 1 U of Bst 3.0 polymerase (NEB) and 5 fmol of viral target 1 or viral target 2 in a final volume of 10 µl containing 1× Isothermal Buffer II (NEB). Reactions were incubated at 37° C. for 30 min before inactivation of the polymerase by heating at 95° C. for 10 min. Reactions for step b) were prepared containing 2 µl of the reactions from step a) and either 5 pmol probe P2-a and 2.5 U second nicking agent A or 5 pmol probe P2-b and 2.5 U of second nicking agent B, in each case in a 10 µl total volume containing 1× CutSmart buffer (NEB). Following incubation at 37° C. for 30 min the entire reactions were analysed by TBE-Urea polyacrylamide gel electrophoresis (PAGE) using a 15% w/v gel stained with SYBR Gold (Life Technologies) and visualised using a UV transilluminator.

Figure 14A:
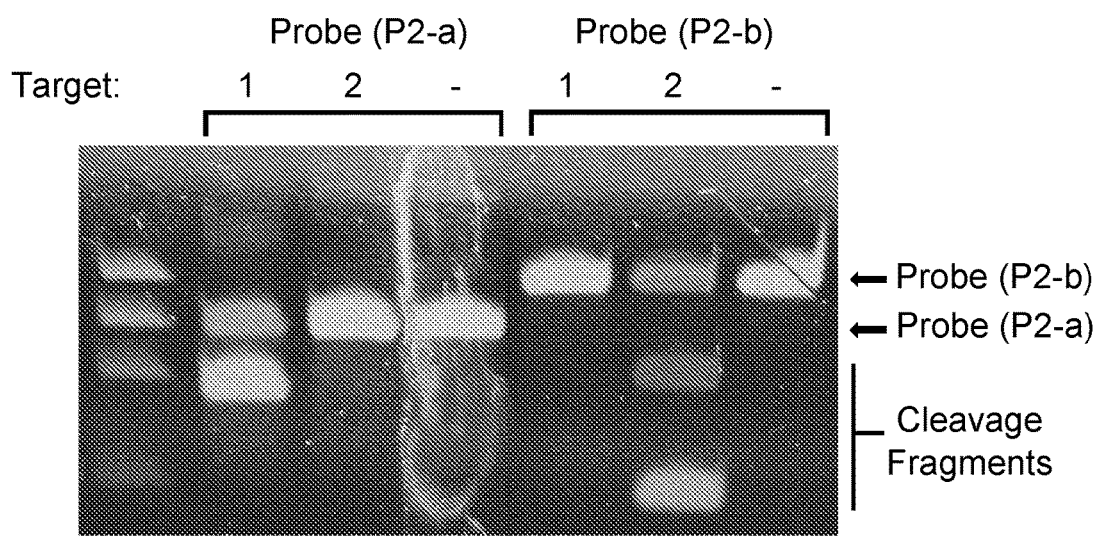
FIG. 14A, FIG. 14B, FIG. 14C and FIG. 14D. Detection of two or more target nucleic acids in the same sample (see Example 3.13).

FIG. 14A displays a photograph of the stained polyacrylamide gel electrophoresis gel obtained, indicating the relevant P2 probe and target added to step a) of the reaction. As expected, bands corresponding to cleavage fragments were only observed in the presence of the relevant viral target. Therefore presence of the P1 variant for the other viral target in step a) of the reaction did not lead to any detrimental effect on the performance of the method, demonstrating the potential for step a) of the method to be readily multiplexed, for the simultaneous detection of multiple target nucleic acids in the same sample.

Figure 14B:
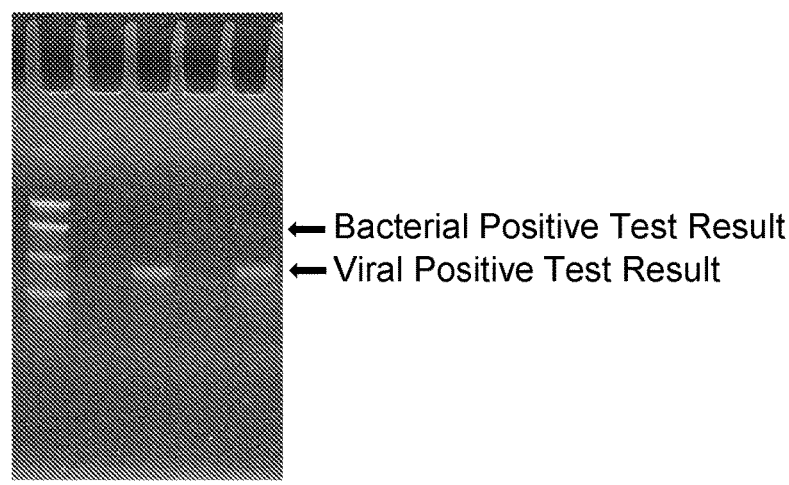
Figure 14C:
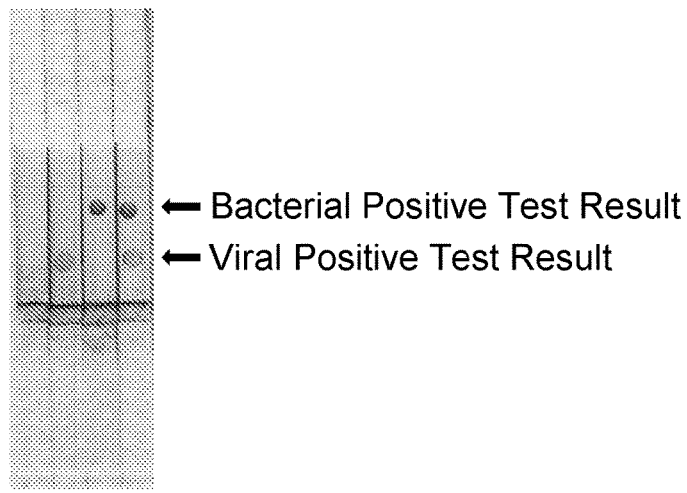

In order to also demonstrate the potential for step b) of the reaction to be performed in a multiplex format for simultaneous detection of multiple target nucleic acids, we next performed simultaneous detection of a bacterial and a viral target in the same sample using an oligonucleotide probe cleavage reaction. For each of the bacterial and the viral target an oligonucleotide probe was designed with complementarity to a particular site within the target sequence and containing the recognition sequence and cleavage site for a nicking agent. The bacterial and viral target are surrogates of the fragment F1 that would be produced in step a) of the method. A different double-strand cleaving restriction endonuclease was employed for each of the targets. The oligonucleotide probes were each conjugated to beads following standard protocols. Reactions were performed containing approximately 50 µg of beads for each oligonucleotide probe, 1 µl of 10× Isothermal reaction buffer (NEB), 5 U of each enzyme, 0.25 pmol of each target nucleic acid sequence (either the bacterial target, the viral target or both together) and dH$_2$O to a final volume of 10 µl. Reactions were incubated at 50° C. for 1 hour and the entire reaction was subsequently analysed by TBE-Urea PAGE (15% w/v gel) (FIG. 14B). Reactions were also analysed by carbon nucleic acid lateral flow (FIG. 14C) wherein the strips were printed with two oligonucleotides in discrete locations, one complementary to the probe fragment that would be produced from the viral target beads and the other complementary to the probe fragment that would be produced from the bacterial target beads. 60 µl of running buffer was added to each reaction and the entire volume was applied to the sample pad of a lateral flow strip, which were photographed following signal development.

The first reaction contained neither template and consequently no signal was observed on the gel or on the lateral flow strip. The second reaction contained the viral target only and produced only the probe fragment from the beads conjugated with the oligonucleotide complementary to the viral target. The third reaction contained the bacterial target only and produced only the probe fragment from the beads conjugated with the oligonucleotide complementary to the bacterial target. The fourth reaction contained both viral and bacterial targets and thus both probe fragments were detected.

This example demonstrates that multiple targets can be detected simultaneously in step b) of the method enabling multiple different combinations of probes (P1) and (P2) to be employed for detection of different target nucleic acids in the same sample. Furthermore, the carbon nucleic acid lateral flow assay provides a powerful opportunity for rapid multiplex detection of different targets by colour signal change, by virtue of differential hybridisation of the single-stranded probe fragments produced in the method to their complementary oligonucleotide immobilised on the lateral flow strip.

Figure 14D:
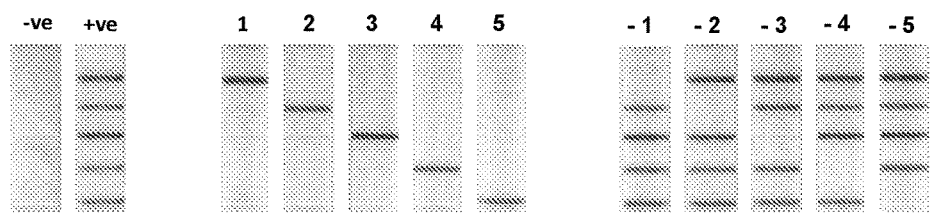

In order to further demonstrate the capability of the method for detection of multiple targets by colorimetric lateral flow assay we have developed a 5-plex assay, comprising five probe fragments of different sequence with their reverse complementary sequence immobilised on a lateral flow strip. The lateral flow strip was prepared as described in the general methods section. Each of the complementary oligonucleotides was printed at a defined location on lateral flow strips and immobilised by UV crosslinking. 0.1 pmol of each of ten probe fragments attached to a biotin moiety were added 60 µl of running buffer and applied to the sample pad. A control strip was prepared in which each of these probe fragments was sequentially added, or omitted. Results were recorded by photography following signal development and are displayed in FIG. 14D. All five probe fragments were detected by clear colour signal change at the expected location, demonstrating the integrity of the hybridisation based signal location. This experiment clearly demonstrates the powerful multiplexing capability of the method of the invention for use in a low-cost, rapid, colorimetric nucleic acid lateral flow assay format. In certain applications of the method it is frequently required to detect multiple targets in the same sample, for example, when there are multiple potential causes of a disease, or in order to derive genetic sequence information regarding a number of different sites within the genome of an organism. The method of the invention is particularly amenable to multiplex detection due to the generation of single-stranded probe fragments which can be separated from the other reaction components via a lateral flow membrane and differentially detected at particular locations via hybridisation based localisation.

Example 4

Exponential Amplification in Step a) in a Single-Pot Reaction

In this example we performed an embodiment of the method with cross-priming in step a) in a single-pot reaction, whereby step a) and step b) are performed simultaneously. We also performed detection in step c) by both gel electrophoresis and nucleic acid lateral flow (colorimetric) detection.

A viral nucleic acid target was detected using the same variant of P1 that was employed in Example 2.3. For detection by gel electrophoresis, the same P2 variant was used as in Example 2.3 (P2-a). For detection by nucleic acid lateral flow the P2 variant used in Example 1 was used (P2-b). A single double strand cleaving agent (a class II restriction endonuclease) was employed as both the first and second nicking agent.

Figure 15A:
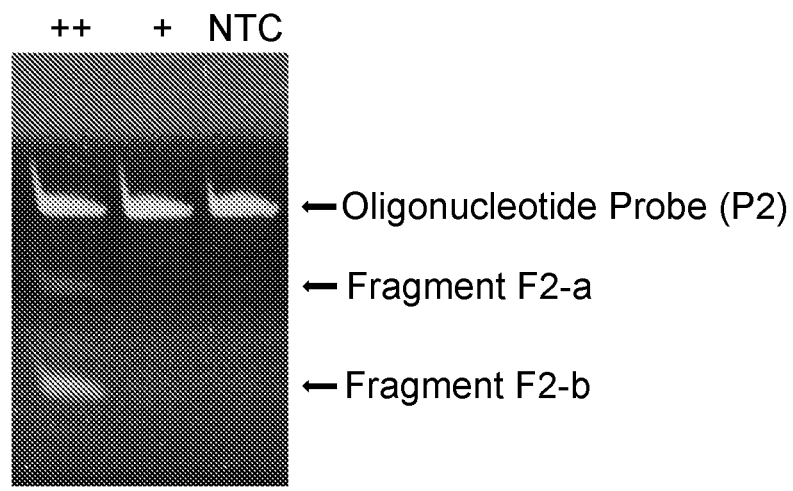
FIG. 15A. Exponential amplification in step a) in a single-pot reaction with gel electrophoresis detection in step c) (see Example 4).

For detection in step c) by gel electrophoresis, reactions for step a) and b) were prepared containing: 0.05 pmol probe P1; 5 pmol probe P2-a, 1 U nicking agent; 100 µM dNTP; 1 U of Bst 3.0 polymerase (NEB) and various amounts of viral target nucleic acid in a final volume of 10 µl containing 1× Isothermal Buffer II (NEB). Following incubation at 37° C. for 30 min, the entire reactions were analysed by TBE-Urea polyacrylamide gel electrophoresis (PAGE) using a 15% w/v gel stained with SYBR Gold (Life Technologies) and visualised using a UV transilluminator. A photograph of the resulting gel is displayed in FIG. 15A. The cleavage fragments F1 were clearly visible in presence of target nucleic acid at the lowest level detected (++=1 fmol; +=10 amol; NTC=No Target Control), demonstrating that steps a) and b) of the method can be readily combined for simple and rapid sensitive detection, with exponential amplification in step a).

Figure 15B:
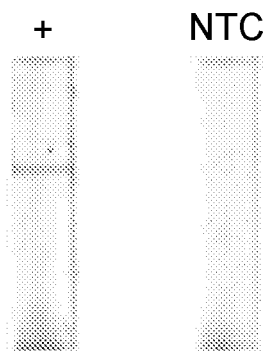
FIG. 15B. Exponential amplification in step b) in a single-pot reaction with oligonucleotide probe (P2) attached to a solid material and nucleic acid lateral flow colorimetric detection with carbon nanoparticles in step c) (see Example 4).

Lateral flow strips were prepared following the protocol described in the general methods section, printed with an oligonucleotide probe of a sequence complementary to the probe fragment that would be produced following cleavage of P2-b probe. The oligonucleotide probes were conjugated to beads using standard methods. For detection in step c) by nucleic acid lateral flow, reactions for step a) and b) were prepared containing: 0.05 pmol probe P1; 3.5 µg of beads attached to P2-b; 1 U nicking agent; 10 µM dNTP; 1 U of Bst 3.0 polymerase (NEB) and 1 fmol viral target nucleic acid in a final volume of 10 µl containing 1× Isothermal Buffer II (NEB). Following incubation of the reactions at 37° C. for 40 min, 50 µl running buffer was added and the entire contents of each reaction was applied to the sample pad of a lateral flow strip. Following signal development, the lateral flow strips were photographed (FIG. 15B). Colorimetric signal, in the form of a black line of carbon deposit corresponding to the location of the complementary printed oligo, was clearly visible in a target dependent manner. This example demonstrates a very simple embodiment of the invention in which the detection of target nucleic acid is performed in a single reaction before being deposited directly on a lateral flow strip to determine the result. This example demonstrates the potential of the invention to be applied in the sensitive, rapid detection of target nucleic acids in a colorimetric assay with low temperature incubation and is therefore highly attractive for application to low-cost, diagnostic devices.

Example 5

Exponential Amplification Using Cycling Process with Probe (P1) and Target Primer in Step a)

In this example we performed various embodiments of the invention wherein the double-stranded nucleic acid amplifier which is cleaved in step a) (A), contains two or more nicking agent cleavage sites, one or more cleavage site in the target derived strand and one or more cleavage site in the probe (P1) derived strand, wherein a target nucleic acid primer is used that contains the recognition sequence for the first nicking agent and probe (P1) contains the recognition sequence for a probe (P1) nicking agent. In such embodiments a cycling process occurs as illustrated in FIG. 2E with potential for additional amplification in step a). Firstly, in Example 5.1, a variety of combinations of probe (P1), target primer and nicking agents were employed. The potential of the method for sensitive detection of pathogen was then demonstrated in Example 5.2 with the production of the double-stranded nucleic acid amplifier as illustrated in FIG. 2D, firstly using cDNA and then in an integrated reaction for direct detection of single-stranded RNA. Detection in step c)

was performed by both gel electrophoresis and nucleic acid lateral flow, demonstrating the amenability of the method of the invention for exploitation in a low-cost device for rapid and sensitive detection of pathogens.

5.1. Various Nicking Agents

In order to demonstrate the performance of embodiments of the method with the cycling process illustrated in FIG. 2E, various assays were designed and tested in this example utilising different probes, primers and nicking agents. Two alternative enzymes were employed as the first nicking agent or probe (P1) nicking agent: Eco31I, an asymmetric double-strand cleaving restriction endonuclease with recognition sequence 5'GGTCTC3' (1/5) and BsoBI, a degenerate palindrome double-strand cleaving restriction endonuclease with recognition sequence 5'CYCGRG3' (−5/−1). Two alternative enzymes were employed as the second nicking agent: Nt.AlwI, a nicking endonuclease with recognition sequence 5'GGATC3' (4/-) and Eco31I.

Firstly, Eco31I was used as the first nicking agent and probe (P1) nicking agent with BsoBI as the second nicking agent. The production of the double stranded nucleic acid amplifier was performed as illustrated in FIG. 2B, wherein the 'target nucleic acid' in the method is produced by extension of the target nucleic acid primer (SEQ16), using SEQ18 as a template. Since SEQ18 is single-stranded DNA separation of the target nucleic acid from SEQ18 is performed by disassociation or strand displacement. The target primer (SEQ16) and the probe (P1) primer (SEQ17) were designed following similar design parameters with a 15 base 3' complementarity region for hybridisation to SEQ18, in the case of the target primer, or for hybridisation to the target nucleic acid sequence, in the case of Probe (P1). SEQ16 and SEQ17 were designed such that their 3' hydroxyl terminus was positioned either side of the recognition sequence for the second nicking agent BsoBI present within SEQ18. SEQ16 and SEQ17 each contained the Eco31I restriction recognition sequence upstream and a 5' region comprising 11 bases to form the stable primers following cleavage at the nicking agent cleavage sites of the double stranded nucleic acid amplifiers. Probe (P2), SEQ19, was designed to contain the top strand cleavage site of the BsoBI site present within SEQ18 (5'CCCGAG3'), with further 9 bases of sequence complementarity upstream and 2 bases downstream in order to achieve efficient hybridisation and target recycling of fragment (F1) produced. In this example, probe (P1) and the target primer were designed such that alpha thiol modified nucleotide dTTP would be inserted by the polymerase in order to block the cleavage of the reverse complementary strand and thus ensure the double-strand cleaving enzyme Eco31I would function as a nicking agent in step a) of the method. Furthermore, the recognition sequence for the second nicking agent within SEQ18 was selected such that the thiol modified dTTP would be inserted into fragment (F1) to produce the following variant of the recognition sequence 5'C*TCGGG3' and thus ensure the double-strand cleaving agent BsoBI would function as a nicking agent in step b) of the method.

Figure 16:
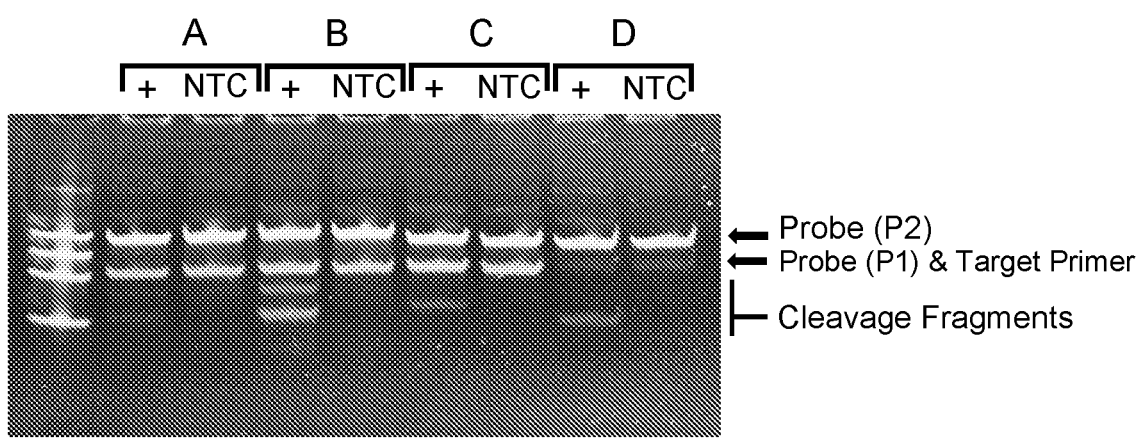
FIG. 16. Exponential amplification using cycling process in step a)—various nicking agents (see Example 5.1).

Reactions for step a) were carried out in a 10 μl volume containing 0.8 pmol target primer SEQ16, 0.4 pmol probe (P1) SEQ17, 10 μM dATP, dGTP and dCTP (Life Technologies), 50 μM Thymidine-5'-O-1-Thiotriphosphate (Sp-TTP-α-S) (Biolog Life Science Institute), 2 U of Bacillus polymerase and 0.5 μl FastDigest Eco31I (Life Technologies) in 0.5× Isothermal Amplification buffer (NEB) and 0.5× FastDigest buffer (Life Technologies). +/−10 fmol SEQ18 was added as target. Firstly, SEQ16, SEQ17, dNTP (including Sp-TTP-α-S) and target SEQ18 were prepared in 8 μl 0.5× Isothermal buffer (NEB) and 0.5× FastDigest buffer (Life Technologies) and incubated for 1 min at 95° C. followed by 1 min at the reaction temperature. Enzymes were added in 2 μl of 0.5× Isothermal buffer (NEB) and 0.5× FastDigest buffer (Life Technologies) to trigger the start of the reaction. Reactions were incubated at either 37° C. or 45° C. for 15 min before inactivation of the enzymes by incubation at 95° C. for 5 min. After heat inactivation, 5 μl of the resulting reaction mix was transferred to a 10 μl step b) reaction containing 5 pmol probe P2 (SEQ19) and 2.5 U BsoBI (NEB) in 0.5× CutSmart buffer (NEB), 0.25× Isothermal Amplification buffer (NEB) and 0.25× FastDigest buffer (Life). Step b) reactions were incubated for 20 min at either 37° C. or 45° C. and the entire reactions were then analysed by TBE-Urea polyacrylamide gel electrophoresis (PAGE) using 15% w/v gel stained with SYBR Gold (Life Technologies) and visualised using a UV Transilluminator. The results obtained using a reaction temperature of 37° C. (A) and 45° C. (B) are displayed in FIG. 16.

Secondly, an equivalent assay was designed using Eco31I as the first nicking agent and probe (P1) nicking agent and Nt.AlwI as the second nicking agent. The target nucleic acid primer (SEQ20) and probe (P1) (SEQ21) were designed such that their 3' hydroxyl terminus is positioned either side of the cleavage site of Nt.AlwI within SEQ22. The complementarity region of the target primer is designed to hybridise to SEQ22 and be extended to produce the target nucleic acid for the method. Following separation of SEQ22 from the target nucleic acid and, the complementarity region of SEQ21 then hybridises to the target derived strand and is extended. The process continues as illustrated in FIG. 2B, with a further cycling process as illustrated in FIG. 2E. Alpha thiol dTTP was again used to ensure the double-strand cleaving agent, Eco31I functioned as a nicking agent that is only able to cleave the sites present within probe (P1) and the target primer and not able to cleave the bottom strand site located in the reverse complement of probe (P1) and the target primer.

Reactions for step a) were carried out in a 10 μl volume containing 0.8 pmol target primer SEQ20, 0.4 pmol probe (P1) SEQ21, 10 μM dATP, dGTP and dCTP (Life Technologies), 50 μM Thymidine-5'-O-1-Thiotriphosphate (Sp-TTP-α-S) (Biolog Life Science Institute), 2 U of Bacillus polymerase and 0.2 μl FastDigest Eco31I (Life Technologies) in 0.5× Isothermal Amplification buffer (NEB) and 0.5× FastDigest buffer (Life Technologies). +/−10 fmol SEQ22 was added as target. Firstly, SEQ20, SEQ21, dNTP (including Sp-TTP-α-S) and target SEQ22 were prepared in 8 μl 0.5× Isothermal buffer (NEB) and 0.5× FastDigest buffer (Life Technologies) and incubated for 1 min at 95° C. followed by 1 min at the reaction temperature. Enzymes were added in 2 μl of 0.5× Isothermal buffer (NEB) and 0.5× FastDigest buffer (Life Technologies) to trigger the start of the reaction. Reactions were incubated at 50° C. for 15 min before inactivation of the enzymes by incubation at 95° C. for 5 min. After heat inactivation, 5 μl of the resulting reaction mix was transferred to a 10 μl step b) reaction containing 5 pmol probe P2 (SEQ23) and 2.5 U Nt.AlwI (NEB) in 0.5× CutSmart buffer (NEB), 0.25× Isothermal Amplification buffer (NEB) and 0.25× FastDigest buffer (Life). Step b) reactions were incubated for 20 min at 55° C. and the entire reactions were then analysed by TBE-Urea polyacrylamide gel electrophoresis (PAGE) using 15% w/v gel stained with SYBR Gold (Life Technologies) and visualised using a UV Transilluminator. The results obtained are displayed in FIG. 16(C).

A third assay was designed using BsoBI as the first nicking agent and probe (P1) nicking agent and Eco31I as the second nicking agent. The target nucleic acid primer (SEQ24) and probe (P1) (SEQ25) were designed such that their 3' hydroxyl terminus is positioned at either end of the recognition sequence for Eco31I within SEQ26. Alpha thiol dTTP was again used to ensure the double-strand cleaving agent, BsoBI functioned as a nicking agent that is only able to cleave the sites present within probe (P1) and the target primer and is not able to cleave the bottom strand site located in the reverse complement of probe (P1) and the target primer.

Reactions for step a) were carried out in a 10 µl volume containing 100 fmol target primer SEQ24, 50 fmol probe (P1) SEQ25, 10 µM dATP, dGTP and dCTP (Life Technologies), 50 µM Thymidine-5'-O-1-Thiotriphosphate (Sp-TTP-α-S) (Biolog Life Science Institute), 2 U of *Bacillus* polymerase and 2 U BsoBI (NEB) in 1× Isothermal Amplification buffer (NEB). +/−10 fmol SEQ26 was added as target. Firstly, SEQ24, SEQ25, dNTP (including Sp-TTP-α-S) and target SEQ26 were prepared in 8 µl 1× Isothermal buffer (NEB) and incubated for 1 min at 95° C. followed by 1 min at the reaction temperature. Enzymes were added in 2 µl of 1× Isothermal buffer (NEB) to trigger the start of the reaction. Reactions were incubated at 50° C. for 25 min before inactivation of the enzymes by incubation at 95° C. for 5 min. After heat inactivation, 5 µl of the resulting reaction mix was transferred to a 10 µl step b) reaction containing 5 pmol probe P2 (SEQ27) and 0.5 µl FastDigest Eco31I (Life) in 0.5× FastDigest buffer (NEB) and 0.5× Isothermal Amplification buffer (NEB). Step b) reactions were incubated for 40 min at 45° C. and the entire reactions were then analysed by TBE-Urea polyacrylamide gel electrophoresis (PAGE) using 15% w/v gel stained with SYBR Gold (Life Technologies) and visualised using a UV Transilluminator. The results obtained are displayed in FIG. 16(D).

In each of the assays described in this example, the results obtained (FIG. 16) display a clear band corresponding to the probe fragment (F2) visible in the +lane and no equivalent band visible in the no target control (NTC) lane, demonstrating the correct functioning of the method. This example demonstrates that it is possible to readily develop variants of the method with the cycling amplification process illustrated in FIG. 2E using a variety of different probe/primers, nicking agents and reaction conditions (e.g. temperature). In addition to the data displayed, a wide range of other assays have been developed for different targets exploiting different nicking agents, probe/primer designs and alternative alpha thiol modified nucleotides. Through optimisation, such assays have been developed that are capable of detecting less than ten (10) copies of a target nucleic acid. Integrated assays have also been performed wherein step a) and step b) are performed simultaneously. This example demonstrates that embodiments of the method comprising additional amplification resulting from the cycling process illustrated in FIG. 2E and with the additional specificity derived from having two primer/probe hybridisation events in addition to the restriction enzyme cleavage in step b) can be readily developed for any given target.

5.2 Sensitive Detection of Viral Pathogen Target

Embodiments of the method with the cycling process illustrated in FIG. 2E have been used to perform highly sensitive and specific assays for the detection of viruses, with potential for application in the diagnosis of disease. In this example 5.2, assays were designed and developed for a target sequence within a viral mRNA. Given that the reverse complement of the second nicking agent cleavage site that forms the basis of step b) of the assay is contained in the mRNA sequence then the method in this example is performed according to FIG. 2D, such that fragment (F1) is displaced from the target derived strand. However, in the design of an assay for an endogenous target using the cycling process, since probe (P1) and the target primer are designed using the same parameters and both are required for the method, whether the method proceeds according to FIG. 2B or FIG. 2D is determined solely by which strand contains the reverse complement to the second nicking agent recognition sequence. In this example 5.2, the method was performed wherein the reverse transcription step in which probe (P1) is extended using the target nucleic acid as a template is performed separately and wherein it is performed alongside the other parts of step a) of the method in a single integrated reaction. In the latter integrated reaction, the same assay (reagents, conditions etc.) would be used to detection the genomic RNA strand according the method illustrated in FIG. 2B as the mRNA transcript according to the method illustrated in FIG. 2D in the event the second nicking agent cleavage site selected was present in the other strand.

The target nucleic acid used in this example 5.2 was a 1,050 base single-stranded RNA molecule, being a genomic segment of an RNA virus of clinical relevance. Oligonucleotide probe (P1) was designed containing, in the 5' to 3' direction, 29 bases of single-stranded DNA with the following sequence components: (i) an 8-base stabilising region that forms part of the primer following cleavage by the probe (P1) nicking agent; (ii) the 5 base recognition sequence of the probe (P1) nicking agent, being a class II double-strand cleaving restriction endonuclease; and (iii) a 16 base complementarity region capable of sequence specific hybridisation to the RNA target between positions 737-752. Following hybridisation of P1 to the target nucleic acid and extension of the probe, a complementary DNA transcript (cDNA) of approximately 765 bases (752+13 bp) is produced, assuming transcription to the end of the RNA template. Reverse transcription reactions were performed in 20 µl containing 5µM oligonucleotide probe (P1), 125µM dCTP, 125µM dGTP, 125 µM dTTP, 500 µM 2'-Deoxythymidine-5'-O-(1-Thiotriphosphate), viral mRNA (various levels), 200 U M-MuLV reverse transcriptase (NEB) and 8 U Murine RNase Inhibitor (NEB) in 1×M-MULV buffer (NEB). The reaction was incubated at 42° C. for 60 min, before inactivation of the reverse transcriptase by incubation at 65° C. for 20 min. During the reverse transcription reaction, probe (P1) hybridises to the target nucleic acid and is extended to produce the 765 base cDNA containing phosphorothioate linkages before each thymine base.

A target nucleic acid primer was designed containing, in the 5' to 3' direction, 29 bases of single-stranded DNA with the following: (i) an 8-base stabilising region that forms part of the primer following cleavage by the probe (P1) nicking agent; (ii) the 5 base recognition sequence for the first nicking agent, which is the same class II double-strand cleaving restriction endonuclease as the probe (P1) nicking agent; and (iii) a 14 base complementarity region capable of sequence specific hybridisation to the complementary DNA transcript created by probe (P1) at position 32-45 bases from its 5' end. The 3' termini of the probe (P1) and target nucleic acid primer are positioned on opposite strands of the target nucleic acid with a two base gap around a cleavage site for the second nicking agent naturally present within the mRNA sequence. The reverse complement of the second nicking agent cleavage site is within the target derived strand such that it is displaced as fragment (F1).

Figure 17A:
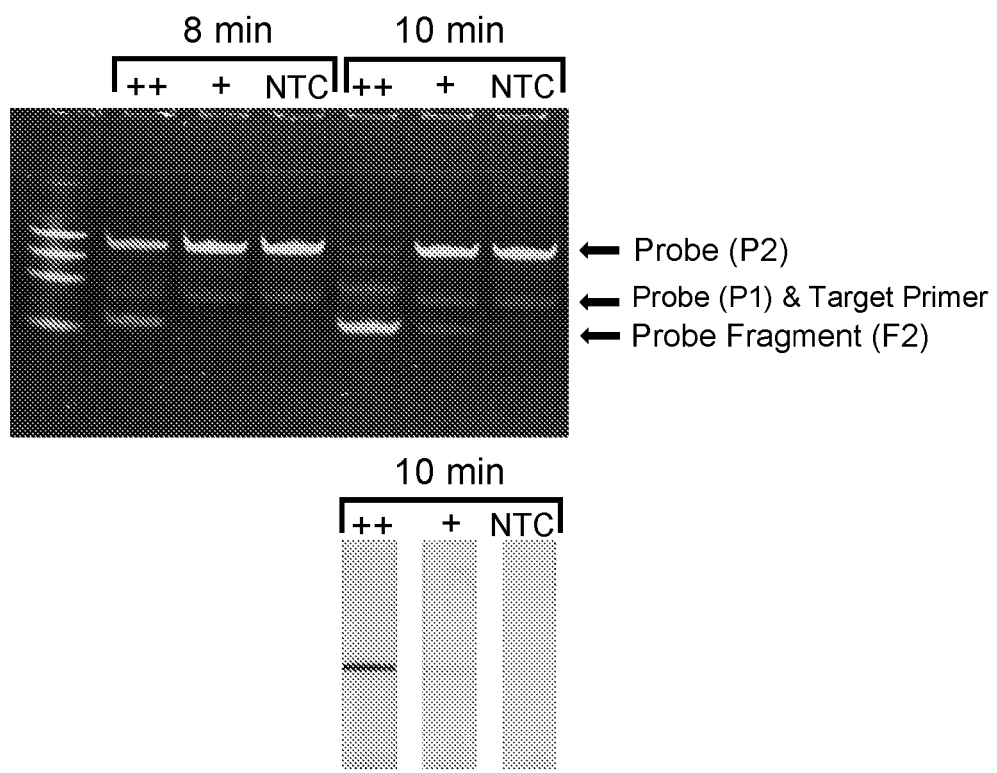
FIG. 17A. Exponential amplification using cycling process in step a)—sensitive detection of viral pathogen target (see Example 5.2).

The step a) amplification reaction was prepared in a 10 μl volume containing 100 fmol probe (P1), 400 fmol of target primer, 50 μM 2'-Deoxythymidine-5'-O-(1-Thiotriphosphate), 10 μM dATP, 10 μM dCTP, 10 μM dGTP, 25 mM Tetramethylammonium chloride (Sigma-Aldrich), 2 U *Bacillus* polymerase; 0.5 U of the first nicking agent/probe (P1) nicking agent and various levels of cDNA (diluted in nuclease free water) in 1× Isothermal Amplification buffer (NEB). Reactions were incubated at 55° C. for 8 min or 10 min, before incubation at 95° C. for 5 min to inactivate the enzymes. In step b) 5 μl of the step a) amplification reaction was added to a cleavage reaction in a 10 μl total volume with 5 pmol probe (P2) and 2.5 U of the second nicking agent in 0.5× Isothermal Buffer and 0.5× Buffer 3.1 (NEB). Reactions incubated at 55° C. for 20 min before the entire reactions were analysed by TBE-Urea polyacrylamide gel electrophoresis (PAGE) using 15% w/v gel stained with SYBR Gold (Life Technologies) and visualised using a UV Transilluminator. Alternatively detection in step c) was performed by nucleic acid lateral flow wherein 5 μl of the reaction from step a) (10 min) was added to a cleavage reaction in 10 μl total volume containing 4 μg beads attached to probe (P2) and 2.5 U of the second nicking agent in 0.5× Isothermal Amplification buffer (NEB) and 0.5× Buffer 3.1 (NEB). Reactions were incubated for 15 min at 55° C. before addition of 55 μl lateral flow running buffer and deposition of the entire mix onto a carbon nucleic acid lateral flow strip prepared following standard protocols. The results produced in this example using a target level of 100 zmol (++) and lzmol (+) are displayed in FIG. 17A. Cleavage bands corresponding to fragment (F2) were clearly visible on the gel in the presence of target nucleic acid and not in the no target control (NTC), indicating the sensitive and specific detection of as few as 600 copies of the viral target. The lateral flow strips displayed deposition of the colorimetric carbon signal only in the presence of target.

Probe (P2) was designed to contain in the 5' to 3' direction, a 43 base sequence comprising the following: (i) an 8 base spacer; (ii) a 17 base region that is reverse complementary to the region of fragment (F1) and containing the five base recognition sequence and cleavage site for the second nicking agent, a nicking restriction endonuclease; and (iii) an 18 base spacer designed to facilitate detection of the 3' portion of the probe as fragment (F2) in step c) of the method. Cleavage of probe (P2) by the second nicking agent leads to it being cleaved into a 20 base 5' fragment and a 23 base 3' fragment the latter of which is detected at fragment (F2).

The double stranded nucleic acid amplifier in this example is produced as described below. Firstly P1 hybridises to the relevant region of the single-stranded RNA target nucleic acid:

```
P1:
5' SSSSSSSSXXXXXDDDDDDDDDDDDDDDDD 3'

Target (ssRNA):
3'...dddddddddddddddddddddddddddddddddddddd
d...5'
```

Following extension of P1 and removal of the target nucleic acid by the action of RNase H the 765 base cDNA forms contains a site for hybridisation of the target nucleic acid primer.

```
P1:
5'SSSSSSSSXXXXXDDDDDDDDDDDDDDDDDDDDDDDDDDDDDD
DDDDDDDDDDD...3'

Target Primer:
3'ddddddddddddddddXXXXXSSSSSSSS-5'
```

The target primer is extended to form the cleavage site for the probe (P1) nicking agent (indicated by /) due to the insertion of alpha thiol nucleotide at the bottom strand cleavage position (indicated by *).

```
P1:
5'SSSSSSSSXXXXXD/DDDD_DDDDDDDDDDDDDDDDDDDDDDDDD
DDDDDDDDDDDD...3'

T:
3'ssssssssxxxxxd_dddd*ddddddddddddddddddddddddddd
XXXXXSSSSSSSS-5'
```

Following cleavage by the probe (P1) nicking agent and extension of the primer comprising the sequence 5'-SSSSSSSSXXXXXD-3', the double stranded-nucleic acid amplifier is produced containing a cleavage site for the first nicking agent within the target derived strand:

```
P1:
5'SSSSSSSSXXXXXD/DDDD_DDDDDDDDDDDDDDDDDDDDDD*
DDDD_Dxxxxxssssssss-3'

T:
3'ssssssssxxxxxd_dddd*ddddddddddddddddddddddd_
dddd/dXXXXXSSSSSSSS-5'
```

Following production of the double-stranded nucleic acid amplifier, the cycling amplification process illustrated in FIG. 2E occurs. The first fragment (F1) comprises the sequence
3'-ssssssssxxxxxd_dddd*ddddddddddddddddddddddd_
dddd-5' and the second fragment (F1) produced comprises the sequence 3'-dddd*ddddddddddddddddddddddd_dddd-5'. Both fragments contain a 17 base region of reverse complementary sequence to probe (P2), which following hybridisation, form the recognition sequence and cleavage site for the second nicking agent within probe (P2).

Figure 17B:
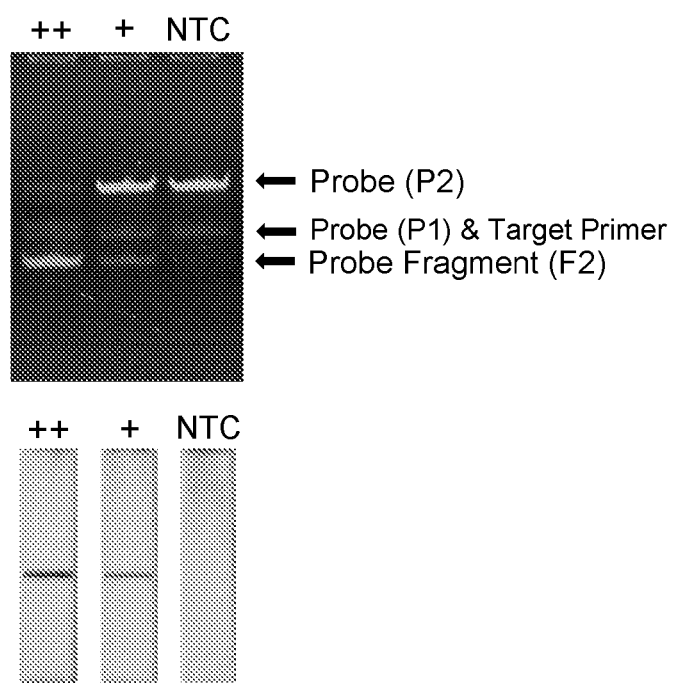
FIG. 17B. Exponential amplification using cycling process in step a)—sensitive detection of viral pathogen target with integrated reverse transcription (see Example 5.3).

In the second part of this example, the reverse transcriptase part of step a) was performed simultaneously in single integrated reaction. Reactions for step a) were carried out in a 10 μl volume containing: 0.1 pmol probe (P1), 0.2 pmol target primer, 50 μM Sp-dTTP-α-S(Biolog), 10 μM dCTP, 10 μM dGTP, 10 μM dATP (Life Technologies), 25 μM Tetramethyl Ammonium Chloride, 2 U *Bacillus* polymerase, 0.5 U first nicking agent/probe (P1) nicking agent and 5 U M-MuLV (NEB) in 1× Isothermal Amplification Buffer (NEB). Various levels (++=10 amol, +=100 zmol, NTC=no target control) of target nucleic acid viral mRNA in molecular biology water were added. Reactions were incubated for 10 min at 55° C. before being heated to 95° C. for 5 min to inactivate the enzymes. Reactions for step b) were then performed containing 5 μl of the step a) reaction, 5 pmol probe (P2) and 2.5 U of the second nicking agent in 0.5× Isothermal Amplification buffer (NEB) and 0.5× Buffer 3.1 (NEB). Following incubation at 55° C. for 20 min the entire reactions were analysed by TBE-Urea polyacrylamide gel electrophoresis (PAGE) using 15% w/v gel stained with SYBR Gold (Life Technologies) and visualised using a UV Transilluminator. Nucleic acid lateral flow analysis was also performed as described above. FIG. 17B displays the results obtained from the integrated reaction with step c) performed by gel electrophoresis (top panel) and by nucleic acid lateral flow (bottom panel). The probe fragment (F2) cleavage band on the gel and corresponding carbon deposit on the lateral flow strips were only observed in the presence of target clearly indicating the performance of the method with integrated reverse transcription in a single reaction.

Additional aspects of the invention include those listed below:

1. A method for detecting the presence of a target nucleic acid of defined sequence in a sample which method comprises the steps of:
   a) contacting said sample with:
      i. a first oligonucleotide probe (P1);
      ii. a polymerase; and
      iii. a first nicking agent;
      to produce in the presence of the target nucleic acid a double-stranded nucleic acid amplifier comprising a target derived strand containing at least one cleavage site for the first nicking agent and a probe (P1) derived strand; wherein the first oligonucleotide probe (P1) comprises a complementarity region capable of sequence specific hybridisation to the target nucleic acid; and whereby following production of the double-stranded nucleic acid amplifier: (A) the first nicking agent specifically recognises the double-stranded nucleic acid amplifier and cleaves the target derived strand of the double-stranded nucleic acid amplifier at said cleavage site to produce a primer that remains hybridised to the probe (P1) derived strand; and (B) the polymerase extends said primer to reproduce said double-stranded nucleic acid amplifier and displaces the target derived strand fragment (F1) that is 3' of said cleavage site;
   b) contacting the fragment (F1) produced in step a) with:
      i. a second oligonucleotide probe (P2); and
      ii. a second nicking agent;
      wherein the second oligonucleotide probe (P2) comprises a complementarity region capable of sequence specific hybridisation to fragment (F1) which following hybridisation to fragment (F1) produces a cleavage site for the second nicking agent; whereby the second nicking agent specifically recognises the double-stranded nucleic acid formed when the second oligonucleotide probe (P2) hybridises to fragment (F1) and cleaves said second oligonucleotide probe (P2) to produce a probe fragment (F2); and
   c) detecting the presence of the probe fragment (F2) produced in step b) wherein the presence of said detected probe fragment (F2) indicates the presence of the target nucleic acid in said sample.

2. A method according to aspect 1 wherein the probe (P1) derived strand of the double-stranded nucleic acid amplifier comprises one or more modifications that render it resistant to cleavage by the first and/or second nicking agent(s).

3. The method according to aspect 2 wherein one or more of the modifications is a phosphorothioate linkage.

4. A method according to any of aspects 1 to 3 wherein the first oligonucleotide probe (P1) comprises a complementarity region capable of sequence specific hybridisation to the target nucleic acid to produce a cleavage site for the first nicking agent in the target derived strand; and whereby the first nicking agent specifically recognises the double-stranded nucleic acid formed when the first oligonucleotide probe (P1) hybridises to the target nucleic acid in said sample and cleaves said target nucleic acid to produce a primer that remains hybridised to the probe (P1); and the polymerase extends the primer to produce the double-stranded nucleic acid amplifier which is cleaved in step a) (A).

5. A method according to any of aspects 1 to 3 wherein the first oligonucleotide probe (P1) comprises a complementarity region at its 3' end that is capable of sequence specific hybridisation to the target nucleic acid; whereby, on hybridisation of probe (P1) to the target nucleic acid, extension of probe (P1) by the polymerase forms a double-stranded nucleic acid that contains the cleavage site for the first nicking agent within the target nucleic acid strand; and whereby the first nicking agent specifically recognises said double-stranded nucleic acid and cleaves said target nucleic acid strand to produce a primer that remains hybridised to the probe (P1) derived strand; and the polymerase extends the primer to produce the double-stranded nucleic acid amplifier which is cleaved in step a) (A).

6. A method according to any of aspects 1 to 3 wherein the first oligonucleotide probe (P1) comprises a complementarity region at its 3' end that is capable of sequence specific hybridisation to the target nucleic acid and the sample is also contacted with a target nucleic acid primer; whereby, on hybridization of probe (P1) to the target nucleic acid, extension of probe (P1) by the polymerase forms a sequence that is complementary to the cleavage site of the first nicking agent; the target nucleic acid strand is separated from the extended probe (P1) derived strand; the target nucleic acid primer then hybridises to the probe (P1) derived strand and the polymerase extends the target nucleic acid primer to produce the double-stranded nucleic acid amplifier which is cleaved in step a) (A).

7. A method according to aspect 6 wherein the target nucleic acid primer does not contain the recognition sequence or cleavage site for the first nicking agent.

8. A method according to any of aspects 1 to 7 wherein the target derived strand fragment (F1) comprises a complementarity region at its 3' end that is capable of sequence specific hybridisation to oligonucleotide probe (P1); whereby, on hybridisation of fragment (F1) to probe (P1), extension of (F1) by the polymerase forms a double-stranded nucleic acid that contains the cleavage site for a nicking agent within the target nucleic acid strand.

9. A method according to any of aspects 1 to 8 wherein the target derived strand of the double-stranded nucleic acid amplifier which is cleaved in step a) (A) contains two or more cleavage sites for the first and/or second nicking agent(s).

10. A method according to any of aspects 1 to 9 wherein the first and second nicking agents are the same nicking agent.

11. A method according to any of aspects 1 to 10 wherein two or more of steps a), b) and c) are performed simultaneously.

12. A method according to any of aspects 1 to 11 wherein the second oligonucleotide probe (P2) is attached to a solid material or to a moiety that permits its attachment to a solid material.

13. A method according to any of aspects 1 to 12 wherein the probe fragment (F2) produced in step b) is attached to a moiety that permits its detection, such as a colorimetric or fluorometric dye or a moiety that is capable of attachment to a colorimetric dye e.g. biotin.

14. A method according to aspect 13 wherein said moiety is an enzyme that yields a detectable signal, such as a colorimetric or fluorometric signal, following contact with a substrate, such as a substrate that is insoluble in water.

15. A method according to any of aspects 1 to 14 wherein the presence of the probe fragment (F2) in step c) is detected by nucleic acid lateral flow.

16. A method according to aspect 15 wherein the nucleic acid lateral flow utilises one or more nucleic acids capable of sequence specific hybridisation to the probe fragment (F2).

17. The method according to aspect 15 or 16 which produces a colorimetric signal using carbon or gold, preferably carbon.

18. A method according to any of aspects 1 to 17 wherein the presence of the probe fragment (P2) in step c) is detected electrically, such as by a change in impedance resulting from the cleavage of the second oligonucleotide probe (P2).

19. A method according to any of aspects 1 to 18 wherein the level of target nucleic acid in said sample is quantified in step c).

20. A method according to any one of aspects 1 to 19 wherein the first and/or second nicking agent(s) is a naturally occurring enzyme, such as a nicking restriction endonuclease.

21. A method according to any one of aspects 1 to 20 wherein the first and/or second nicking agent(s) is an engineered enzyme, such as a mutated form of a naturally occurring enzyme or a DNAzyme.

22. A method according to any of aspects 1 to 21 wherein the first and/or second nicking agent(s) is a programmable nicking enzyme.

23. A method according to any of aspects 1 to 22 wherein the first and/or second nicking agent(s) is a double-strand cleaving agent which functions as a nicking agent due to strand preference.

24. A method according to any of aspects 1 to 23 wherein the first and/or second nicking agent(s) is a double-strand cleaving agent which functions as a nicking agent due to only one of the two strands within the double-stranded nucleic acid that is specifically recognised by said double-stranded cleaving agent being capable of cleavage.

25. A method according to any of aspects 1 to 24 wherein said target nucleic acid is single-stranded RNA, including single-stranded RNA derived from double-stranded RNA and single-stranded RNA derived from double-stranded DNA, or single-stranded DNA, including single-stranded DNA derived from single-stranded RNA and single-stranded DNA derived from double-stranded DNA.

26. A method according to aspect 25 wherein said single-stranded DNA is derived from double-stranded DNA by use of a nuclease, such as a restriction endonuclease or exonuclease III or derived from single-stranded RNA by use of reverse transcriptase.

27. A method according to any of aspects 1 to 26 wherein the presence of two or more different target nucleic acids of defined sequence are detected in the same sample.

28. The method according to aspect 27 wherein a separate series of steps a), b) and c), using different oligonucleotide probes (P1) and (P2) for each of the two or more target nucleic acids is performed, which separate series of steps may be conducted simultaneously.

29. The method according to aspect 27 wherein step a) uses a different first oligonucleotide probe (P1) for each of the two or more different target nucleic acids but the oligonucleotide probe fragment (F1) produced in step a) is the same.

30. A method according to any of aspects 1 to 29 wherein said sample is a biological sample, such as a nasal or nasopharyngeal swab or aspirate, blood or a sample derived from blood, or urine.

31. A method according to any of aspects 1 to 30 wherein said target nucleic acid is viral or derived from viral nucleic acid material, or is bacterial or derived from bacterial nucleic acid material.

32. A method according to any of aspects 1 to 31 wherein said target nucleic acid is circulating, cell-free DNA released from cancer cells or foetal cells.

33. A method according to any of aspects 1 to 32 wherein said target nucleic acid is micro RNA or derived from micro RNA.

34. A method according to any of aspects 1 to 33 wherein the target nucleic acid contains a site of epigenetic modification, such as methylation.

35. A method according to any of aspects 1 to 34 wherein the detection of said target nucleic acid is used for the diagnosis, prognosis or monitoring of a disease or a diseased state.

36. A method according to aspect 35 wherein said disease is an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, *chlamydia*, herpes, gonorrhoea, measles, mumps, rubella, cholera or smallpox.

37. A method according to aspect 35 wherein said disease is a cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma.

38. A method according to any of aspects 1 to 37 wherein the detection of said target nucleic acid is used for human genetic testing, prenatal testing, blood contamination screening, pharmacogenomics or pharmacokinetics.

39. A method according to any of aspects 1 to 38 wherein said sample is any of the following: a human sample, a forensic sample, an agricultural sample, a veterinary sample, an environmental sample or a biodefence sample.

40. A kit comprising the following:
   a) a first oligonucleotide probe (P1); and
   b) a second oligonucleotide probe (P2);
   wherein the first oligonucleotide probe (P1) and the second oligonucleotide probe (P2) are as defined in aspect 2 or 3 or any of aspects 12 to 14 as dependent on aspects 2 or 3.

41. A kit comprising the following:
   a) a first oligonucleotide probe (P1);
   b) a first nicking agent;
   c) a second oligonucleotide probe (P2); and
   d) a second nicking agent;
   wherein the first oligonucleotide probe (P1), the first nicking agent, the second oligonucleotide probe (P2) and the second nicking agent are as defined in any of aspects 1 to 10, 12 or 20 to 24.

42. A kit according to aspect 41 which further comprises a polymerase.

43. A kit according to aspect 41 or 42 which further comprises components for the detection of a probe fragment (F2) as defined in any of aspects 1 or 13 to 19.

44. A kit according to any of aspects 40 to 43 together with instructions for the performance of the method according to any of aspects 1 to 39.

45. A method of amplifying a nucleic acid signal from a target nucleic acid of defined sequence in a sample comprising steps a) and b) of any one of aspects 1 to 14 or 20 to 39, wherein amplified nucleic acid is probe fragment (F2) produced at the end of step b).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:

1. A method for detecting the presence of a target nucleic acid of defined sequence in a sample which method comprises the steps of:
   a) contacting said sample with:
      i. a first oligonucleotide probe (P1);
      ii. a polymerase;
      iii. a first nicking agent; and
      iv. one or more modified nucleotides;
      to produce in the presence of the target nucleic acid a double-stranded nucleic acid amplifier comprising a target derived strand containing at least one cleavage site for the first nicking agent and a probe (P1) derived strand; wherein the first oligonucleotide probe (P1) comprises a complementarity region capable of sequence specific hybridisation to the target nucleic acid; and whereby following production of the double-stranded nucleic acid amplifier:
      (A) the first nicking agent specifically recognises the double-stranded nucleic acid amplifier and cleaves the target derived strand of the double-stranded nucleic acid amplifier at said cleavage site to produce a primer that remains hybridised to the probe (P1) derived strand; and (B) the polymerase extends said primer to reproduce said double-stranded nucleic acid amplifier and displaces the target derived strand fragment (F1) that is 3' of said cleavage site;
   b) contacting the fragment (F1) produced in step a) with:
      i. a second oligonucleotide probe (P2); and
      ii. a second nicking agent;
      wherein the second oligonucleotide probe (P2) comprises a complementarity region capable of sequence specific hybridisation to fragment (F1) which following hybridisation to fragment (F1) produces a cleavage site for the second nicking agent; whereby the second nicking agent specifically recognises the double-stranded nucleic acid formed when the second oligonucleotide probe (P2) hybridises to fragment (F1) and cleaves said second oligonucleotide probe (P2) to produce a probe fragment (F2); and
   c) detecting the presence of the probe fragment (F2) produced in step b) wherein the presence of said detected probe fragment (F2) indicates the presence of the target nucleic acid in said sample;
   wherein the first and/or second nicking agent(s) is a double-strand cleaving agent which functions as a nicking agent due to the double-stranded nucleic acid that is specifically recognised by said double-strand cleaving agent containing one or more modifications that renders one of its strands resistant to cleavage by said double-strand cleaving agent, said modifications being integrated into the probe (P1) derived strand of the double-stranded nucleic acid amplifier and/or into fragment (F1) by the polymerase using the one or more modified nucleotides.

2. A method according to claim 1 wherein the second oligonucleotide probe (P2) is attached to a solid material or to a moiety that permits its attachment to a solid material.

3. A method according to claim 1 wherein the probe (P1) derived strand of the double-stranded nucleic acid amplifier contains one or more modifications that render it resistant to cleavage by the first and/or second nicking agent(s).

4. A method according to claim 1 wherein the double-stranded nucleic acid amplifier contains two or more nicking agent cleavage sites.

5. A method according to claim 1 wherein the sample is also contacted with a target nucleic acid primer which optionally contains the cleavage site for the first nicking agent.

6. A method according to claim 1 wherein the first oligonucleotide probe (P1) comprises a complementarity region at its 3' end that is capable of sequence specific hybridisation to the target nucleic acid; whereby, following hybridisation of probe (P1) to the target nucleic acid, extension of probe (P1) by the polymerase forms a double-stranded nucleic acid that contains the cleavage site for the first nicking agent within the target nucleic acid strand; and whereby the first nicking agent specifically recognises said double-stranded nucleic acid and cleaves said target nucleic acid strand to produce a primer that remains hybridised to the probe (P1) derived strand; and the polymerase extends the primer to produce the double-stranded nucleic acid amplifier which is cleaved in step a) (A).

7. A method according to claim 6 wherein probe (P1) contains the recognition sequence for a probe (P1) nicking agent and whereby the double-stranded nucleic acid amplifier that is formed contains two or more nicking agent cleavage sites, one or more cleavage sites in the target derived strand, and one or more cleavage sites in the probe (P1) derived strand, wherein the probe (P1) nicking agent may be the same as the first and/or second nicking agent.

8. A method according to claim 6 wherein the target nucleic acid is produced by extension of a target nucleic acid primer that contains the recognition sequence for the first nicking agent, wherein the probe (P1) nicking agent may be the same as the first and/or second nicking agent.

9. A method according to claim 1 wherein the first oligonucleotide probe (P1) comprises a complementarity region at its 3' end that is capable of sequence specific hybridisation to the target nucleic acid and the sample is also contacted with a target nucleic acid primer; whereby, on hybridisation of probe (P1) to the target nucleic acid, extension of probe (P1) by the polymerase forms a sequence that is complementary to the cleavage site of the first nicking agent; the target nucleic acid strand is separated from the extended probe (P1) derived strand; the target nucleic acid primer then hybridises to the probe (P1) derived strand and the polymerase extends the target nucleic acid primer to produce the double-stranded nucleic acid amplifier which is cleaved in step a) (A), wherein the target nucleic acid primer does or does not contain the recognition sequence or cleavage site for the first nicking agent.

10. A method according to claim 1 wherein the first oligonucleotide probe (P1) comprises the recognition sequence for a probe (P1) nicking agent and comprises a complementarity region at its 3' end that is capable of sequence specific hybridisation to the target nucleic acid and the sample is also contacted with a target nucleic acid primer that contains the recognition sequence for the first nicking agent and a probe (P1) nicking agent; whereby, following hybridisation of probe (P1) to the target nucleic acid, extension of (P1) by the polymerase forms a sequence that is capable of sequence specific hybridisation to the 3' end of the target nucleic acid primer; the target nucleic acid strand is separated from the probe (P1) derived strand; the target nucleic acid primer then hybridises to the probe (P1) derived strand and the polymerase extends the target nucleic acid primer to produce a double-stranded nucleic acid containing a cleavage site for the probe (P1) nicking agent in the probe (P1) derived strand, wherein following production of said double-stranded nucleic acid: (X) the probe (P1) nicking agent specifically recognises the double-stranded nucleic acid and cleaves the (P1) derived strand of said double-stranded nucleic acid at said cleavage site to produce a primer that remains hybridised to the target derived strand; and (Y) the polymerase extends said primer to produce the double-stranded nucleic acid amplifier which is cleaved in step a) (A), wherein the probe (P1) nicking agent may be the same as the first and/or second nicking agent.

11. A method according to claim 1 wherein the first oligonucleotide probe (P1) comprises a complementarity region capable of sequence specific hybridisation to the target nucleic acid to produce a cleavage site for the first nicking agent in the target derived strand; and whereby the first nicking agent specifically recognises the double-stranded nucleic acid formed when the first oligonucleotide probe (P1) hybridises to the target nucleic acid in said sample and cleaves said target nucleic acid to produce a primer that remains hybridised to the probe (P1); and the polymerase extends the primer to produce the double-stranded nucleic acid amplifier which is cleaved in step a) (A).

12. A method according to claim 1 wherein the target derived strand fragment (F1) comprises a complementarity region at its 3' end that is capable of sequence specific hybridisation to oligonucleotide probe (P1); whereby, on hybridisation of fragment (F1) to probe (P1), extension of (F1) by the polymerase forms a double-stranded nucleic acid that contains the cleavage site for a nicking agent within the target nucleic acid strand.

13. A method according to claim 1 wherein the target derived strand of the double-stranded nucleic acid amplifier which is cleaved in step a) (A) contains two or more cleavage sites for the first and/or second nicking agent(s).

14. A method according to claim 1 wherein the first and second nicking agents are the same nicking agent.

15. A method according to claim 1 wherein the probe fragment (F2) produced in step b) is attached to a moiety that permits its detection.

16. A method according to claim 1 wherein the presence of the probe fragment (F2) in step c) is detected by nucleic acid lateral flow.

17. A method according to claim 16 which produces a colorimetric signal using carbon or gold.

18. A method according to claim 1 wherein the presence of the probe fragment (P2) in step c) is detected electrically.

19. A method according to claim 1 wherein the first and/or second and/or probe (P 1) nicking agent(s) is selected from the group consisting of a naturally occurring enzyme, and an engineered enzyme.

20. A method according to claim 1 wherein the first and/or second nicking agent(s) is a double-strand cleaving agent which functions as a nicking agent due to the double-stranded nucleic acid that is specifically recognised by said double-stranded cleaving agent containing one or more phosphorothioate linkage modifications integrated into the double-stranded nucleic acid by the polymerase using one or more alpha thiol modified deoxynucleotides that renders one of its strands resistant to cleavage by said double-strand cleaving agent(s).

21. A method according to claim 1 wherein said target nucleic acid is single-stranded RNA, including single-stranded RNA derived from double-stranded RNA and single-stranded RNA derived from double-stranded DNA, or single-stranded DNA, including single-stranded DNA derived from single-stranded RNA and single-stranded DNA derived from double-stranded DNA, including single-stranded DNA derived from double-stranded DNA by use of a nuclease or derived from single-stranded RNA by use of a reverse transcriptase.

22. A method according to claim 1 wherein the presence of two or more different target nucleic acids of defined sequence are detected in the same sample wherein a separate series of steps a), b) and c), using different oligonucleotide probes (P1) and (P2) for each of the two or more target nucleic acids is performed, or wherein step a) uses a different first oligonucleotide probe (P1) for each of the two or more different target nucleic acids but the fragment (F1) produced in step a) is the same.

23. A method according to claim 1 wherein said sample is selected from the group consisting of a human sample, a forensic sample, an agricultural sample, a veterinary sample, an environmental sample and a biodefence sample, including a biological sample.

24. A method according to claim 1 wherein said target nucleic acid is viral or derived from viral nucleic acid material, bacterial or derived from bacterial nucleic acid material, circulating cell-free DNA released from cancer cells or foetal cells, or microRNA or derived from micro RNA, or the target nucleic acid contains a site of epigenetic modification.

25. A method according to claim 1 wherein the detection of said target nucleic acid is used for the diagnosis, prognosis or monitoring of a disease or a diseased state, including a disease or diseased state selected from the group consisting of an infectious disease, including but not limited to HIV, influenza, RSV, Rhinovirus, norovirus, tuberculosis, HPV, meningitis, hepatitis, MRSA, Ebola, *Clostridium difficile*, Epstein-Barr virus, malaria, plague, polio, *chlamydia*, herpes, gonorrhoea, measles, mumps, rubella, cholera or smallpox, and a cancer, including but not limited to colorectal cancer, lung cancer, breast cancer, pancreatic cancer, prostate cancer, liver cancer, bladder cancer, leukaemia, esophageal cancer, ovarian cancer, kidney cancer, stomach cancer or melanoma.

26. A kit comprising the following:
  a) a first oligonucleotide probe (P1);
  b) a first nicking agent;
  c) a second oligonucleotide probe (P2);
  d) a second nicking agent; and
  e) one or more modified nucleotides;
  wherein the first oligonucleotide probe (P1), the first nicking agent, the second oligonucleotide probe (P2) and the second nicking agent are as defined in claim 1;
  and wherein said kit optionally additionally comprises one or more of the following:
  i) a polymerase;
  ii) a probe (P1) nicking agent; and
  iii) a target nucleic acid primer.

27. A kit according to claim 26 comprising:
  a) a probe (P1) nicking agent;
  b) a first nicking agent;
  c) a first oligonucleotide probe (P1) that contains a complementarity region at its 3' end that is capable of sequence specific hybridisation to a target nucleic acid and contains the recognition sequence for the probe (P1) nicking agent;
  d) a target nucleic acid primer that contains a complementary region at its 3' end that has the same sequence as the target nucleic acid and contains the recognition sequence for the first nicking agent;
  e) a polymerase;
  f) a second nicking agent; and
  g) a second oligonucleotide probe (P2) that contains a complementarity region capable of sequence specific hybridisation to a fragment displaceable from the target nucleic acid primer and a cleavage site for the second nicking agent.

28. A kit according to claim 26 which further comprises components for the detection of a probe fragment (F2) as defined in claim 1.

29. A method according to claim 15 wherein the moiety that permits the detection of the probe fragment (F2) is selected from a colorimetric or fluorometric dye, a moiety that is capable of attachment to a colorimetric dye, and an enzyme that yields a detectable signal following contact with a substrate.

* * * * *